(12) United States Patent
Hiraoka et al.

(10) Patent No.: US 9,405,187 B2
(45) Date of Patent: *Aug. 2, 2016

(54) SALT, ACID GENERATOR AND RESIST COMPOSITION

(75) Inventors: Takashi Hiraoka, Hannan (JP); Hiromu Sakamoto, Ibaraki (JP); Koji Ichikawa, Toyonaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/170,990

(22) Filed: Jun. 28, 2011

(65) Prior Publication Data

US 2011/0318688 A1    Dec. 29, 2011

(30) Foreign Application Priority Data

Jun. 29, 2010    (JP) .................. 2010-147211

(51) Int. Cl.
| | |
|---|---|
| G03F 7/004 | (2006.01) |
| C07D 207/12 | (2006.01) |
| C07D 211/46 | (2006.01) |
| C07D 233/60 | (2006.01) |
| C07D 307/77 | (2006.01) |
| C07D 327/08 | (2006.01) |
| G03F 7/039 | (2006.01) |

(52) U.S. Cl.
CPC ............ *G03F 7/0045* (2013.01); *C07D 207/12* (2013.01); *C07D 211/46* (2013.01); *C07D 233/60* (2013.01); *C07D 307/77* (2013.01); *C07D 327/08* (2013.01); *G03F 7/0046* (2013.01); *G03F 7/0397* (2013.01)

(58) Field of Classification Search
USPC ......... 568/35; 562/30, 104, 105; 546/26, 218; 548/400, 452, 556, 950
See application file for complete search history.

(56) References Cited

U.S. PATENT DOCUMENTS

| | | | |
|---|---|---|---|
| 7,304,175 B2 | 12/2007 | Harada et al. | |
| 7,439,006 B2 | 10/2008 | Yoshida et al. | |
| 7,579,132 B2 | 8/2009 | Harada et al. | |
| 7,612,217 B2 | 11/2009 | Sakamoto et al. | |
| 7,648,817 B2 * | 1/2010 | Kato et al. | 430/270.1 |
| 8,663,899 B2 * | 3/2014 | Ichikawa | G03F 7/0045 430/270.1 |
| 2001/0038970 A1 | 11/2001 | Cameron et al. | |
| 2006/0194982 A1 | 8/2006 | Harada et al. | |
| 2008/0044738 A1 | 2/2008 | Harada et al. | |
| 2008/0076063 A1 | 3/2008 | Yoshida et al. | |
| 2008/0081925 A1 | 4/2008 | Sakamoto et al. | |
| 2009/0148791 A1 * | 6/2009 | Kodama et al. | 430/270.1 |
| 2009/0269700 A1 * | 10/2009 | Yonemura et al. | 430/281.1 |
| 2010/0015555 A1 * | 1/2010 | Utsumi et al. | 430/286.1 |
| 2010/0081088 A1 * | 4/2010 | Kawaue et al. | 430/285.1 |
| 2010/0119974 A1 * | 5/2010 | Hada et al. | 430/281.1 |
| 2011/0117495 A1 * | 5/2011 | Ichikawa et al. | 430/270.1 |
| 2011/0171576 A1 | 7/2011 | Yamaguchi et al. | |
| 2013/0022925 A1 * | 1/2013 | Ichikawa | G03F 7/0045 430/281.1 |

FOREIGN PATENT DOCUMENTS

| | | | |
|---|---|---|---|
| JP | 7-333851 | A | 12/1995 |
| JP | 11-052575 | A | 2/1999 |
| JP | 2005258124 | A * | 9/2005 |
| JP | 2006-257078 | A | 9/2006 |
| JP | 2008-013551 | A | 1/2008 |
| JP | 2008-127367 | A | 6/2008 |
| JP | 2012-13807 | A | 1/2012 |

OTHER PUBLICATIONS

Machine translation JP 2005-258124. Sep. 22, 2005.*
The Office Action, dated Mar. 10, 2015, issued in the corresponding Japanese Patent Application No. 2011-142717.

* cited by examiner

*Primary Examiner* — Cynthia H Kelly
*Assistant Examiner* — Alyssa L Cepluch
(74) *Attorney, Agent, or Firm* — Birch, Stewart, Kolasch & Birch, LLP

(57) ABSTRACT

The present invention is a salt represented by the formula (I)

$$Z^+ \; {}^-O_3S-\underset{R^2}{\overset{R^1}{C}}-L^1-\underset{R^3}{\overset{(R^4)_m}{W^1}}$$

wherein $R^1$ and $R^2$ independently represent a fluorine atom or a $C_1$ to $C_6$ perfluoroalkyl group; $L^1$ represents a $C_1$ to $C_{17}$ divalent saturated hydrocarbon group, a —$CH_2$— contained in the saturated hydrocarbon group may be replaced by —O— or —CO—; ring $W^1$ represents a $C_2$ to $C_{36}$ heterocycle; $R^3$ represents a hydrogen atom or a $C_1$ to $C_{12}$ hydrocarbon group, a —$CH_2$— contained in the hydrocarbon group may be replaced by —O— or —CO—; $R^4$ in each occurrence independently represent a $C_1$ to $C_6$ hydrocarbon group, a —$CH_2$— contained in the hydrocarbon group may be replaced by —O— or —CO—; m represents an integer of 0 to 6; and $Z^+$ represents an organic cation.

8 Claims, No Drawings

SALT, ACID GENERATOR AND RESIST COMPOSITION

CROSS-REFERENCE TO RELATED APPLICATIONS

This application claims priority to Japanese Application No. 2010-147211 filed in Japan on Jun. 29, 2010. The entire disclosures of Japanese Application No. 2010-147211 is incorporated hereinto by reference.

BACKGROUND OF THE INVENTION

1. Field of the Invention

The present invention relates to a salt, an acid generator and a resist composition.

2. Background Information

A resist composition containing triphenyl sulfonium 1-((3-hydroxy adamantyl)methoxycarbonyl)difluoro methanesulfonate is described in Patent document, JP2006-257078-A, as an acid generator.

However, with the resist composition which contains the conventional salt as an acid generator, the exposure margin (EL) and focus margin (DOF) to be provided from the resist composition may be not always satisfied with.

SUMMARY OF THE INVENTION

The present invention provides following inventions.
<1> A salt represented by the formula (I)

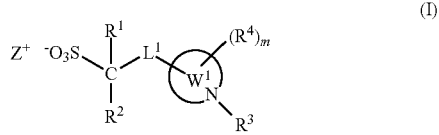

wherein $R^1$ and $R^2$ independently represent a fluorine atom or a $C_1$ to $C_6$ perfluoroalkyl group;

$L^1$ represents a $C_1$ to $C_{17}$ divalent saturated hydrocarbon group, a —$CH_2$— contained in the saturated hydrocarbon group may be replaced by —O— or —CO—;

ring $W^1$ represents a $C_2$ to $C_{36}$ heterocycle;

$R^3$ represents a hydrogen atom or a $C_1$ to $C_{12}$ hydrocarbon group, a —$CH_2$— contained in the hydrocarbon group may be replaced by —O— or —CO—;

$R^4$ in each occurrence independently represent a $C_1$ to $C_6$ hydrocarbon group, a —$CH_2$— contained in the hydrocarbon group may be replaced by —O— or —CO—;

m represents an integer of 0 to 6; and $Z^+$ represents an organic cation.

<2> The salt according to <1>, wherein $L^1$ is a group represented by the formula (L1-1a).

wherein $L^a$ represents a single bond or a $C_1$ to $C_{15}$ saturated hydrocarbon group and \* represent a bond to —C($R^1$)($R^2$)—.

<3> The salt according to <1> or <2>, wherein $Z^+$ is a triaryl sulfonium cation.

<4> An acid generator comprising the salt according to any one <1> to <3>.

<5> A resist composition comprising;
the acid generator according to <4>, and
a resin,
wherein the resin has an acid-labile group, and is insoluble or poorly soluble in an aqueous alkali solution but becomes soluble in aqueous alkali solution by the action of an acid.

<6> The resist composition according to <5>, which further comprises a basic compound.

<7> A method for producing a resist pattern comprising steps of;

(1) applying the resist composition according to <5> or <6> onto a substrate;

(2) drying the applied composition to form a composition layer;

(3) exposing the composition layer using an exposure apparatus;

(4) heating the exposed composition layer, and (5) developing the heated composition layer using a developing apparatus.

According to a salt of the present invention, it is possible to obtain a resist composition which achieves satisfactory EL at producing a resist pattern and wide DOF in the pattern.

DETAILED DESCRIPTION OF THE PREFERRED EMBODIMENTS

In the present specification, any group exemplified below is applicable to any of the chemical formulae having a similar group with optionally selecting the number of carbon atoms, unless otherwise specified.

When a group enables linear and branched chain and/or cyclic structures, all structures may be included and may simultaneously present in one group, unless otherwise specified.

When there is a stereoisomeric form, all stereoisomeric forms are included.

Each group enables monovalent, or di- or more-valent group depending on the bonded position and bonding form.

"(meth)acrylic monomer" means at least one monomer having a structure of "$CH_2$=CH—CO—" or "$CH_2$=C($CH_3$)—CO—", as well as "(meth)acrylate" and "(meth)acrylic acid" mean "at least one acrylate or methacrylate" and "at least one acrylic acid or methacrylic acid", respectively.

<Salt Represented by the Formula (I)>

The salt of the present invention is represented by the formula (I);

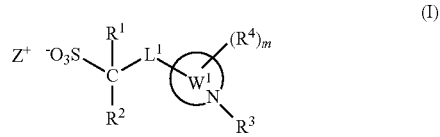

wherein $R^1$ and $R^2$ independently represent a fluorine atom or a $C_1$ to $C_6$ perfluoroalkyl group;

$L^1$ represents a $C_1$ to $C_{17}$ divalent saturated hydrocarbon group and a —$CH_2$— contained in the saturated hydrocarbon group may be replaced by —O— or —CO—;

ring $W^1$ represents a $C_2$ to $C_{36}$ heterocycle;

$R^3$ represents a hydrogen atom or a $C_1$ to $C_{12}$ hydrocarbon group and a —$CH_2$— contained in the hydrocarbon group may be replaced by —O— or —CO—;

R⁴ in each occurrence independently represent a $C_1$ to $C_6$ hydrocarbon group and a —$CH_2$— contained in the hydrocarbon group may be replaced by —O— or —CO—;

m represents an integer 0 to 6;

$Z^+$ represents an organic cation.

Examples of the perfluoroalkyl group include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

The divalent saturated hydrocarbon group may be a linear chain alkanediyl group, a branched chain alkanediyl group, a mono- or polycyclic divalent saturated cyclic hydrocarbon group and combined two or more thereof.

Specific examples of the linear chain alkanediyl group include methylene, ethylene, propane-1,3-diyl, propane-1,2-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl,ethane-1,1-diyl, propane-1,1-diyl and propane-2,2-diyl groups.

Specific examples of the branched chain alkanediyl group include a group in which a linear chain alkanediyl group has a side chain of an alkyl group(especially a $C_1$ to $C_4$ alkyl group such as methyl, ethyl, propyl, isopropyl, butyl, sec-butyl, tert-butyl groups) such as butan-1,3-diyl, 2-methylopropane-1,3-diyl, 2-methylpropane-1,2-diyl, pentan-1,4-diyl and 2-methylbutane-1,4-diyl groups.

Specific examples of the saturated cyclic hydrocarbon group include a monocyclic saturated cyclic hydrocarbon group, cycloalkanediyl group, such as cyclobutan-1,3-diyl, cyclopentan-1,3-diyl, cyclohexan-1,2-diyl, cyclohexan-1,4-diyl, cyclooctan-1,2-diyl and cyclooctan-1,5-diyl groups; and a polycyclic saturated cyclic hydrocarbon group such as norbornane-2,3-diyl, norbornane-1,4-diyl, norbornane-2,5-diyl, adamantane-1,5-diyl and adamantane-2,6-diyl groups.

Examples divalent of the saturated cyclic hydrocarbon group may also include the group in which any one of hydrogen atom on a monovalent saturated cyclic hydrocarbon group described below is removed.

The heterocycle may be a ring having one or more nitrogen atom, and it may further have one or more nitrogen atom, one or more oxygen atom, or one or more sulfur atom. The heterocycle may have any of aromaticity or non-aromaticity, and any of a monocyclic or a polycyclic compound, or condensed or bridged ring.

Specific examples of the heterocycle include a ring below. One or more —$CH_2$—contained in the heterocycle may be replaced by —O— or —CO—. Among these, a ring represented by the formula (W1), a ring represented by the formula (W2) and a ring represented by the formula (W3) are preferable. * represents a bond to $L^1$.

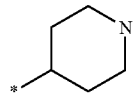

(W1)

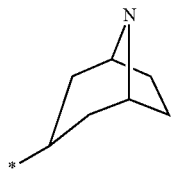

(W2)

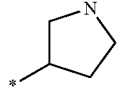

(W3)

The hydrocarbon group includes an aliphatic hydrocarbon group, a saturated cyclic hydrocarbon group and an aromatic hydrocarbon group.

Examples of the aliphatic hydrocarbon group include an alkyl group such as methyl, ethyl, n-propyl, 1-methylethyl (isopropyl), n-butyl, 1,1-dimethylethyl(tert-butyl), 2,2-dimethylethyl, 1-methylpropyl, 2-methylpropyl, 1,2-dimethylpropyl, 2,2-dimethylpropyl, 1-ethylpropyl, n-pentyl, 1-methylbutyl, 2-methylbutyl, 3-methylbutyl,n-hexyl, 1-propylbutyl, 1-methylpentyl, 1,4-dimethylhexyl, heptyl, 1-methylheptyl, octyl, methyloctyl, methylnonyl, 2-ethylhexyl, nonyl, decyl, undecyl and dodecyl groups.

The saturated cyclic hydrocarbon group may be any of a mono- or poly-cyclic saturated cyclic hydrocarbon group. Examples of the monocyclic saturated cyclic hydrocarbon groups include a cycloalkyl group such as cyclopentyl, cyclohexyl, methylcyclohexyl, dimethylcyclohexyl, cycloheptyl, cyclooctyl. Examples of the polycyclic saturated cyclic hydrocarbon groups include a group which is obtained by hydrogenated a condensed aromatic hydrocarbon group such as hydronaphthyl, and a bridged cyclic hydrocarbon group such as adamantyl, norbornyl and methylnorbornyl groups. Examples of the saturated cyclic hydrocarbon group further include a group in which a bridged ring (e.g. norbornane ring) is condensed with a monocycle (e.g. cycloheptane ring, cyclohexane ring) or a polycycle (e.g. decahydronaphthalene ring), a group in which two or more bridged rings are condensed, and a combination thereof (e.g. methylcyclohexyl, dimethylcyclohexyl and methyl norbornyl groups) as follows.

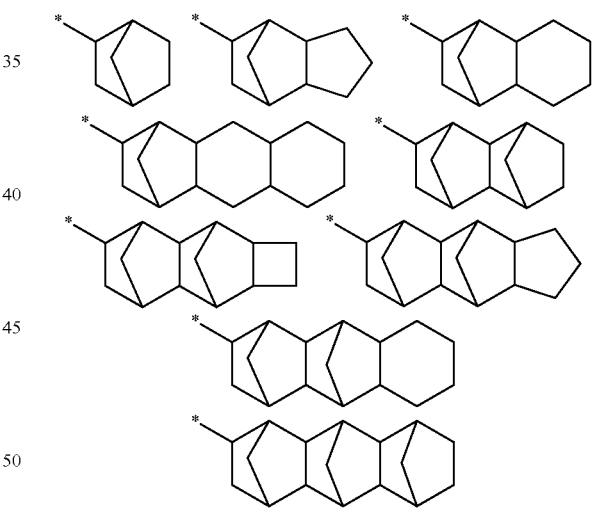

Examples of the aromatic hydrocarbon group include an aryl group such as phenyl, naphthyl, p-methylphenyl, p-ethylphenyl, p-tert-butylphenyl, p-cyclohexylphenyl, p-methoxyphenyl, p-adamantylphenyl, tolyl, xylyl, cumenyl, mesityl, biphenyl, anthryl, phenanthryl, 2,6-diethylphenyl and 2-methyl-6-ethylphenyl groups.

In the salt represented by the formula (I), $R^1$ and $R^2$ independently are preferably a trifluoromethyl or a fluorine atom, and more preferably a fluorine atom.

Examples of $L^1$ in which one or more —$CH_2$— contained in the divalent saturated hydrocarbon group is replaced by —O— or —CO— include, for example, groups represented by the formula (L1-1) to the formula (L1-6). Among these, any of the groups represented by the formula (L1-1) to the formula (L1-4) and the formula (L1-6) are preferable, any of the groups represented by the formula (L1-1), the formula (L1-2) and the formula (L1-6) are more preferable, and the group represented by the formula (L1-1) or the formula (L1-6) is more preferable. In the formula (L1-1) to the formula (L1-6), the group is represented so as to correspond with two sides of the formula (I), that is, the left side of the group bonds to $C(R^1)(R^2)$— and the right side of the group bonds to $W^1$ ring. Examples of the formula (L1-1) to the formula (L1-6) are the same as above.

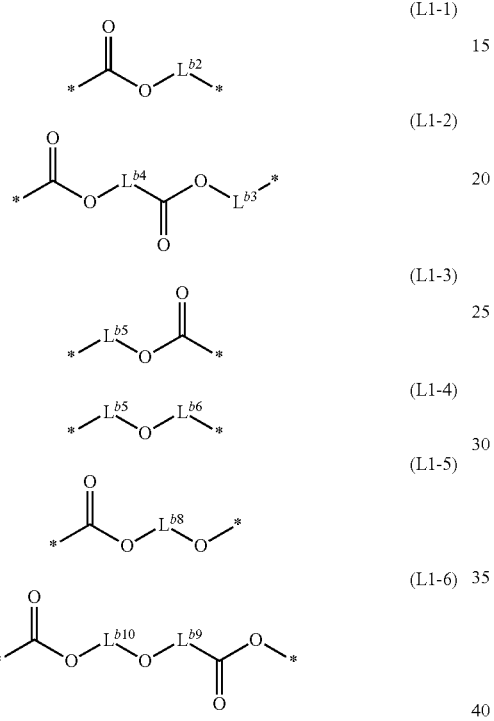

wherein $L^{b2}$ represents a single bond or a $C_1$ to $C_{15}$ divalent saturated hydrocarbon group;

$L^{b3}$ represents a single bond or a $C_1$ to $C_{12}$ divalent saturated hydrocarbon group;

$L^{b4}$ represents a $C_1$ to $C_{13}$ divalent saturated hydrocarbon group;

$L^{b5}$ represents a $C_1$ to $C_{15}$ divalent saturated hydrocarbon group;

$L^{b6}$ and $L^{b7}$ independently represent a $C_1$ to $C_{15}$ divalent saturated hydrocarbon group;

$L^{b8}$ represents a $C_1$ to $C_{14}$ divalent saturated hydrocarbon group;

$L^{b9}$ represents a single bond or a $C_1$ to $C_{11}$ divalent saturated hydrocarbon group;

$L^{b10}$ represents a $C_1$ to $C_{11}$ divalent saturated hydrocarbon group.

The divalent group represented by the formula (L1-1) in which $L^{b2}$ represents a single bond or one or more —$CH_2$—, and the divalent group represented by the formula (L1-6) in which $L^{b9}$ represents a single bond or one or more —$CH_2$— are preferable, and $L^{b10}$ represents a group as follows is more preferable.

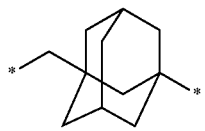 [SMILES: *CC12CC3CC(CC(*)(C3)C1)C2]

The divalent group represented by the formula (L1-1) is more preferably a group represented by the formula (L1-1) in which $L^{b2}$ represents a single bond or a C1 to C6 divalent saturated hydrocarbon group, and still more preferably a group represented by the formula (L1-1) in which $L^{b2}$ represents a single bond or —$CH_2$—.

In the formula (L1-6), $L^{b9}$ more preferably represents a single bond or a C1 to C6 divalent saturated hydrocarbon group, and still more preferably a single bond or —$CH_2$—.

Examples of the divalent group represented by the formula (L1-1) include a group below.

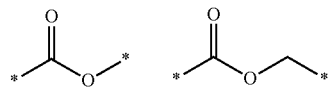

The divalent group represented by the formula (L1-1) is preferably group represented by formula (L1-1a)

wherein $L^a$ represents a single bond or a $C_1$ to $C_{15}$ saturated hydrocarbon group and * represent a bond to —$C(R^1)(R^2)$—.

Examples of the divalent group represented by the formula (L1-2) include a group below.

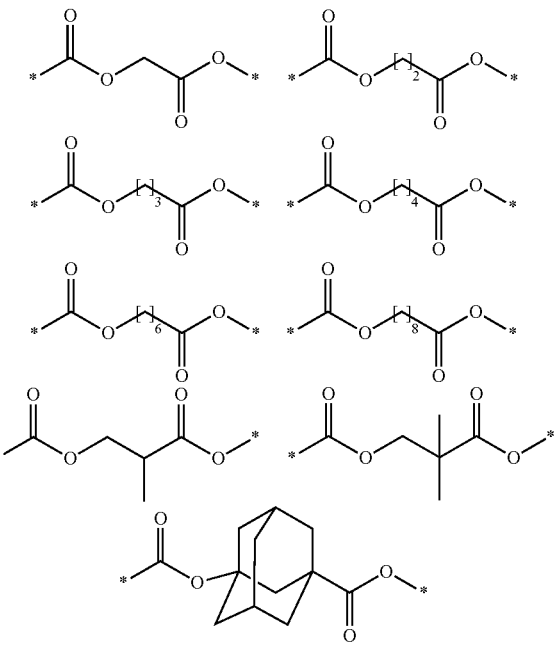

-continued

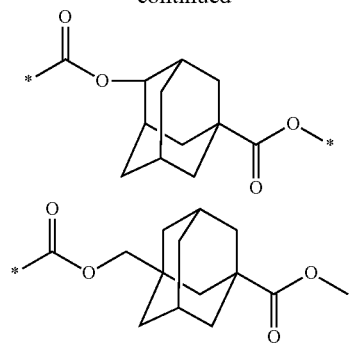

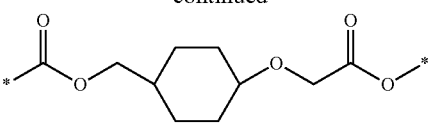

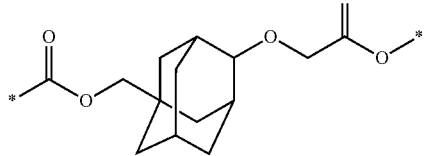

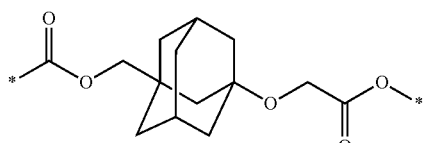

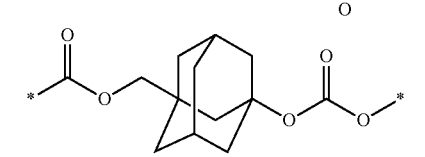

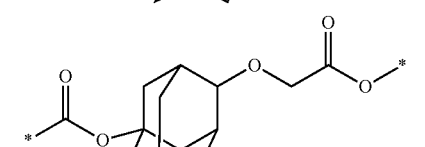

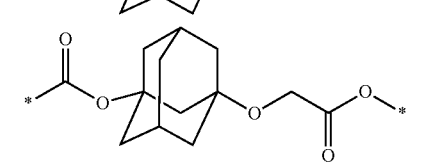

Examples of the divalent group represented by the formula (L1-3) include a group below.

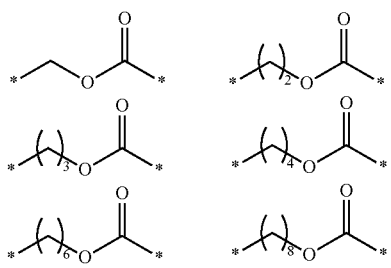

Examples of the divalent group represented by the formula (L1-4) include a group below.

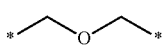

Examples of the divalent group represented by the formula (L1-5) include a group below.

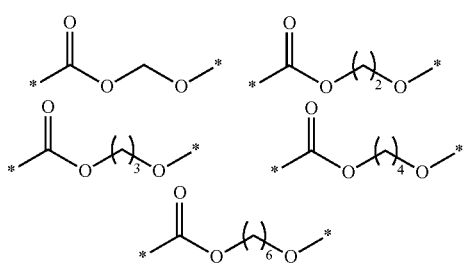

Examples of the divalent group represented by the formula (L1-6) include a group below.

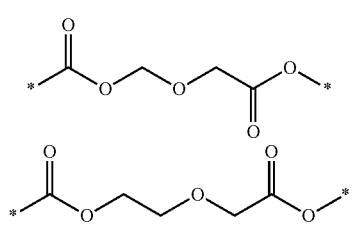

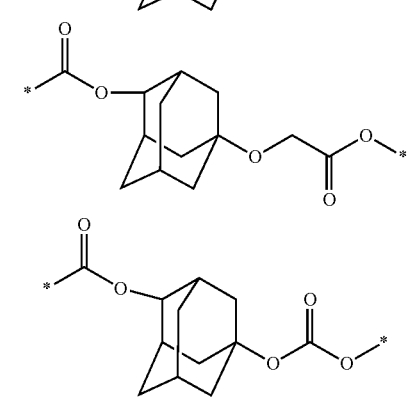

Examples of $R^3$ preferably include a hydrogen atom, a methyl group, an ethyl group and a tert-butoxycarbonyl group, and more preferably, a hydrogen atom, a methyl group or a tert-butoxycarbonyl group.

Examples of $R^4$ preferably include a hydrogen atom, a methyl group, an ethyl group, a methylcarbonyloxy group (an acetyloxy group), and an ethyl carbonyloxy group.

Examples of the salt represented by the formula (I) include a salt below.

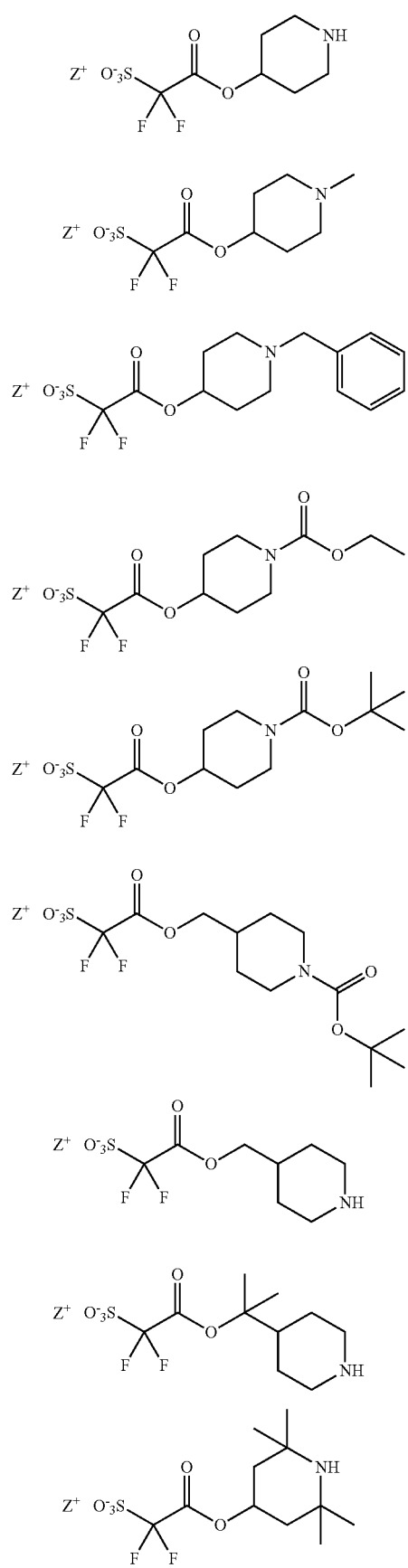
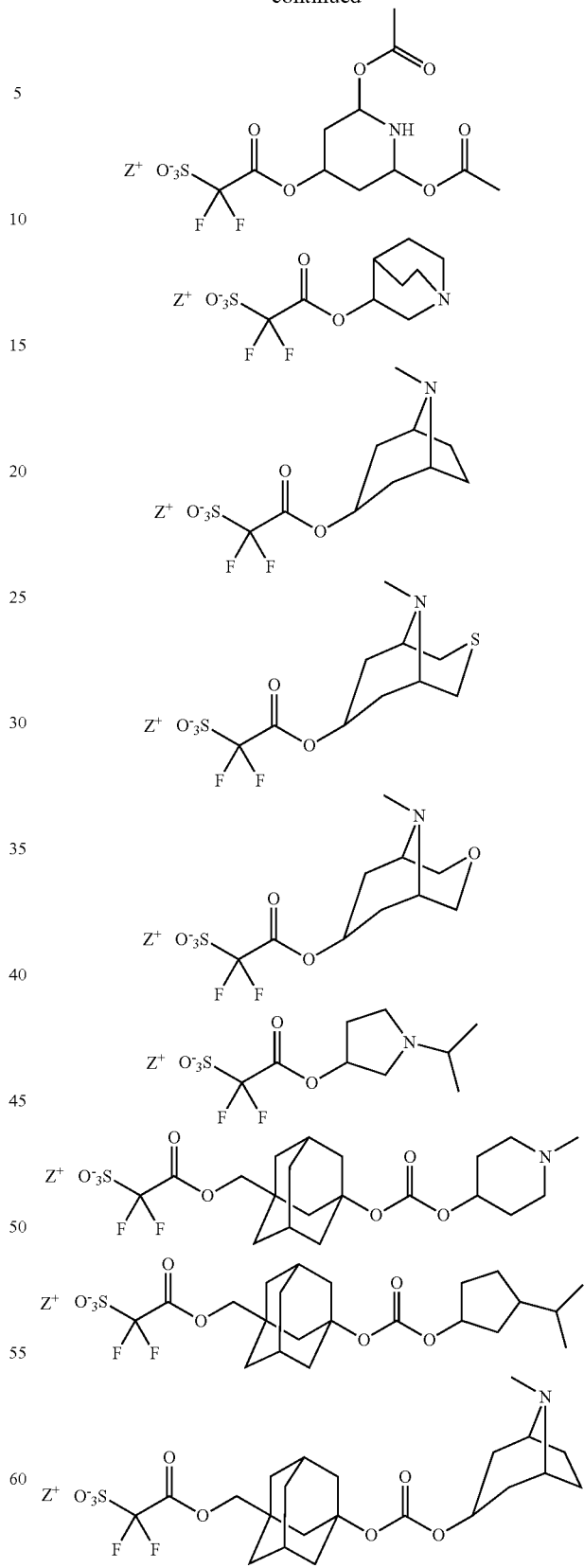
Examples of the cation $Z^+$ include an onium cation, for example, a sulfonium cation, an iodonium cation, an ammonium cation, a benzothiazolium cation and a phosphonium cation. Among these, a sulfonium cation and an iodonium cation are preferable, and an aryl sulfonium cation is more preferable.

Specific examples of $Z^+$ include a cation represented by any of the formula (Z1) to the formula (Z4).

(Z1)

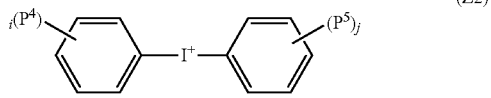

(Z2)

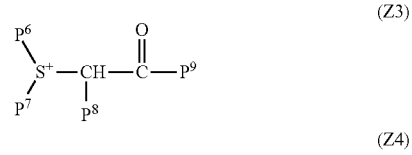

(Z3)

(Z4)

wherein $P^a$, $P^b$ and $P^c$ independently represent a $C_1$ to $C_{30}$ aliphatic hydrocarbon group, a $C_3$ to $C_{36}$ saturated cyclic hydrocarbon group or a $C_6$ to $C_{18}$ aromatic hydrocarbon group, one or more hydrogen atom contained in the aliphatic hydrocarbon group may be replaced with a hydroxy group, a $C_1$ to $C_{12}$ alkoxy group or a $C_6$ to $C_{18}$ aromatic hydrocarbon group, one or more hydrogen atom contained in the saturated cyclic hydrocarbon group may be replaced with a halogen atom, a $C_2$ to $C_4$ acyl group or a glycidyloxy group, one or more hydrogen atom contained in the aromatic hydrocarbon group may be replaced with a halogen atom, a hydroxy group, a $C_1$ to $C_{36}$ aliphatic hydrocarbon group, a $C_3$ to $C_{36}$ saturated cyclic hydrocarbon group or a $C_1$ to $C_{12}$ alkoxy group, or $P^a$ and $P^b$ may be bonded to form at least one hetero atom-containing ring.

$P^4$ and $P^5$ independently represent a hydroxy group, a $C_1$ to $C_{12}$ aliphatic hydrocarbon or a $C_1$ to $C_{12}$ alkoxy group;

$P^6$ and $P^7$ independently represent a $C_1$ to $C_{36}$ aliphatic hydrocarbon or a $C_3$ to $C_{36}$ saturated cyclic hydrocarbon group;

$P^8$ represents a hydrogen atom, a $C_1$ to $C_{36}$ aliphatic hydrocarbon group, a $C_3$ to $C_{36}$ saturated cyclic hydrocarbon group or a $C_6$ to $C_{18}$ aromatic hydrocarbon group;

$P^9$ represents a $C_1$ to $C_{12}$ aliphatic hydrocarbon group, a $C_3$ to $C_{18}$ saturated cyclic hydrocarbon group or a $C_6$ to $C_{18}$ aromatic hydrocarbon group, one or more hydrogen atom contained in the aromatic hydrocarbon group may be replaced with a $C_1$ to $C_{12}$ aliphatic hydrocarbon group, a $C_1$ to $C_{12}$ alkoxy group, a $C_3$ to $C_{18}$ saturated cyclic hydrocarbon or an alkyl carbonyloxy group;

$P^6$ and $P^7$ may be bonded together to form a three- to twelve-membered ring (preferably a three- to seven-membered ring) with a sulfur atom which is bonded thereto, $P^8$ and $P^9$ may be bonded together to form a three- to twelve-membered ring (preferably a three- to seven-membered ring) with —CH—CO— which is bonded thereto, and one or more —CH$_2$— contained in the ring may be replaced by —O—, —S— or —CO—;

$P^{10}$ to $P^{15}$ independently represent a hydroxy group, a $C_1$ to $C_{12}$ aliphatic hydrocarbon or a $C_1$ to $C_{12}$ alkoxy group;

E represents —S— or —O—;

i, j, p, r, x and y independently represent an integer of 0 to 5;

q represents an integer of 0 or 1;

v and w independently represent an integer of 0 to 4.

Examples of the aliphatic hydrocarbon group and the saturated cyclic haydrocarbon include the same examples defined above.

Examples of the alkoxyl group include methoxy, ethoxy, n-propoxy, isopropoxy, n-butoxy, sec-butoxy, tert-butoxy, n-pentoxy, n-hexyloxy, heptyloxy, octyloxy, 2-ethylhexoxy, nonyloxy, decyloxy, undecyloxy and dodecyloxy groups.

Examples of the halogen atom include fluorine, chlorine, bromine and iodine atoms.

Examples of the acyl group include acetyl, propionyl and butyryl groups.

Examples of the alkylcarbonyloxy group include methylcarbonyloxy, ethylcarbonyloxy, n-propylcarbonyloxy, isopropylcarbonyloxy, n-butylcarbonyloxy, sec-butylcarbonyloxy, tert-butylcarbonyloxy, pentylcarbonyloxy, hexylcarbonyloxy, octylcarbonyloxy and 2-ethylhexylcarbonyloxy groups.

The three- to twelve-membered ring formed by $P^6$ and $P^7$ as well as $P^8$ and $P^9$ bonded together, respectively, include a saturated cyclic hydrocarbon group, an aromatic hydrocarbon and a combination thereof.

Among these, Examples of the ring formed by $P^6$ and $P^7$ bonded together with a sulfur atom includes, for example, thiolane-1-ium ring (tetrahydrothiophenium ring), thian-1-ium ring and 1,4-oxathian-4-ium ring.

Examples of the ring formed by $P^8$ and $P^9$ bonded together with —CH—CO— include oxocycloheptane ring, oxocyclohexane ring, oxonorbornane ring and oxoadamantane ring.

The aliphatic hydrocarbon group of $P^6$ to $P^8$ is preferably a group having 1 to 12 carbon atoms, the saturated cyclic hydrocarbon group is preferably a group having 3 to 36 carbon atoms, and more preferably a group having 4 to 12 carbon atoms.

In the formula (Z1) to the formula (Z4), a preferred aliphatic hydrocarbon group includes methyl, ethyl, n-propyl, isopropyl, n-butyl, sec-butyl, tert-butyl, pentyl, hexyl, octyl and 2-ethylhexyl groups.

A preferred saturated cyclic hydrocarbon group includes cyclopropyl, cyclobutyl, cyclopentyl, cyclohexyl, cycloheptyl, cyclodecyl, 2-alkyl-2-adamantyl, 1-(1-adamantyl)-1-alkyl group and isobornyl groups.

A preferred aromatic hydrocarbon group includes phenyl, 4-methylphenyl, 4-ethylphenyl, 4-tert-butylphenyl, 4-cyclohexylphenyl, 4-methoxyphenyl, biphenyl and naphthyl groups.

Examples of the aliphatic hydrocarbon group which is substituted with the aromatic hydrocarbon group, i.e., aralkyl group, include benzyl, phenethyl, phenylpropyl, trityl, naphthylmethyl and naphthylethyl groups.

Among the cations represented by the formula (Z1) to the formula (Z4), the cation represented by the formula (Z1) is preferable, the cation represented by the formula (Z5) is more preferable, and triphenyl sulfonium cation (all z are 0 in the formula (Z5)) is further more preferable.

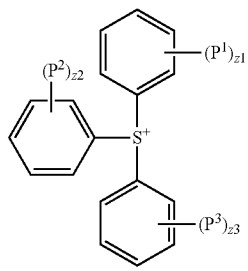

(Z5)

wherein $P^1$ to $P^3$ independently represent a halogen atom, a hydroxy group, a C1 to C36 aliphatic hydrocarbon group, a $C_3$ to $C_{36}$ saturated cyclic hydrocarbon group or a $C_1$ to $C_{12}$ alkoxy group, or two of $P^1$ to $P^3$ may be bonded together to form a ring which contains a hetero atom;

z1, z2 and z3 independently represent an integer of 0 or 5.

The aliphatic hydrocarbon group here preferably has 1 to 12 carbon atoms, and the saturated cyclic hydrocarbon group preferably has 4 to 36 carbon atoms.

The aliphatic hydrocarbon group may be substituted with a hydroxy group, a $C_1$ to $C_{12}$ alkoxy group or a $C_6$ to $C_{18}$ aromatic hydrocarbon group, the saturated cyclic hydrocarbon group may be substituted with a halogen atom, a $C_2$ to $C_4$ acyl group and a glycidyloxy group.

Among these, $P^1$ to $P^3$ are independently preferably a halogen atom (more preferably fluorine atom), a hydroxy group, a $C_1$ to $C_{12}$ alkyl group or a $C_1$ to $C_{12}$ alkoxy group, or two of $P^1$ to $P^3$ are preferably bonded together to form —O— or a ring which contains a sulfur atom.

z1, z2 and z3 are independently preferably 0 or 1.

Specific examples of the cation of the formula (Z1) or the formula (Z5) include a cation below.

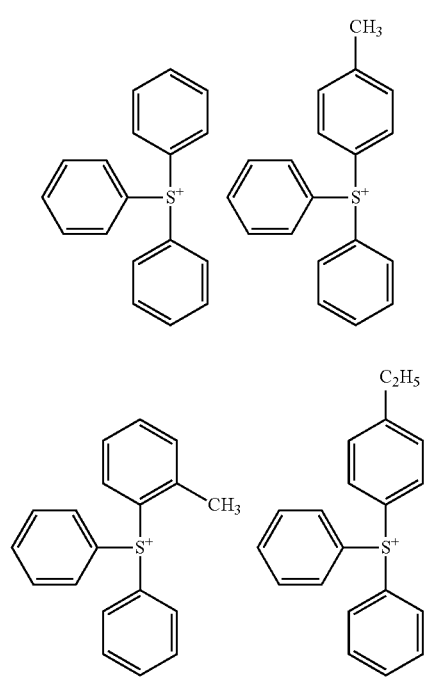

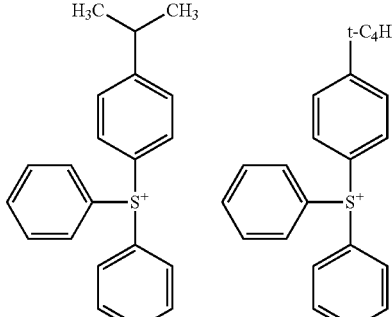

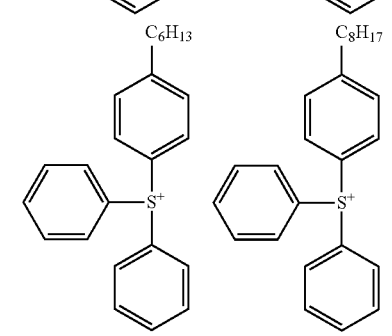

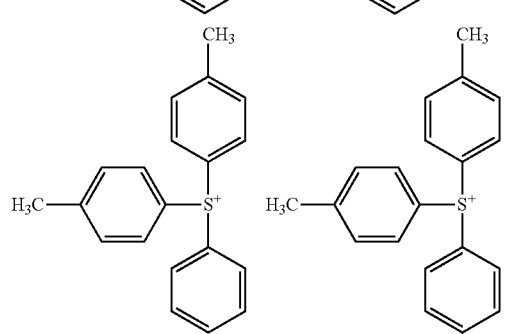

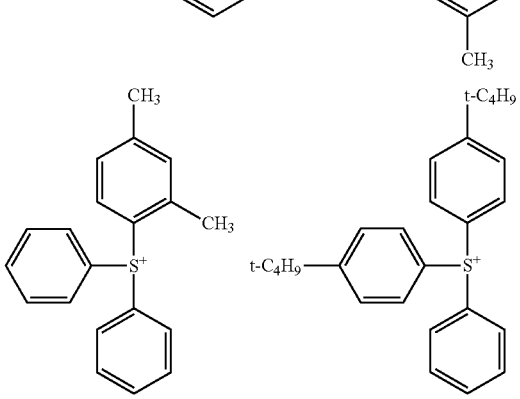

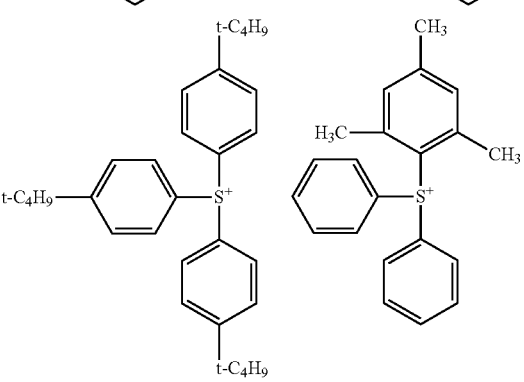

-continued
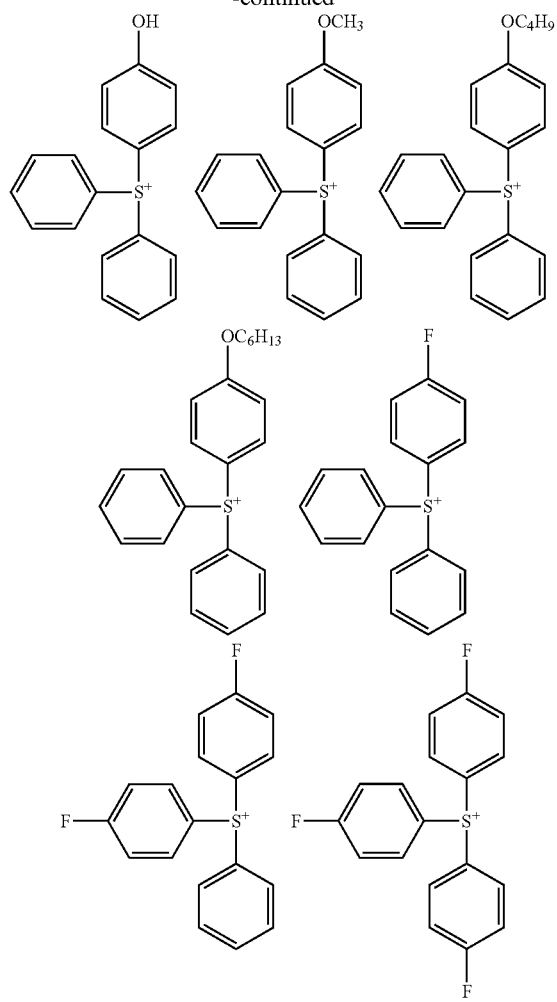
Specific examples of the cation of the formula (Z5) which formed by a sulfur atom-containing ring include a cation below.
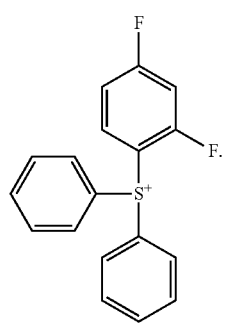 [SMILES: Fc1ccc([S+](c2ccccc2)c2ccccc2)c(F)c1]
-continued
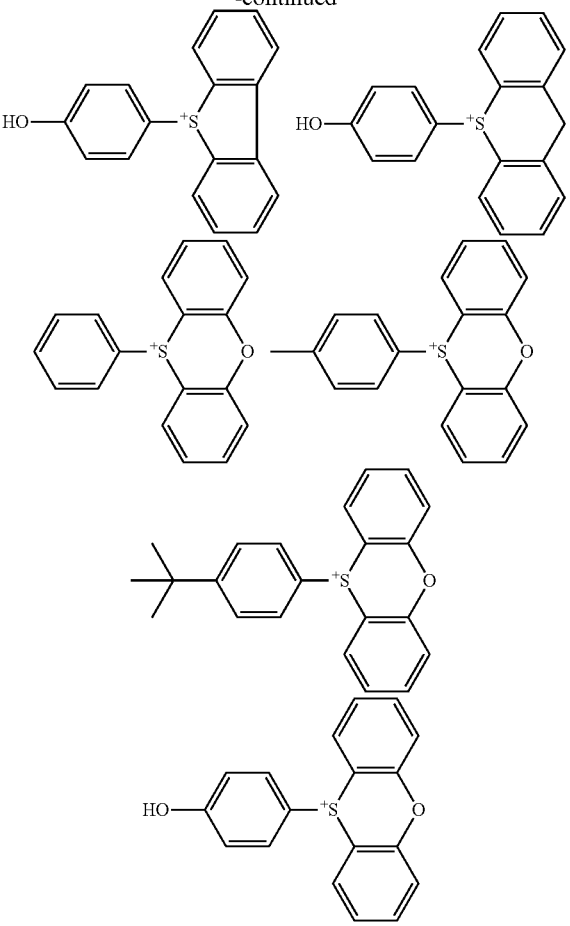
Specific examples of the cation of the formula (Z1) include a cation below.
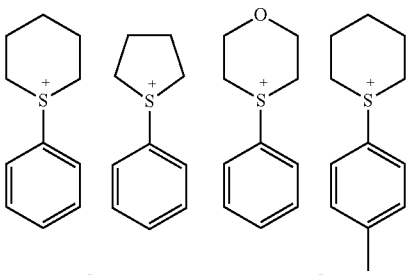
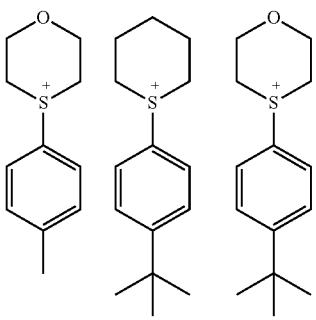
Specific examples of the cation of the formula (Z2) include a cation below.

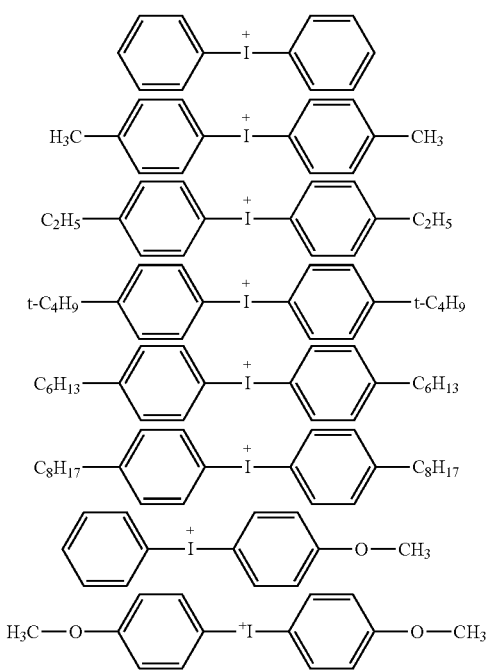
Specific examples of the cation of the formula (Z3) include a cation below.
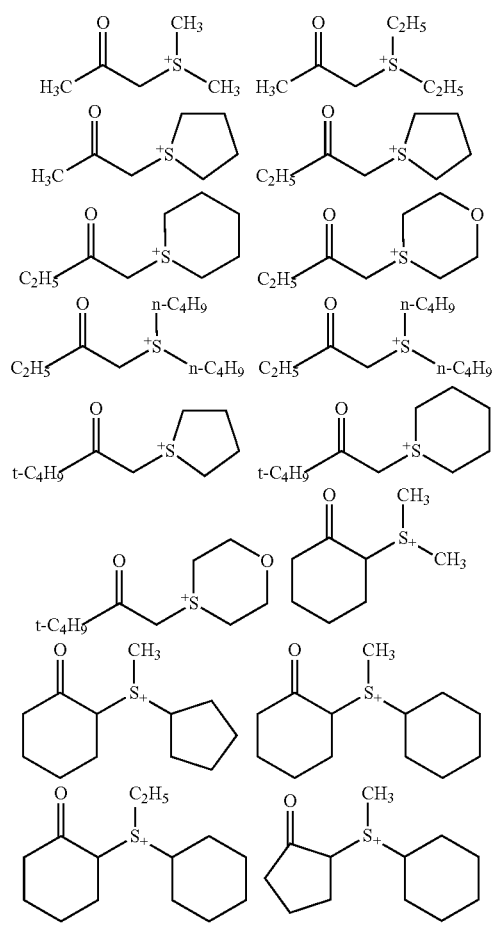
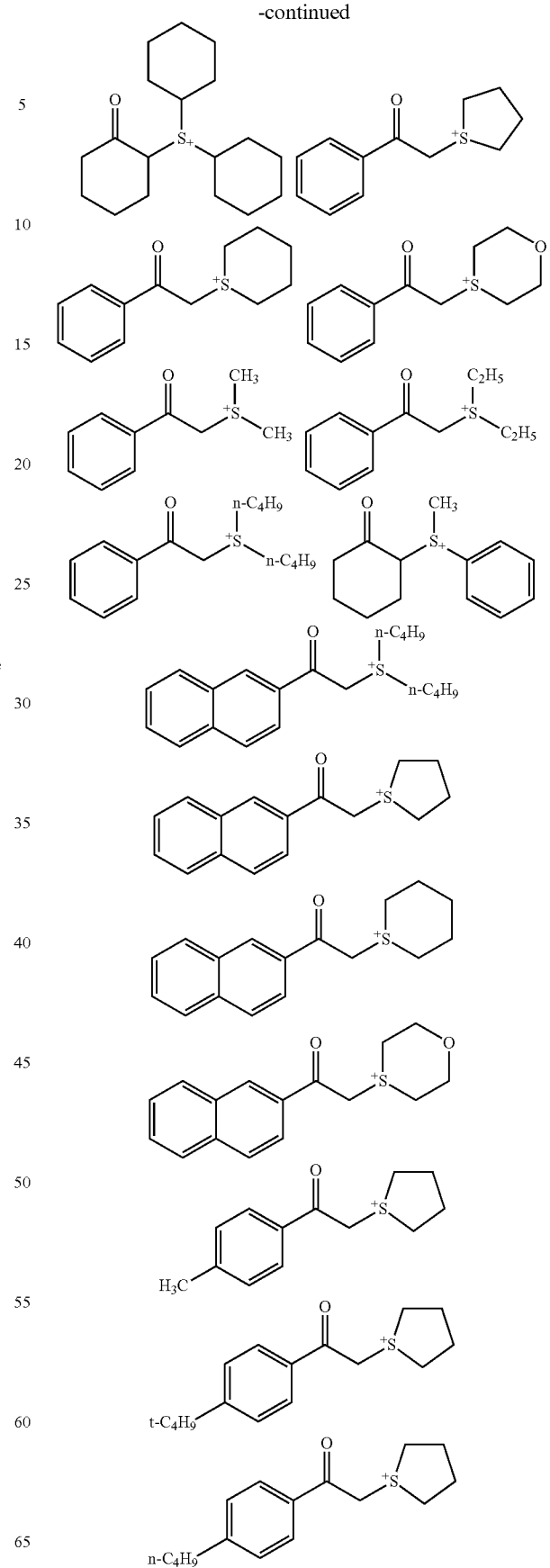

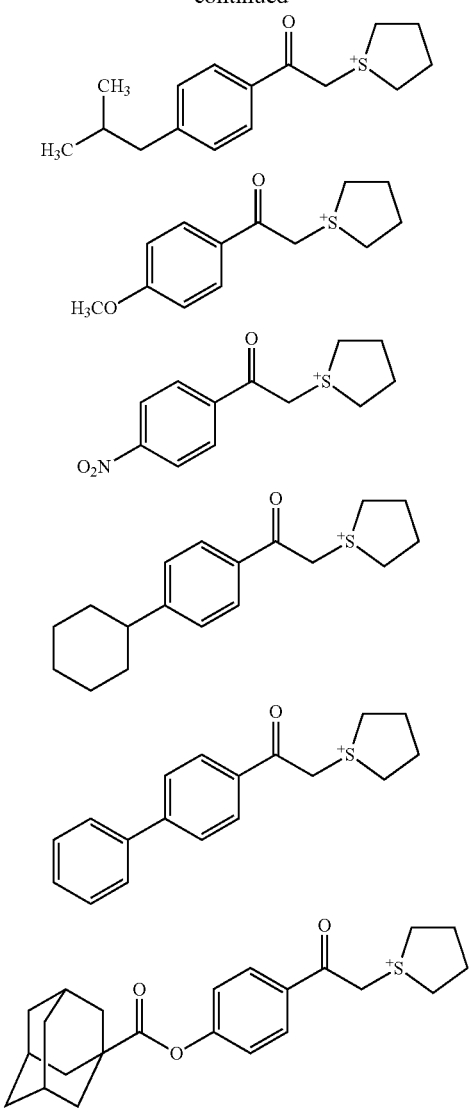
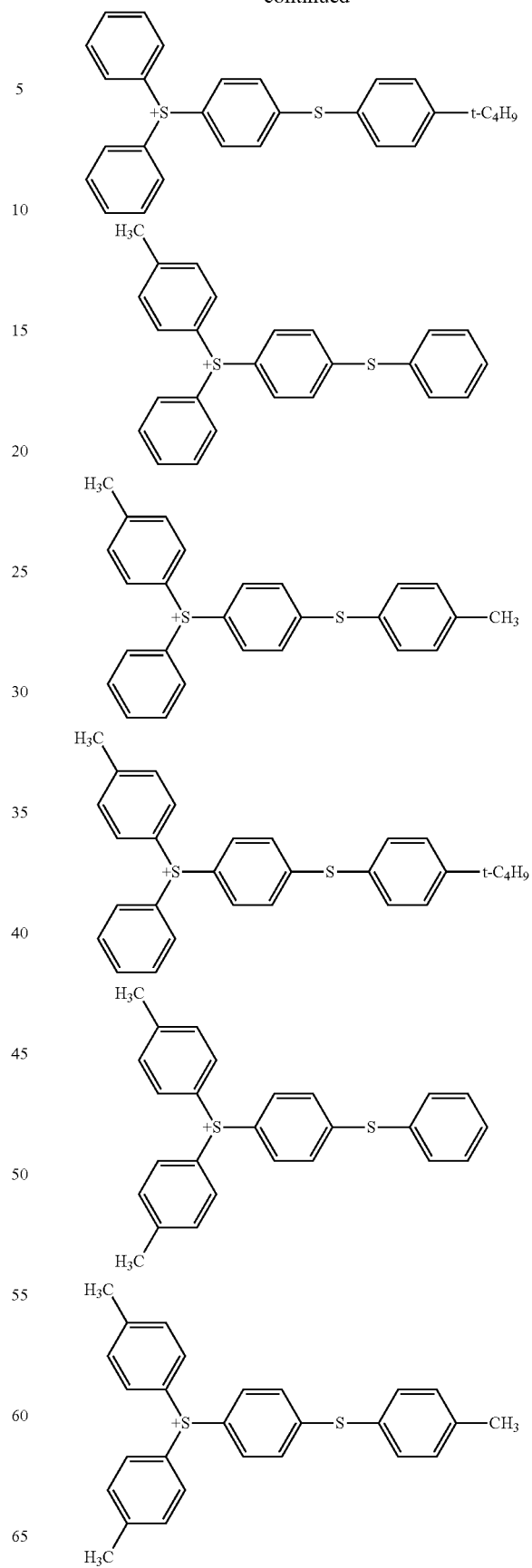
Specific examples of the cation of the formula (Z4) include a cation below.
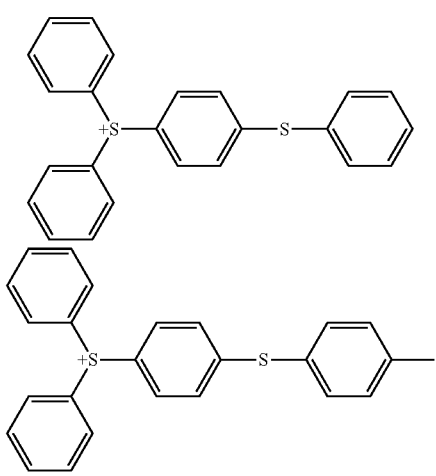

-continued
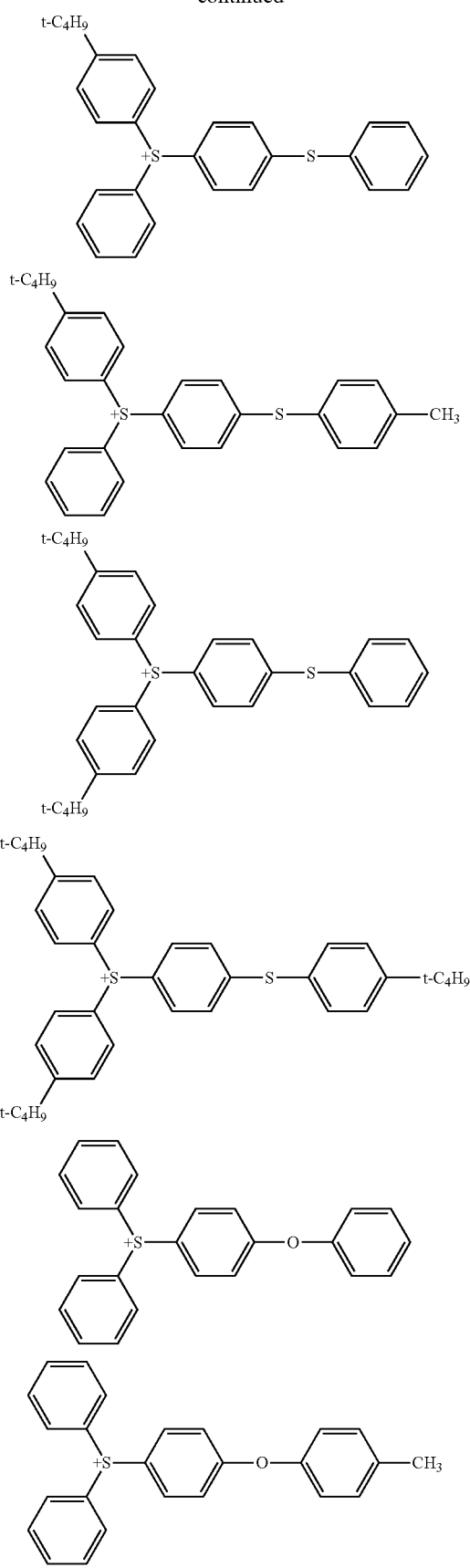
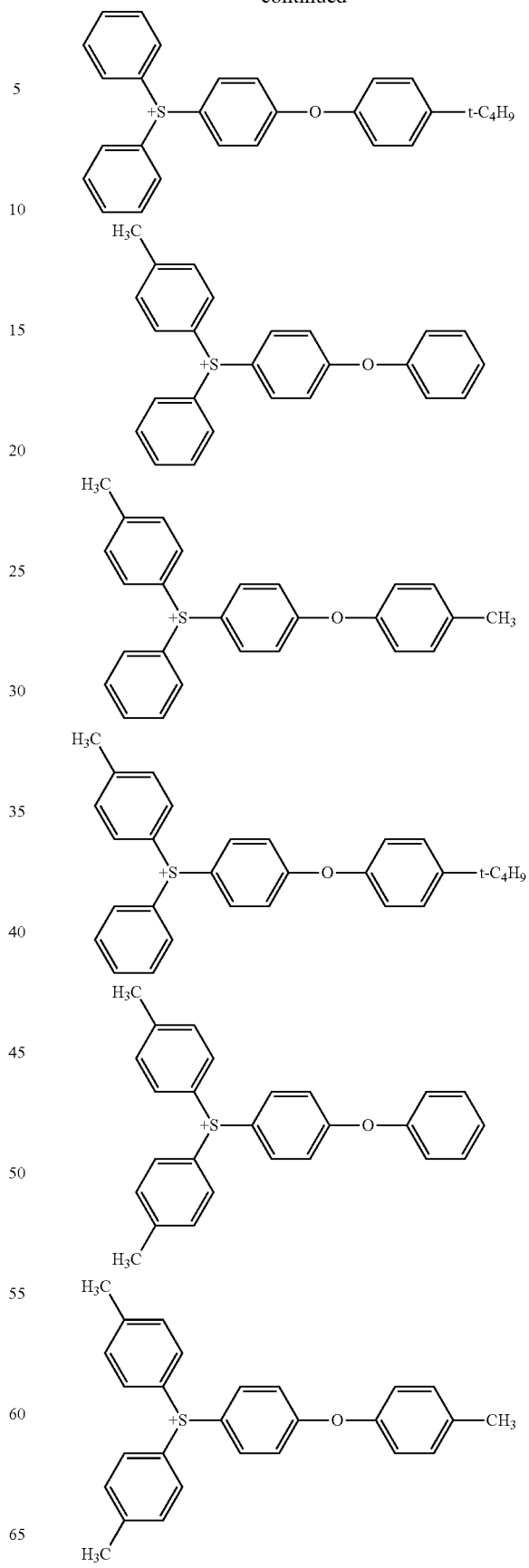

23
-continued
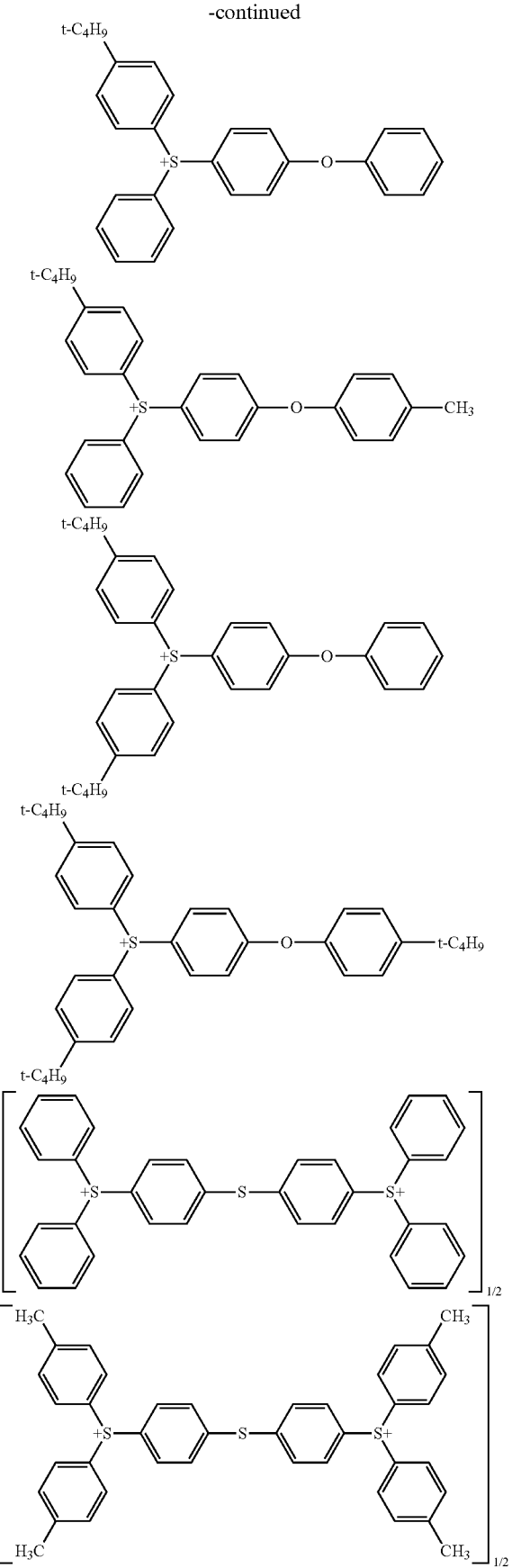
24
-continued
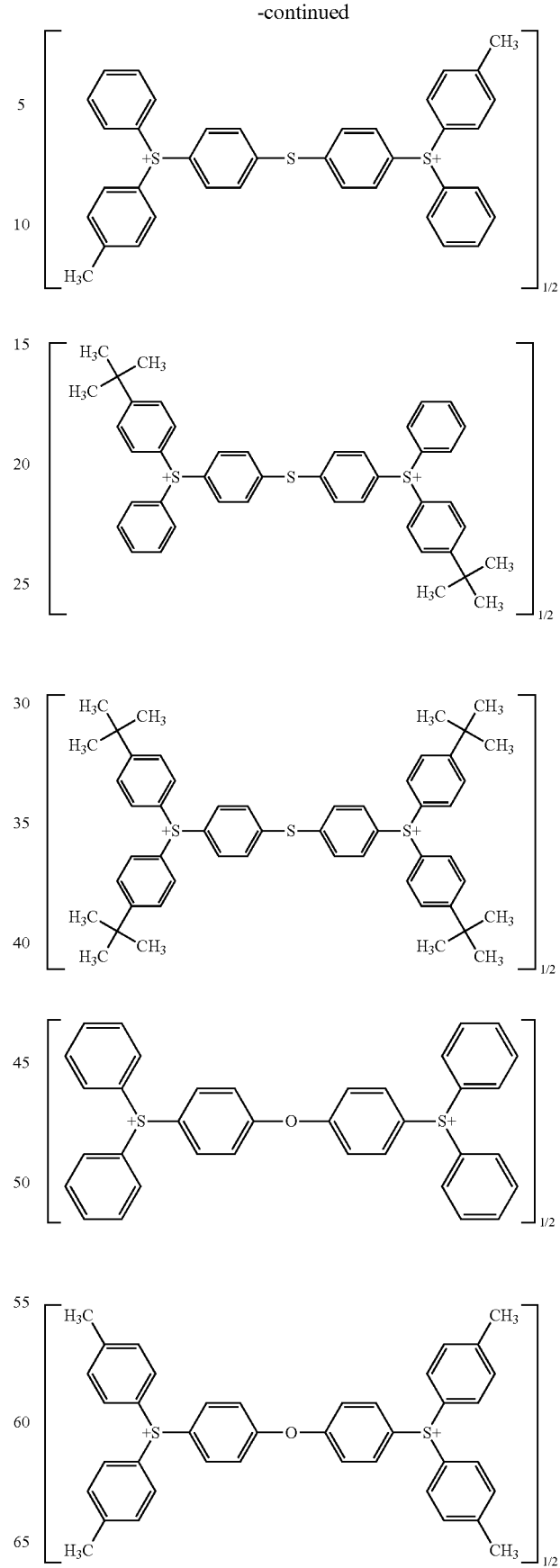

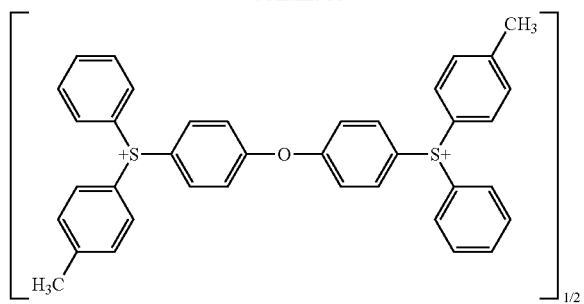
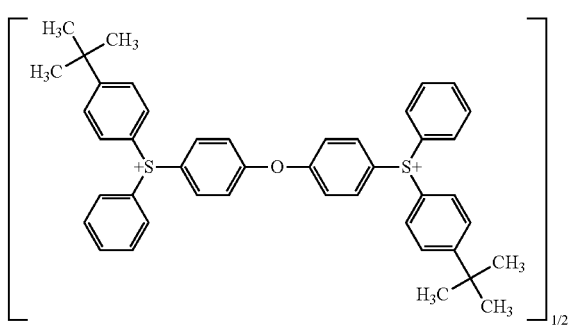
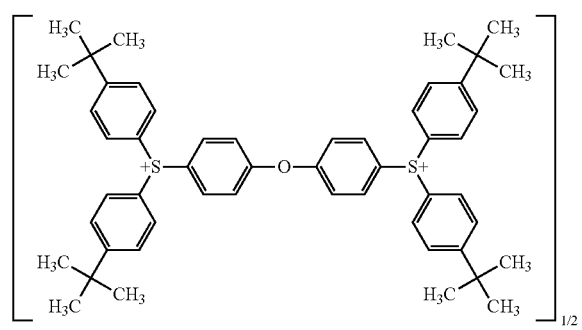
The salt represented by the formula (I) is a compound combined the above anion with an organic cation. The above anion and the organic cation may optionally be combined, but the salts shown below are preferable. In the formula below, the definition of the substituents represent the same meaning as described above.
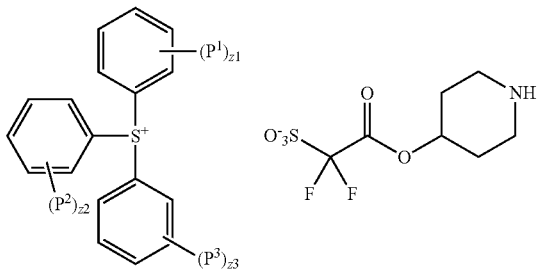
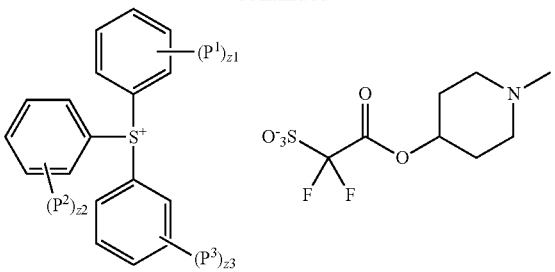
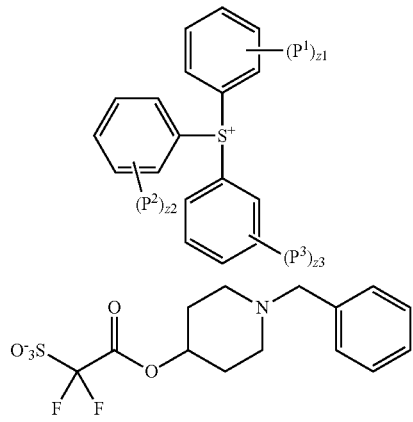
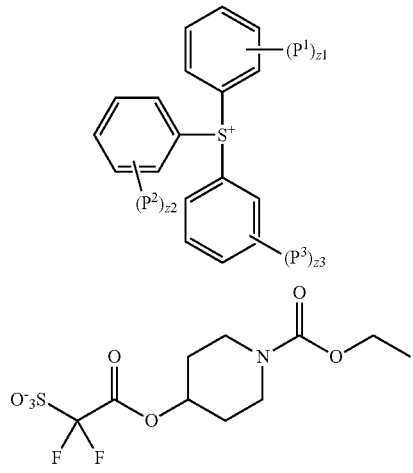
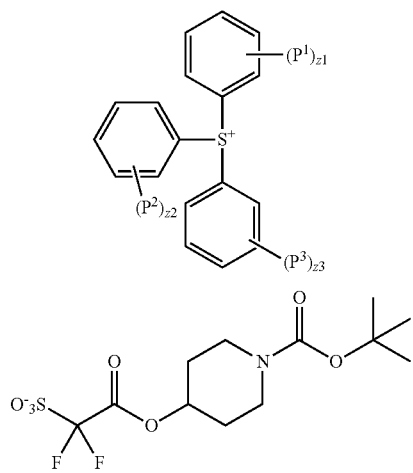

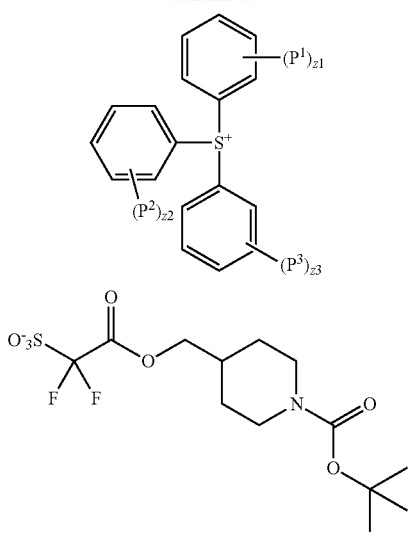
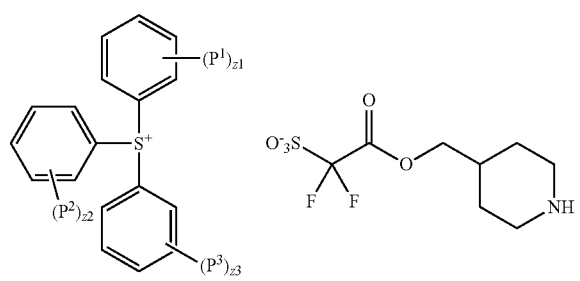
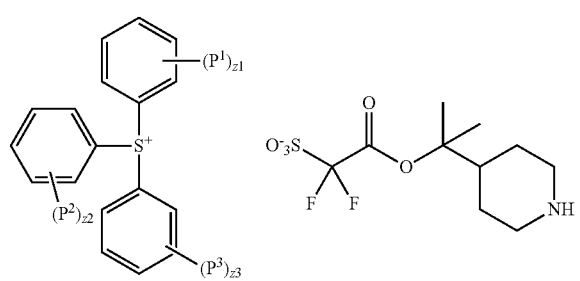
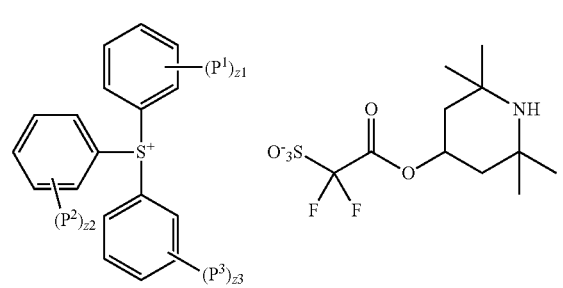
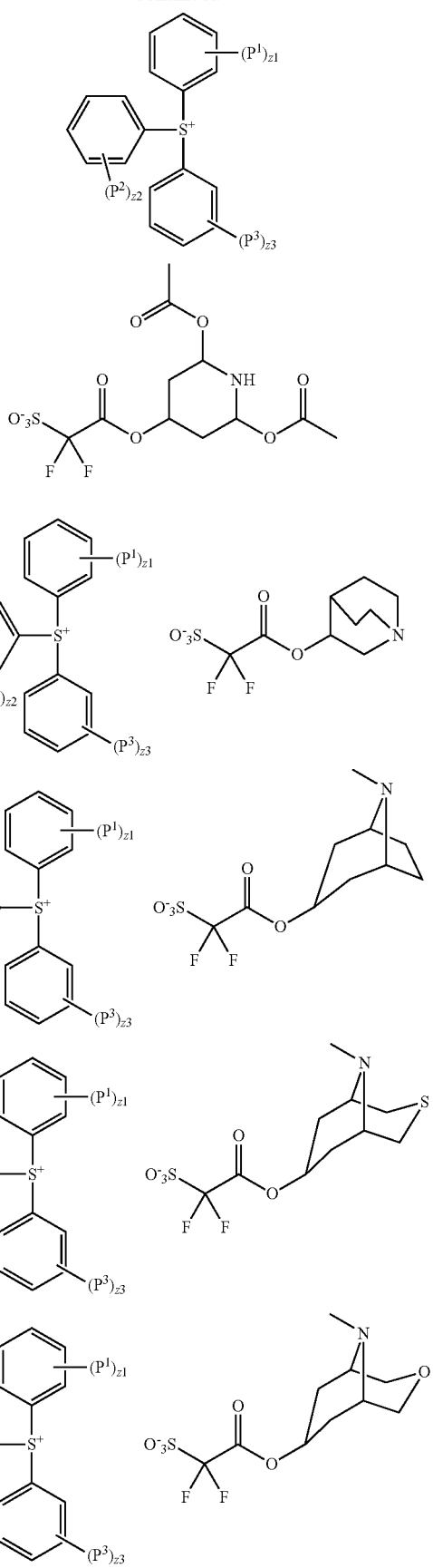

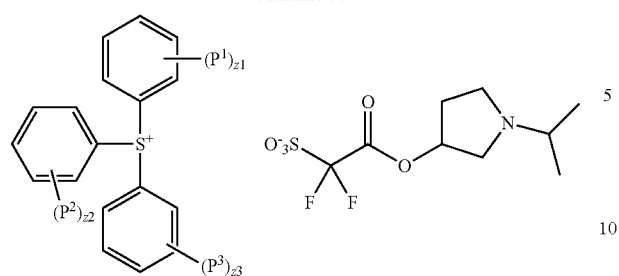
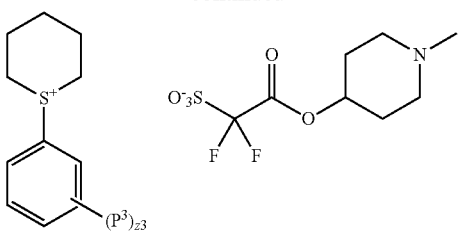
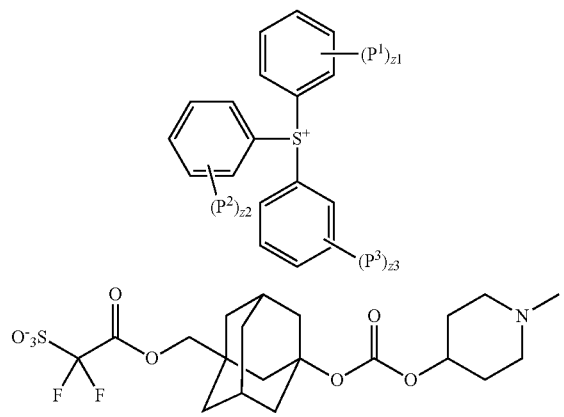
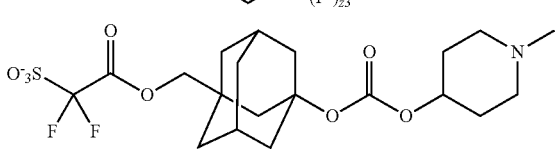
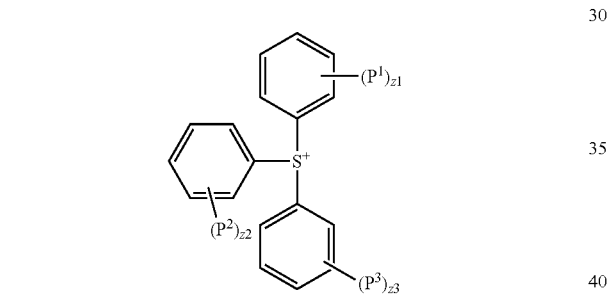
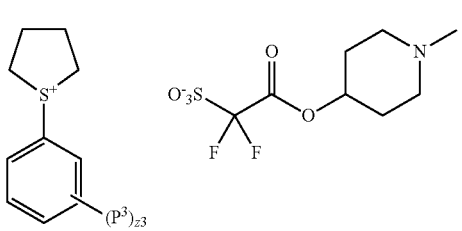
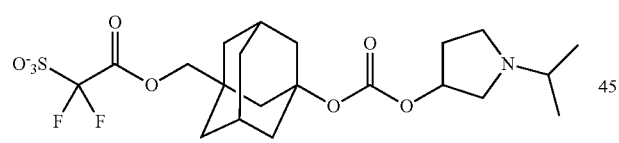
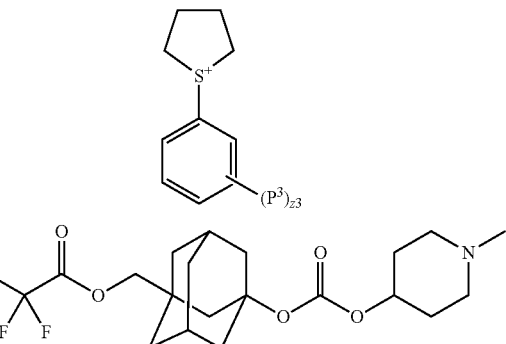
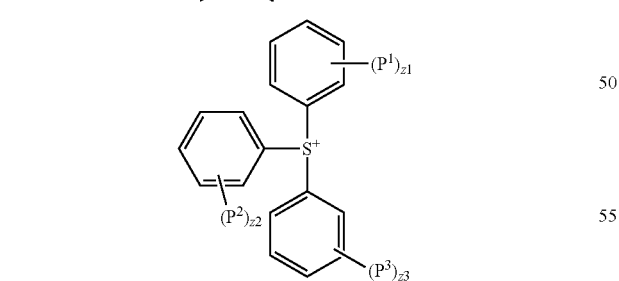
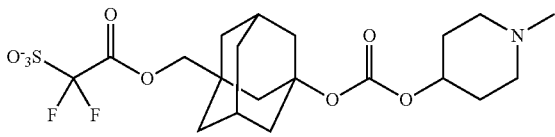
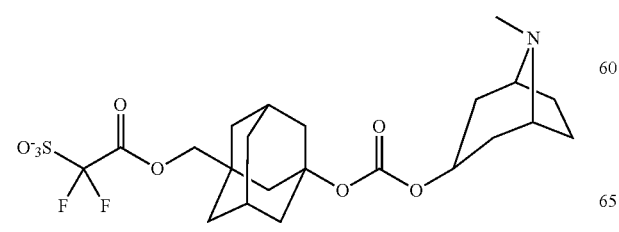
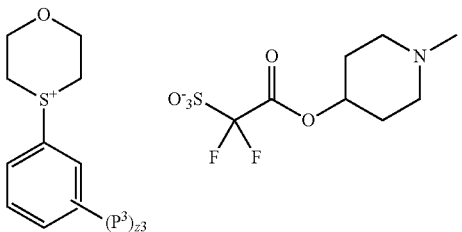

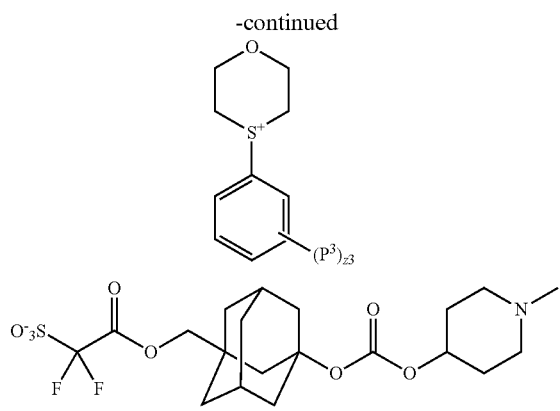
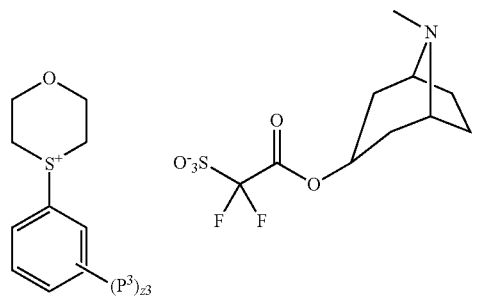
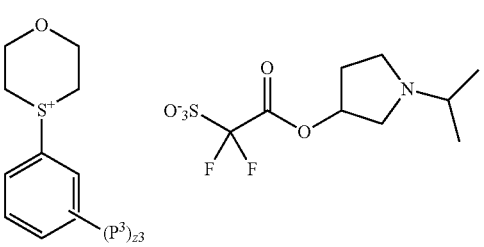
Further, the salts below are more preferable.
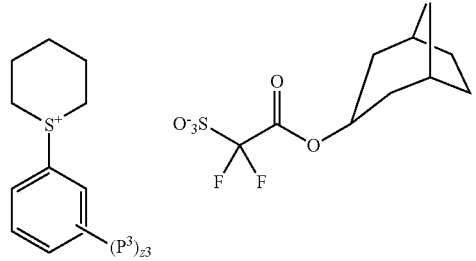
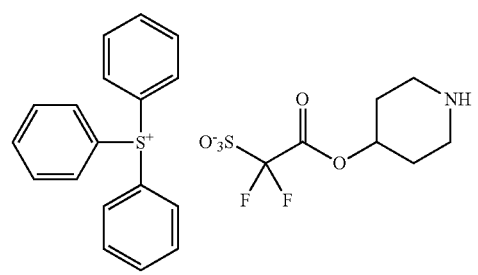
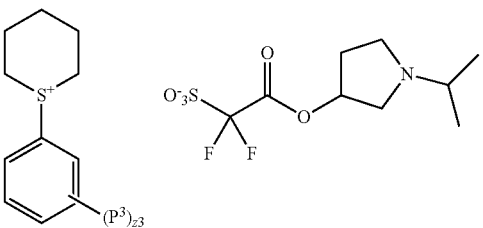
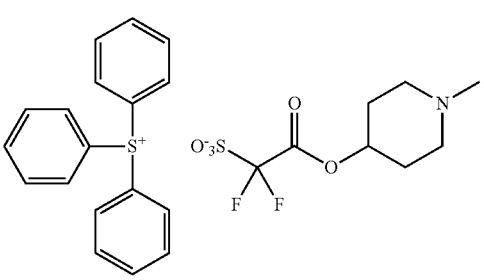
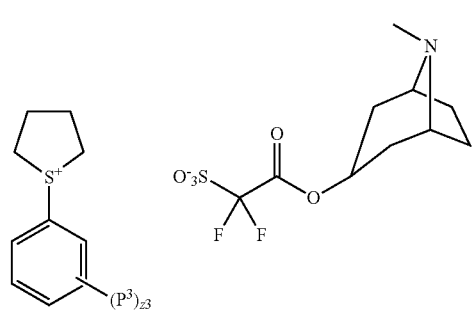
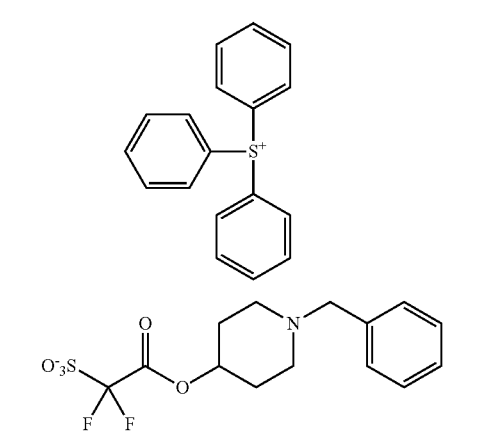
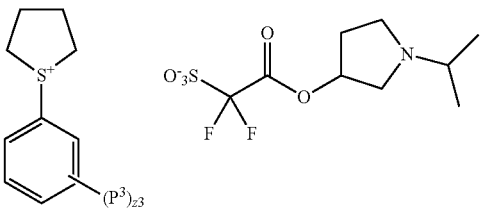

33
-continued
34
-continued
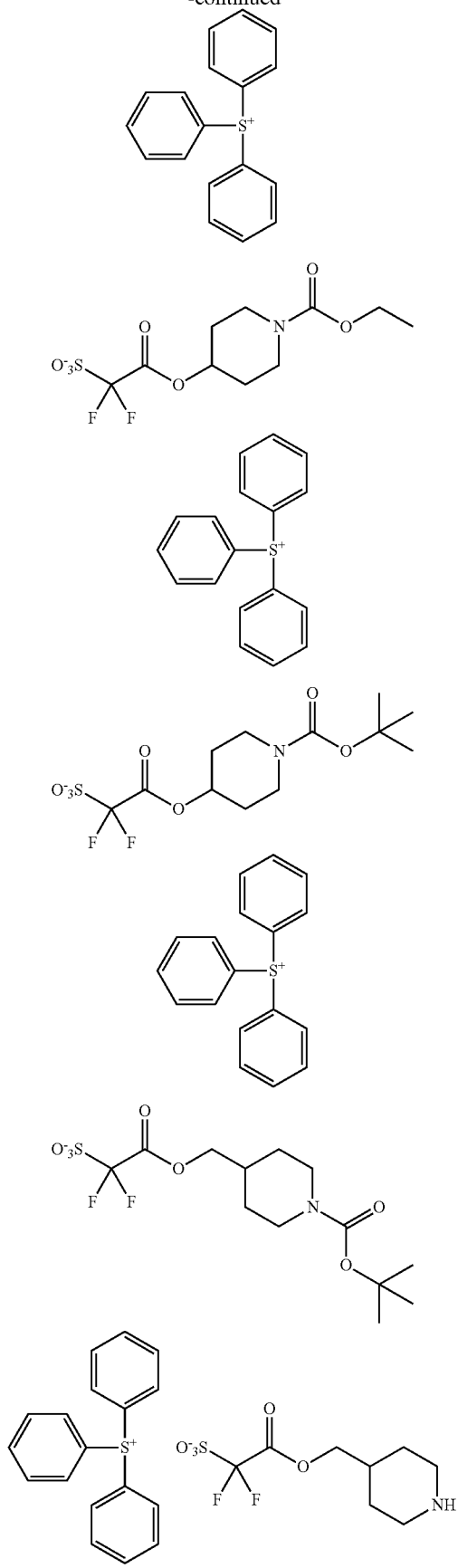
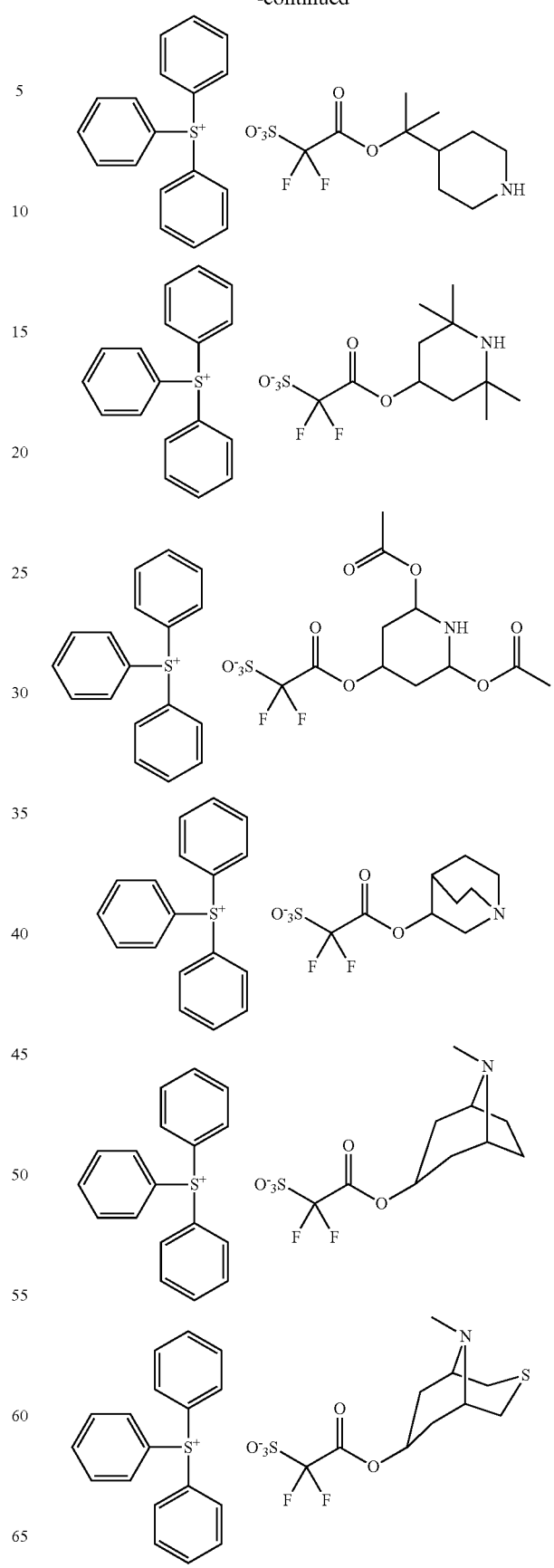

35
-continued
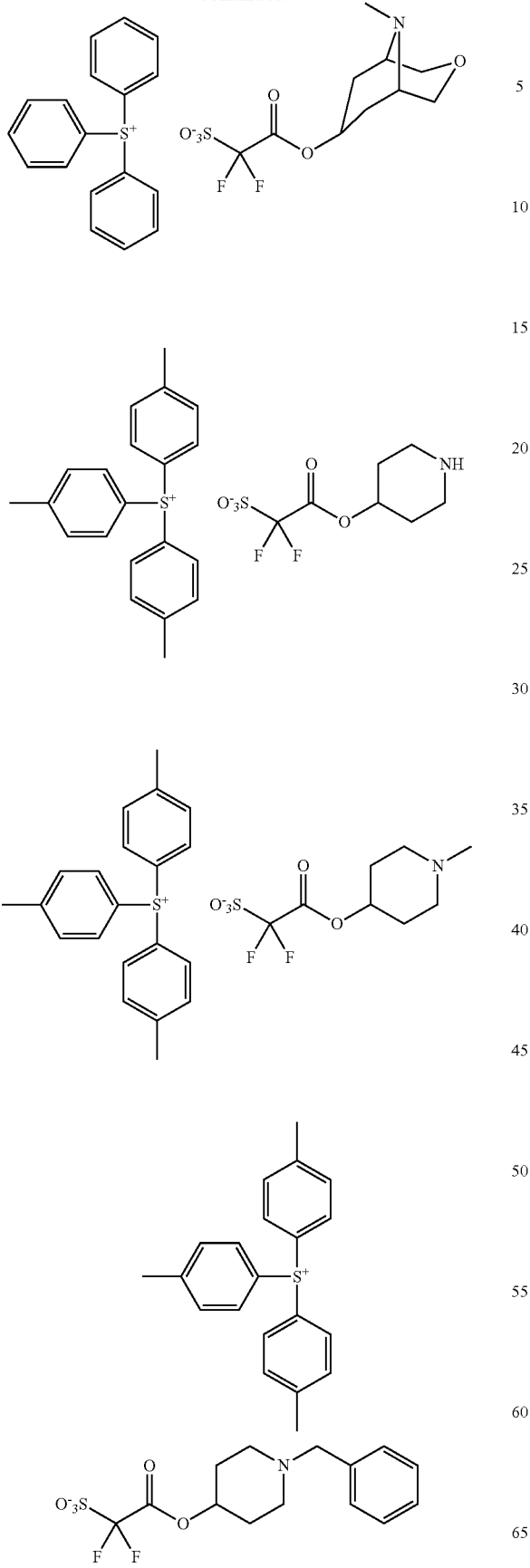
36
-continued
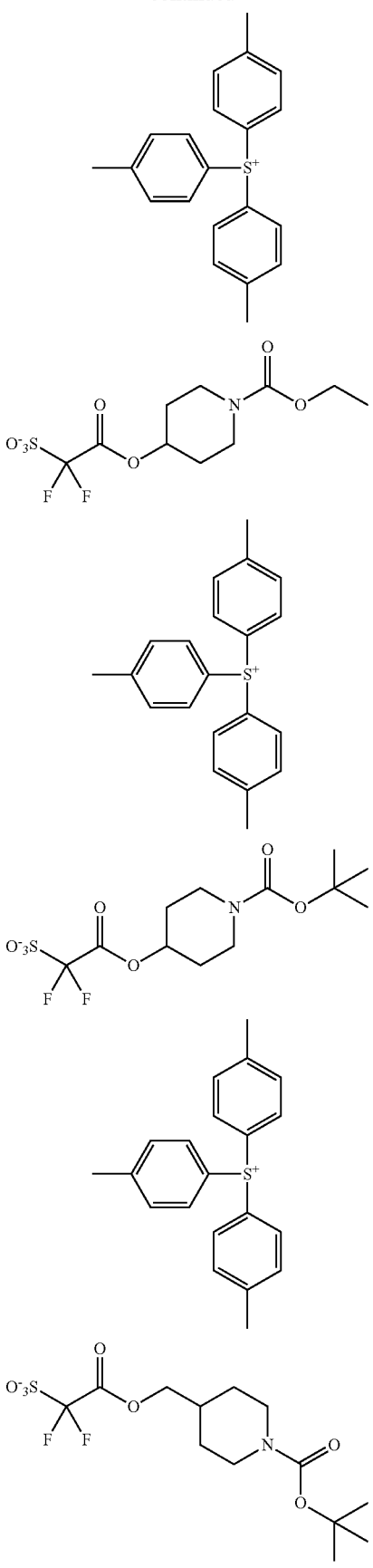

37
-continued
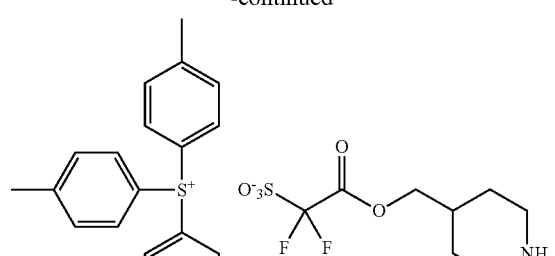
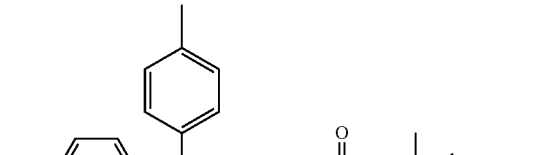
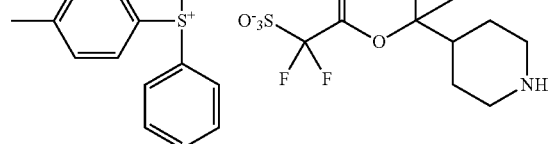
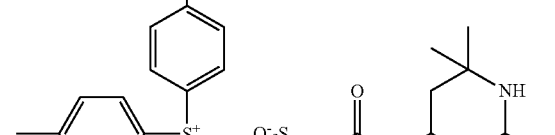
38
-continued
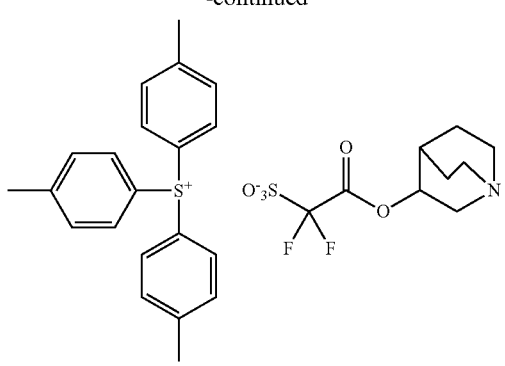
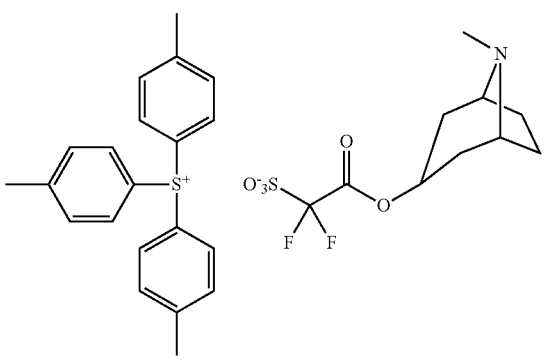
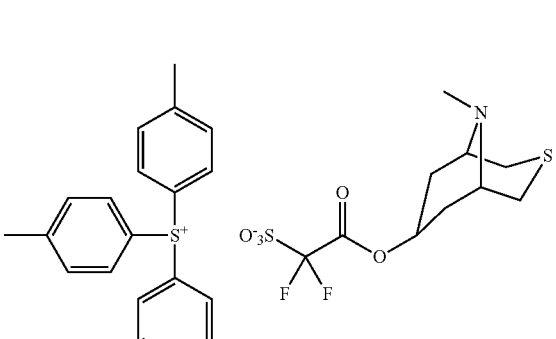
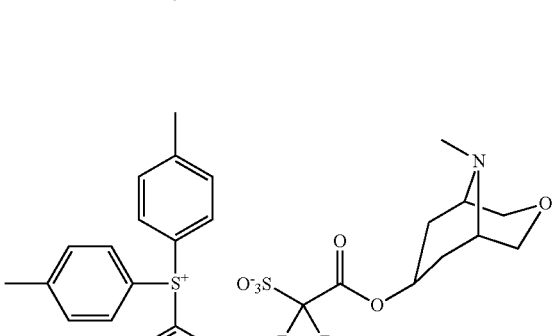

-continued

41
-continued
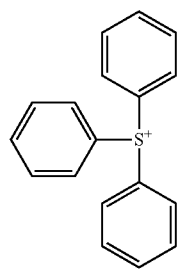
42
-continued
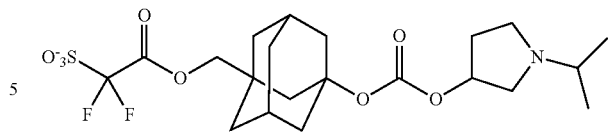
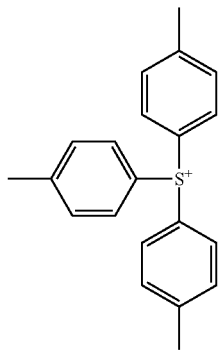
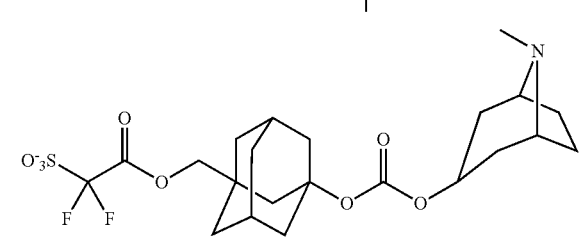
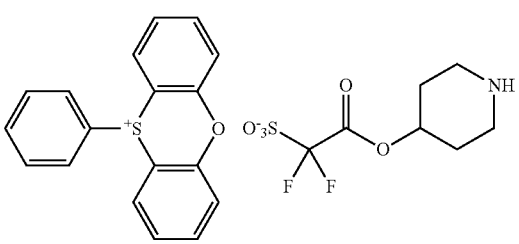
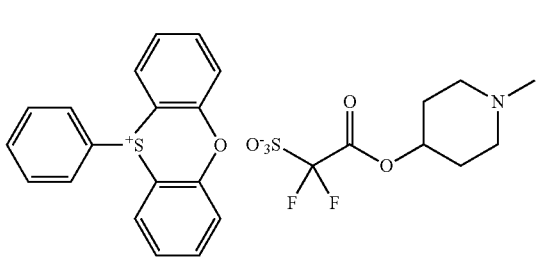
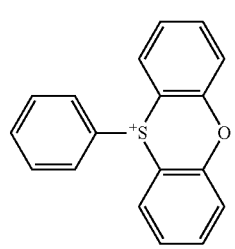
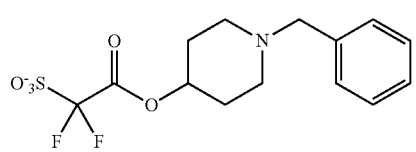

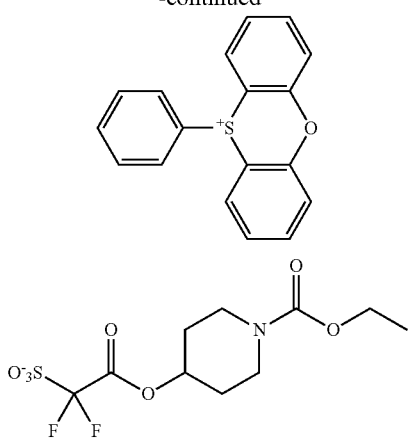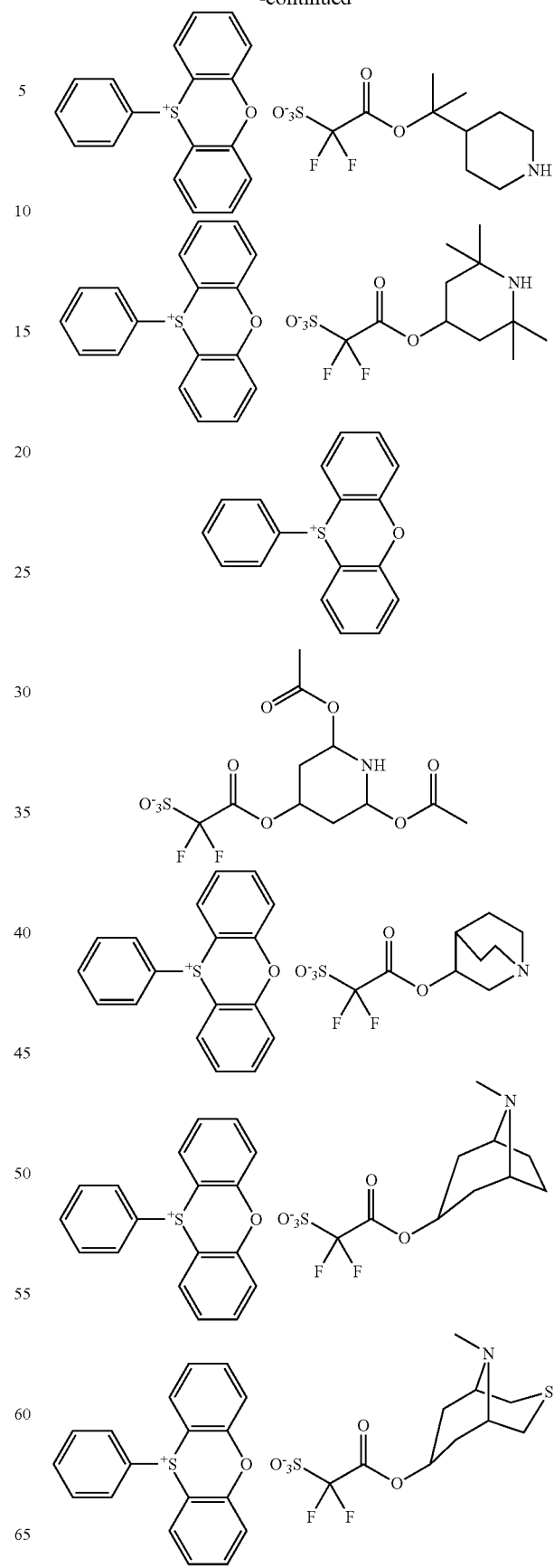

45
-continued
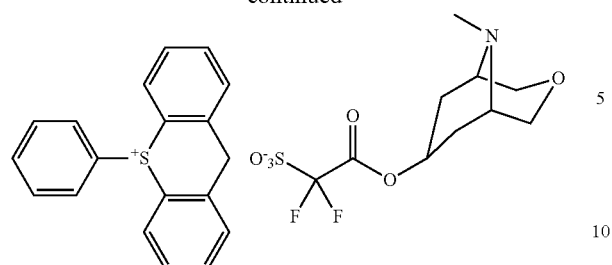
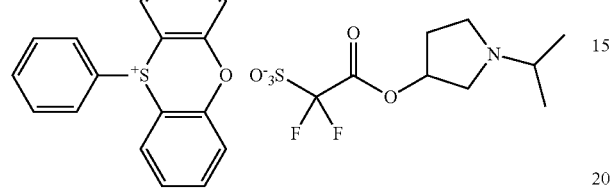
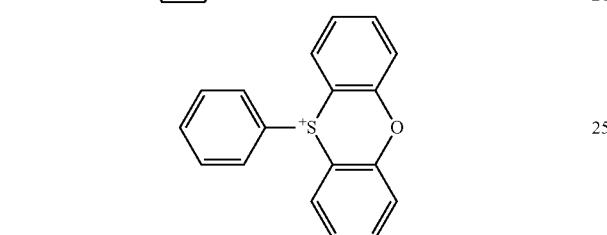
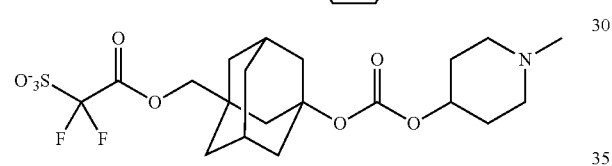
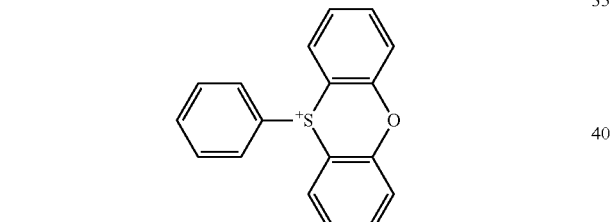
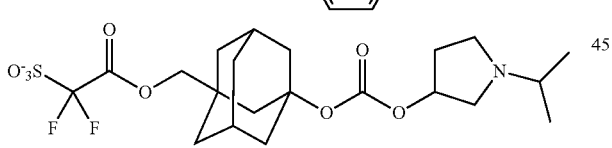
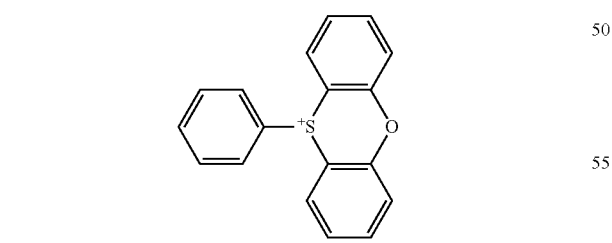
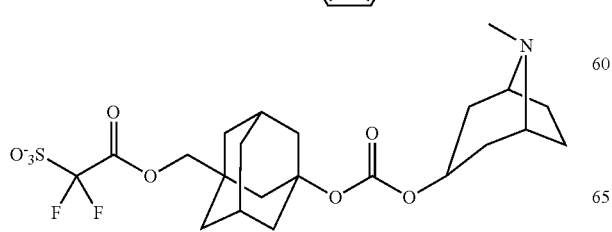
46
-continued
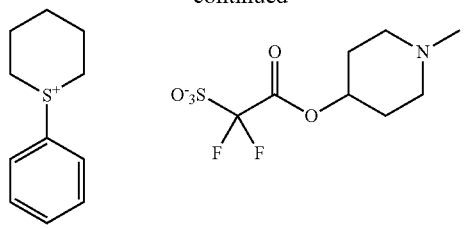
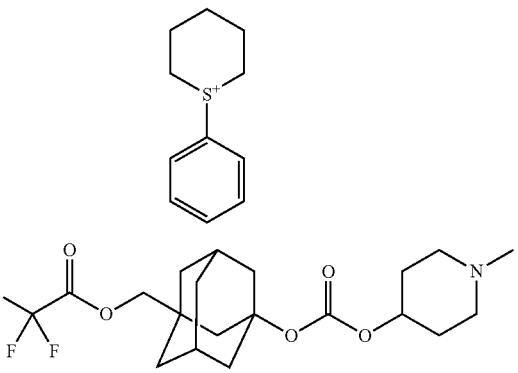
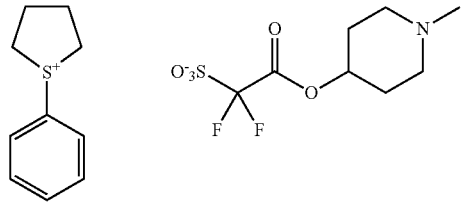
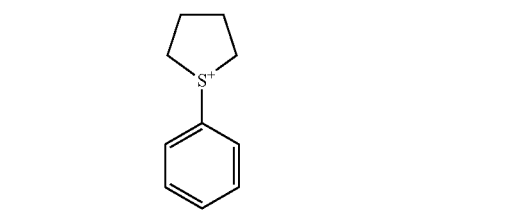
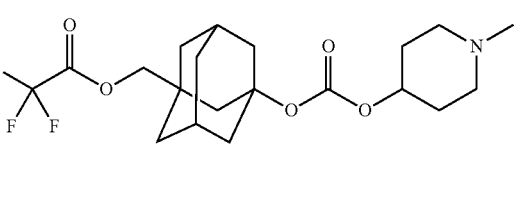
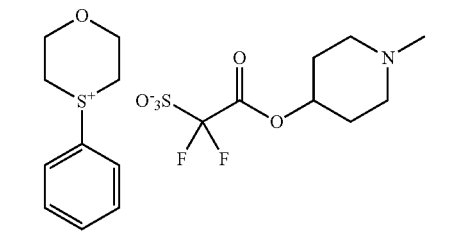

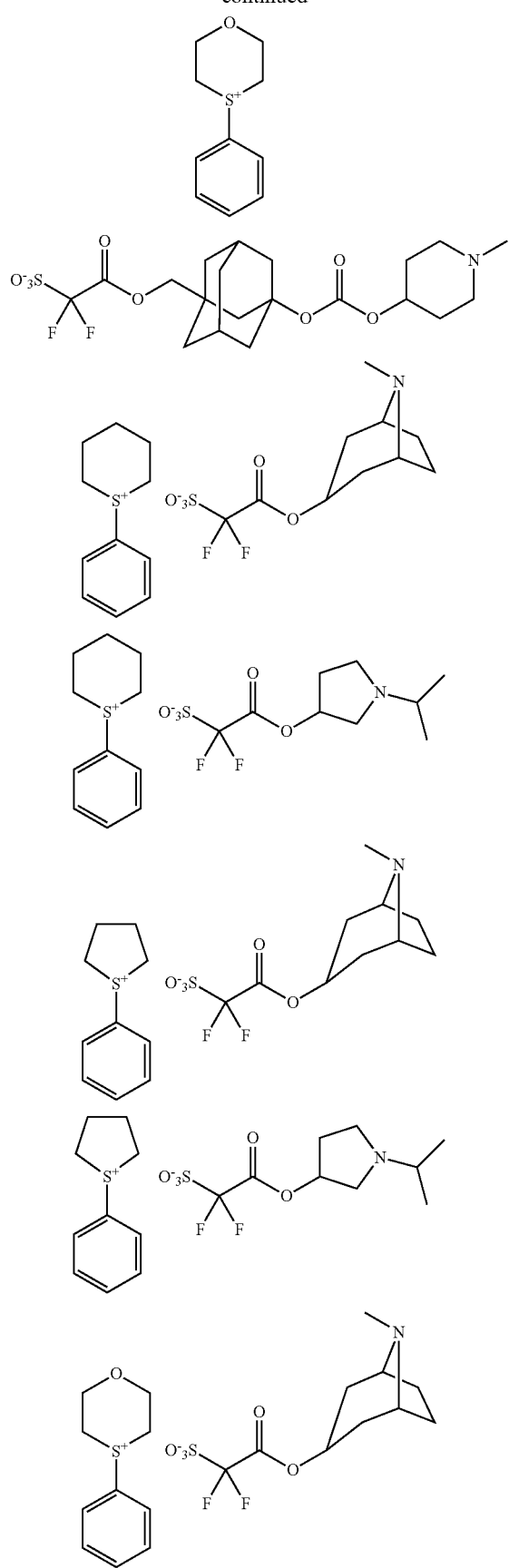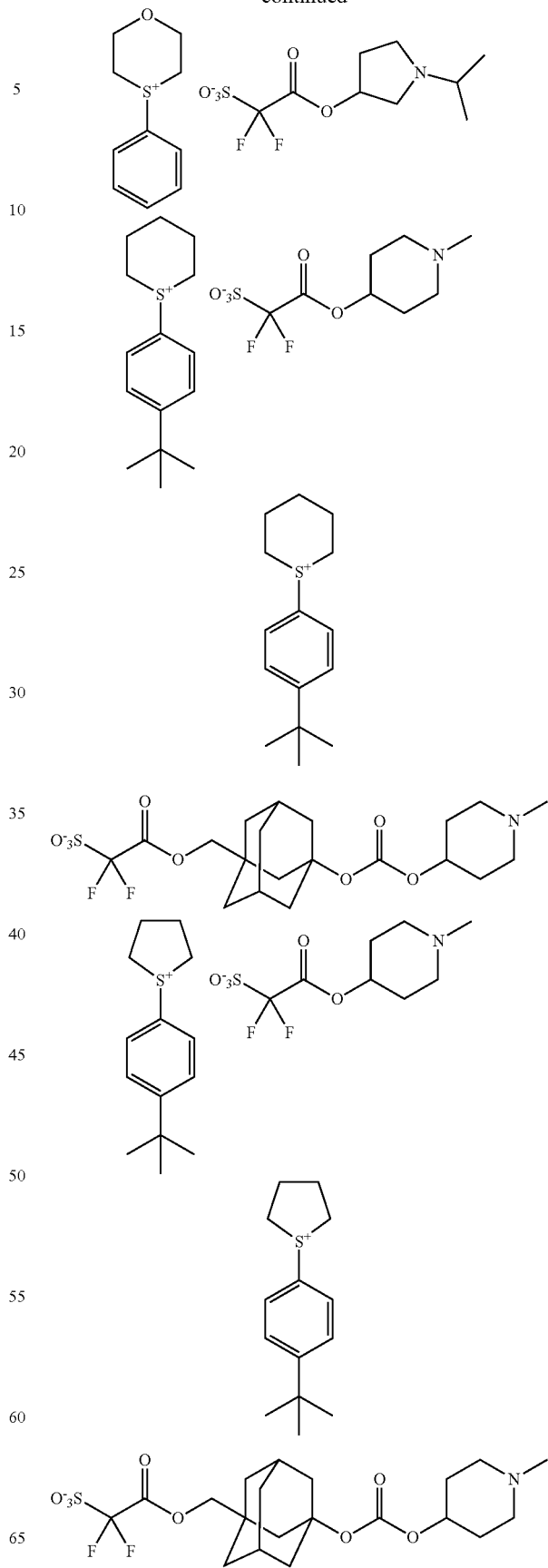

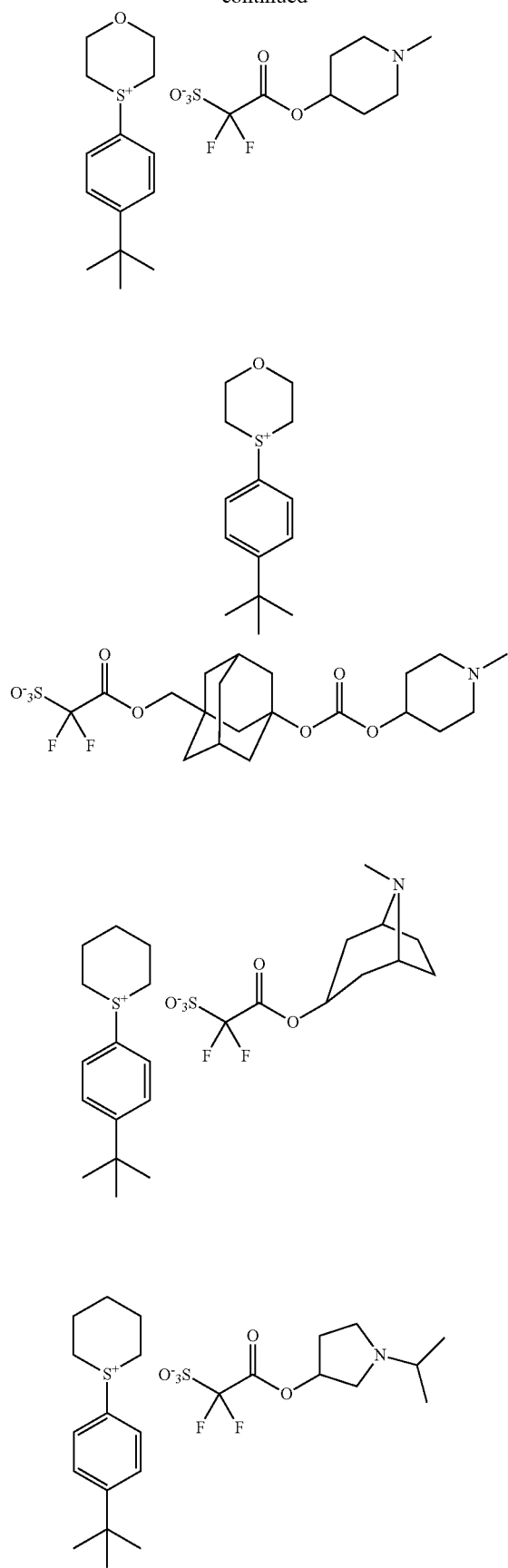
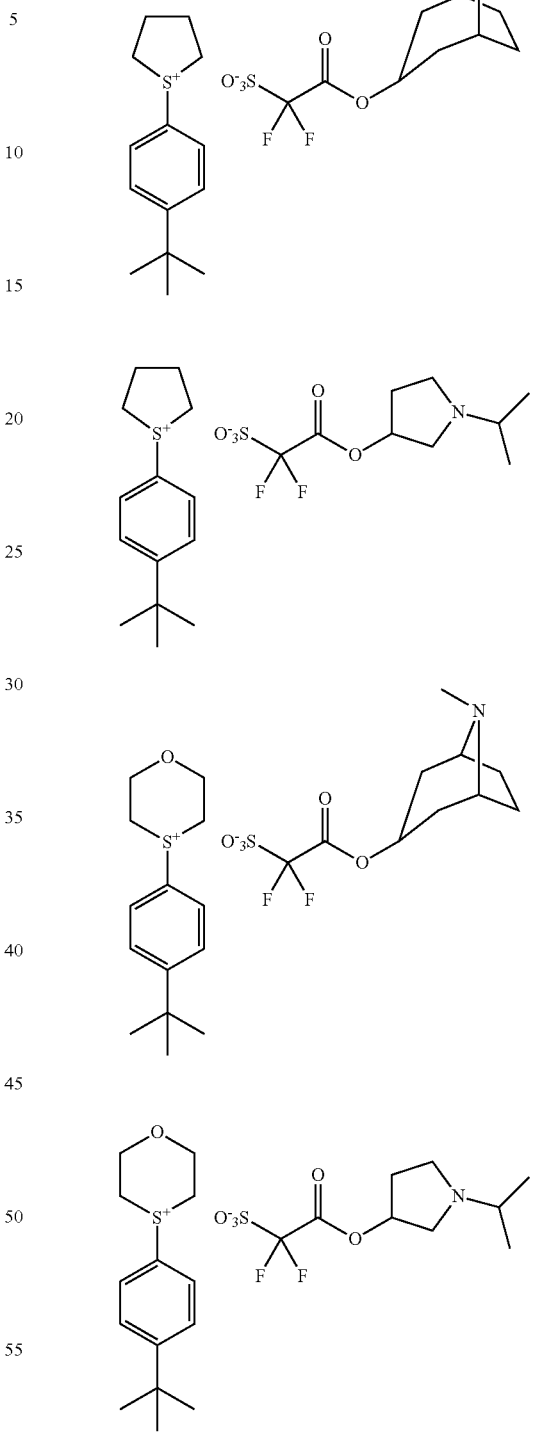
The salt represented by the formula (I) can be produced by a known method in the field.
For example, a salt represented by the formula (Ia) in which $L^1$ of the salt represented by the formula (I) is —CO—O— can be obtained by reacting a salt represented by the formula (Ia-1) with a compound represented by the formula (Ia-2) in a solvent.

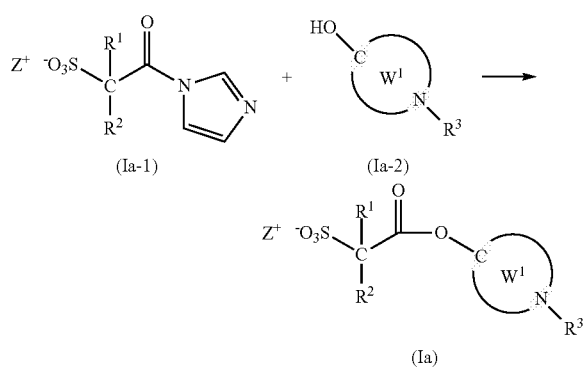

wherein $R^1$ to $R^3$, $Z^+$, and $W^1$ represent the same meaning as described above.

Examples of the solvent include chloroform.

Example of the compound represented by the formula (Ia-2) include 4-hydroxy-1-methylpiperidine, 4-hydroxy-2,2,6,6-tetramethylpiperidine and tropine.

The compound represented by the formula (Ia-1) can be obtained by reacting a salt represented by the formula (Ia-4) with a compound represented by the formula (Ia-3).

The compound represented by the formula (Ia-3) can be synthesized according to the method described in JP-2008-127367-A.

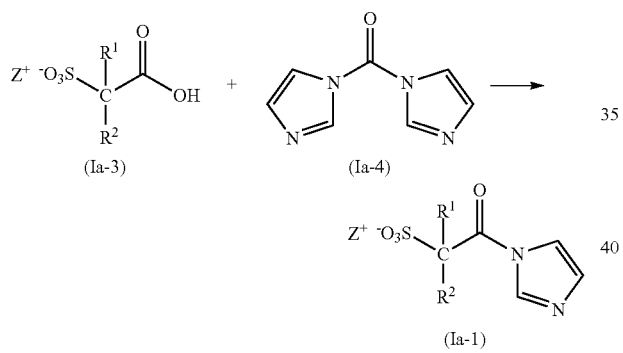

wherein $R^1$ to $R^2$ and $Z^+$ represent the same meaning as described above.

<Acid Generator>

An acid generator contains the salt represented by the formula (I). When the salt (I) is used as the acid generator, the salt may be used singly or in combination with two or more. The acid generator of the present invention can further include a known salt other than the salt represented by the formula (I), for example, a salt which has the cation contained in the salt represented by the formula (I) and a known anion, or a salt which has the anion contained in the salt represented by the formula (I) and a known cation.

When the acid generator of the present invention contains the salt represented by the formula (I) and the known salt other than the salt represented by the formula (I), the salt represented by the formula (I) and the known salt other than the salt represented by the formula (I) is preferably, for example, 5:95 to 95:5 (by weight), more preferably 10:90 to 90:10 and still more preferably 15:85 to 85:15.

<Resist Composition>

A resist composition of the present invention includes the acid generator described above and a resin.

<Acid Generator>

The resist composition of the present invention preferably contains 1 part by mass or more (more preferably 3 parts by mass or more), and 30 parts by mass or less (more preferably 25 parts by mass or less) of the acid generator with respect to 100 parts by mass of the resin (A) described below.

When the acid generator contains the salt represented by the formula (I) and the known salt other than the salt represented by the formula (I), the total content thereof is generally 1 part by mass or more (more preferably 3 parts by mass or more), and 40 parts by mass or less (more preferably 35 parts by mass or less) with respect to 100 parts by mass of the resin (A) described below.

<Resin (Hereinafter May be Referred to as "Resin (A)")>

The resin (A) is a resin which becomes soluble in an alkali aqueous solution by the action of the acid. The resin which becomes soluble in an alkali aqueous solution by the action of the acid can be produced by polymerizing a monomer having an acid-labile group (hereinafter may be referred to as "the monomer having an acid-labile group (a1)"). The phrase "the resin becomes soluble in an alkali aqueous solution by the action of the acid" means that the resin is insoluble or poorly soluble in aqueous alkali solution before contacting with an acid but becomes soluble in aqueous alkali solution after contacting with an acid. The monomer having an acid-labile group (a1) may be used singly or mixture of two or more.

<Monomer Having an Acid-Labile Group (a1)>

The "acid-labile group" means a group in which an elimination group is cleaved by contacting with an acid resulting in forming a hydrophilic group such as a carboxy or a hydroxy group.

Examples of the acid-labile group include, for example, an alkoxycarbonyl group represented by the formula (1) in which an oxygen atom bonds a tertiary carbon atom. Hereinafter the group represented by the formula (1) may refer to as an "acid-labile group (1)".

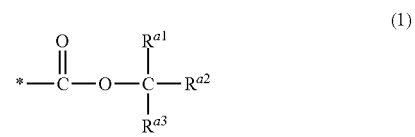

wherein $R^{a1}$ to $R^{a3}$ independently represent a $C_1$ to $C_8$ aliphatic hydrocarbon group or a $C_3$ to $C_{20}$ saturated cyclic hydrocarbon group, or $R^{a1}$ and $R^{a2}$ may be bonded together to form a $C_3$ to $C_{20}$ ring, * represents a single bond (hereinafter the same meaning may apply).

Examples of the aliphatic hydrocarbon group and the saturated cyclic hydrocarbon group include the same examples defined above.

In the formula (1), the saturated cyclic hydrocarbon group preferably has 1 to 16 carbon atoms.

When $R^{a1}$ and $R^{a2}$ are bonded together to form a ring, examples of the group —$C(R^{a1})(R^{a2})(R^{a3})$ include a group below.

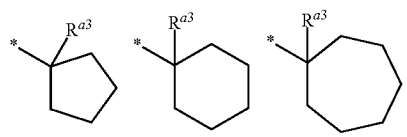

-continued

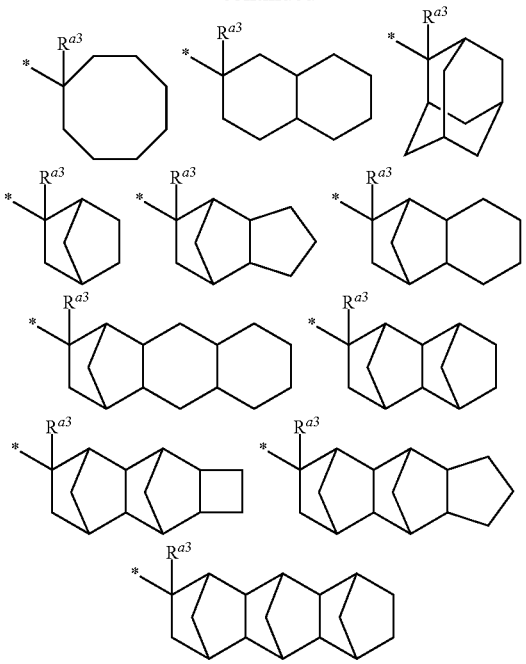

The ring preferably has 3 to 12 carbon atoms.

Examples of the acid-labile group include, for example, 1,1-dialkylalkoxycarbonyl group (a group in which $R^{a1}$ to $R^{a3}$ are alkyl groups, preferably tert-butoxycarbonyl group, in the formula (1)), 2-alkyladamantane-2-yloxycarbonyl group (a group in which $R^{a1}$, $R^{a2}$ and a carbon atom forms adamantyl group, and $R^{a3}$ is alkyl group, in the formula (1)), and 1-(adamantane-1-yl)-1-alkylalkoxycarbonyl group (a group in which $R^{a1}$ and $R^{a2}$ are alkyl group, and $R^{a3}$ is adamantyl group, in the formula (1)).

Examples of the acid-labile group when the hydrophilic group is a hydroxy group include a group in which a hydrogen atom of the hydroxy group is replaced with an organic group and resulting in having an acetal structure. Among such the acid-labile group, preferred examples of the acid-labile group include, for example, a group represented by the formula (2) below. Hereinafter the group represented by the formula (2) may refer to as an "acid-labile group (2)".

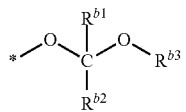

(2)

wherein $R^{b1}$ and $R^{b2}$ independently represent a hydrogen atom or a $C_1$ to $C_{12}$ hydrocarbon group, $R^{b3}$ represents a $C_1$ to $C_{20}$ hydrocarbon group, or $R^{b2}$ and $R^{b3}$ may be bonded together with a carbon atom and an oxygen atom bonded to $R^{b2}$ and $R^{b3}$ to form a $C_3$ to $C_{20}$ ring, respectively. One or more —$CH_2$— contained in the hydrocarbon group and the ring may be replaced by —O—, —S— or —CO—, * represents a single bond.

The hydrocarbon group of $R^{b1}$ to $R^{b3}$ includes, for example, any of an aliphatic hydrocarbon group, a saturated cyclic hydrocarbon group and an aromatic hydrocarbon group. Examples of the aliphatic hydrocarbon group, the saturated cyclic hydrocarbon group and the aromatic hydrocarbon group here include the same examples defined above. Examples of the ring which is formed by bonding with $R^{b2}$ and $R^{b3}$ include the same ring which is formed by bonding with $R^{a1}$ and $R^{a2}$.

At least one of $R^{b1}$ and $R^{b2}$ is preferably a hydrogen atom.

Specific examples of the acid-labile group (2) include a group below.

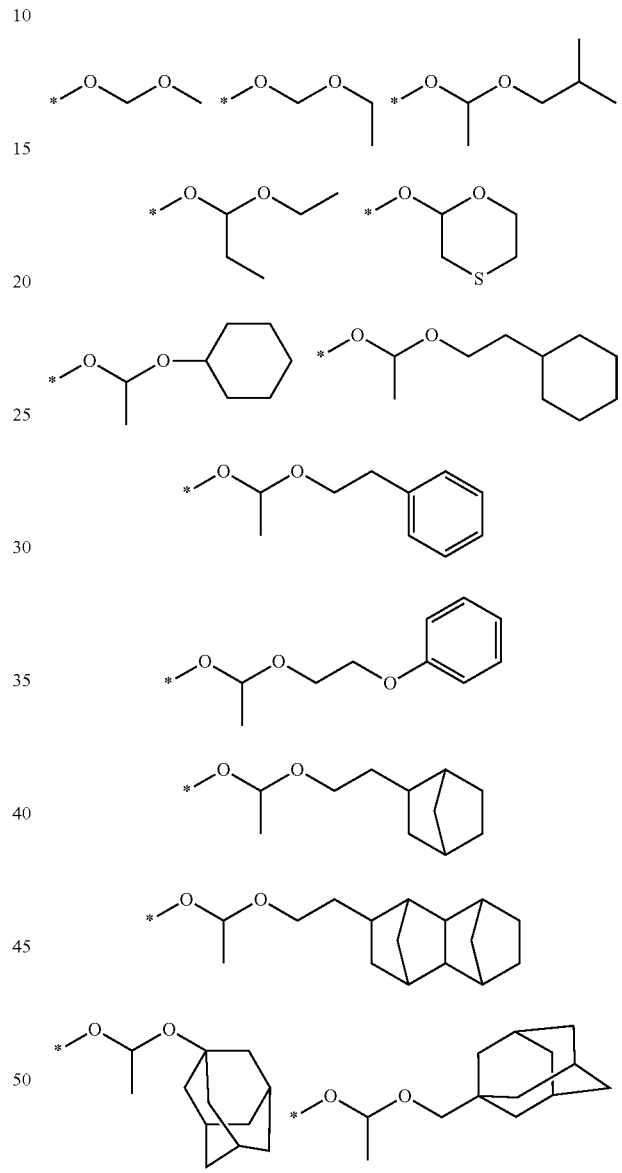

The monomer having an acid-labile group (a1) is preferably a monomer having an acid-labile group and a carbon-carbon double bond, and more preferably a (meth)acrylic monomer having an acid-labile group. Here, (meth)acrylic monomer means acrylic monomer and/or methacrylic monomer.

Among the (meth)acrylic monomer, it is preferably a monomer having a $C_5$ to $C_{20}$ saturated cyclic hydrocarbon group. When a resin which can be obtained by polymerizing monomers having bulky structure such as the saturated cyclic hydrocarbon group, the resist composition having excellent resolution tend to be obtained.

Examples of the saturated cyclic hydrocarbon group include the same examples defined above.

Among the (meth)acrylic monomer having the acid-labile group and the saturated cyclic hydrocarbon group, a monomer having an adamantyl group represented by the formula (a-1) and a monomer having a cyclohexyl group represented by the formula (a-2) are preferable. These may be used singly or mixture of two or more.

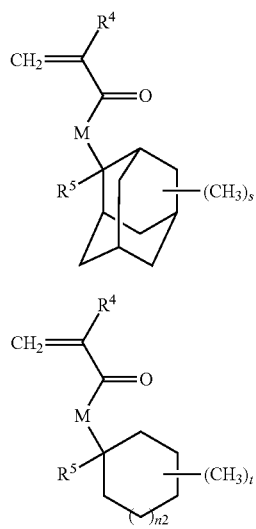

wherein M independently represents —O— or —O—$(CH_2)_k$—CO—O—, k represents an integer 1 to 7, the group —O— and other groups of M is represented so that the left side of the group bonds to —CO— of the formula (a-1) and the formula (a-2), and the right side of the group bonds to adamantyl or cyclohexyl group, respectively;

$R^4$ independently represents a hydrogen atom or a methyl group;

$R^5$ independently represents a $C_1$ to $C_8$ aliphatic hydrocarbon group or a $C_3$ to C10 saturated cyclic hydrocarbon group; and s represents an integer 0 to 14;

t represents an integer 0 to 10; and n2 represents an integer 0 to 3.

In the formula (a-1) and the formula (a-2), M is preferably —O— or —O—$(CH_2)_f$—CO—O—, here f represents an integer of 1 to 4, and more preferably —O—.

$R^4$ is preferably a methyl group.

The aliphatic hydrocarbon group of $R^5$ has preferably 6 or less carbon atoms. The saturated cyclic hydrocarbon group has preferably 8 or less carbon atoms, and more preferably 6 or less carbon atoms.

s is preferably an integer of 0 to 3, and more preferably 0 or 1.

t is preferably an integer of 0 to 3, and more preferably 0 or 1.

n2 is preferably 0 or 1.

Examples of the monomer having an adamantyl group (a-1) include a group below. Among these, 2-methyladamantane-2-yl (meth)acrylate, 2-ethyladamantane-2-yl (meth)acrylate and 2-isopropyladamantane-2-yl (meth)acrylate are preferable, and their methacrylate forms are more preferable.

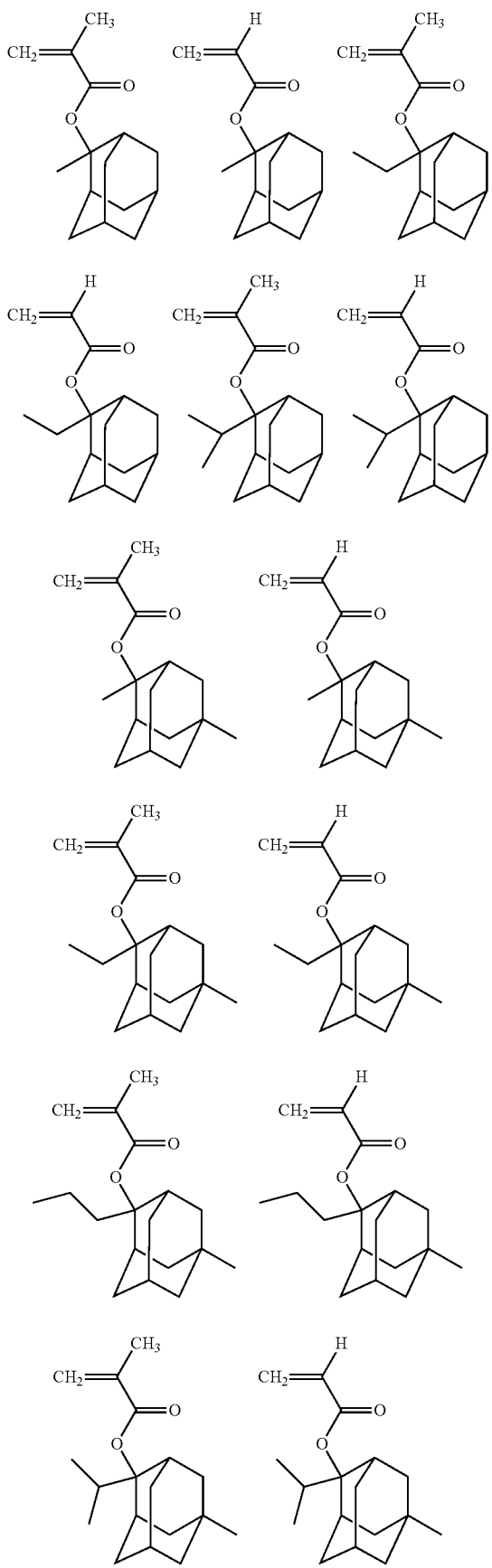

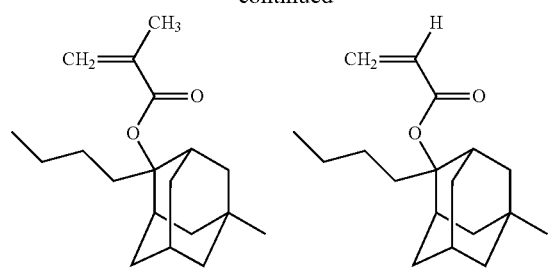
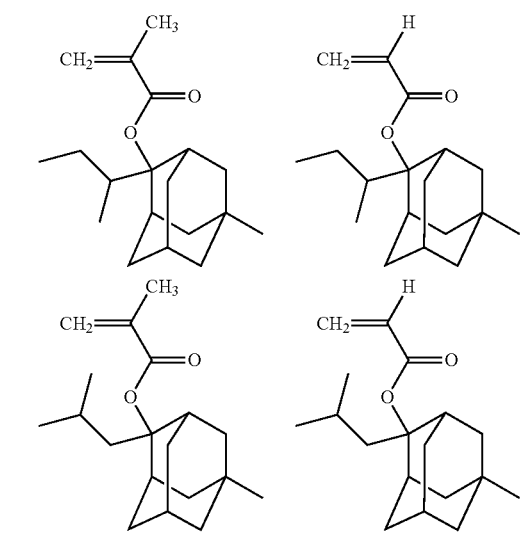
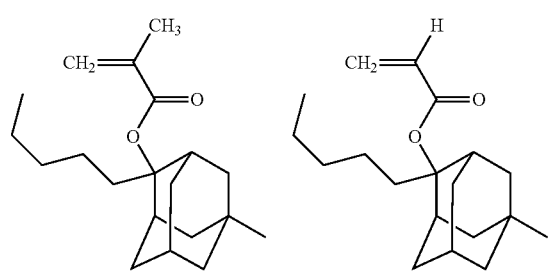
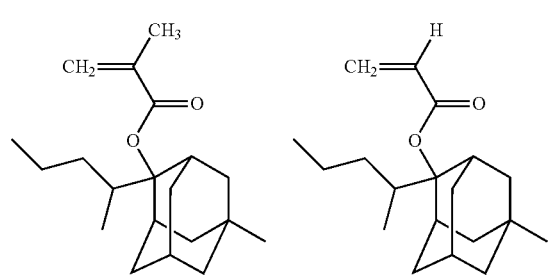
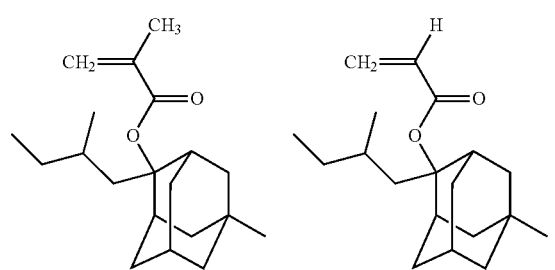
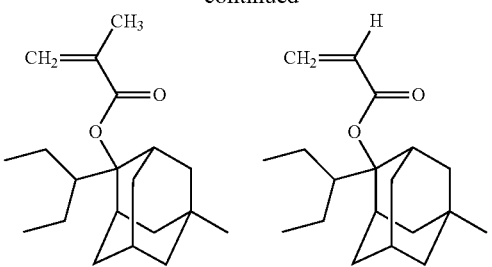
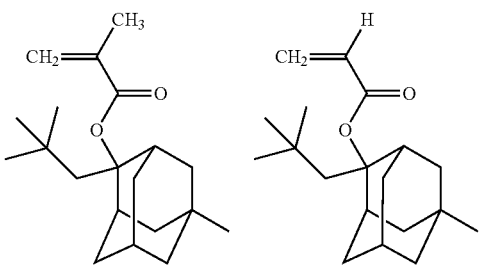
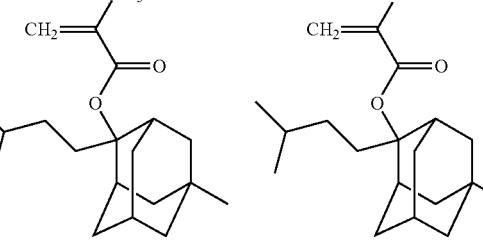
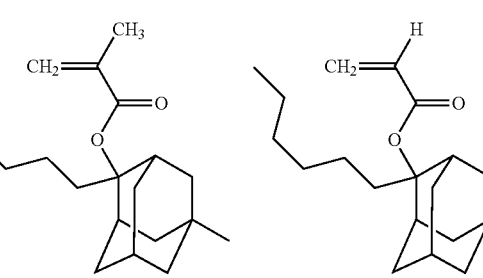
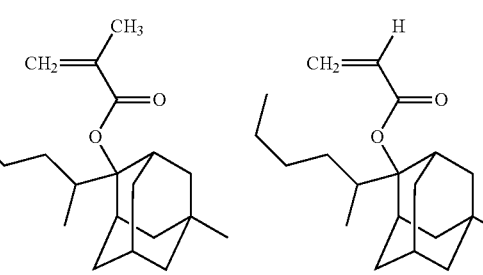
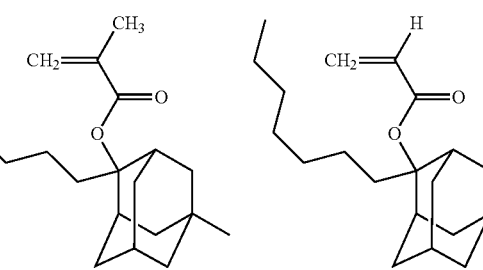

-continued
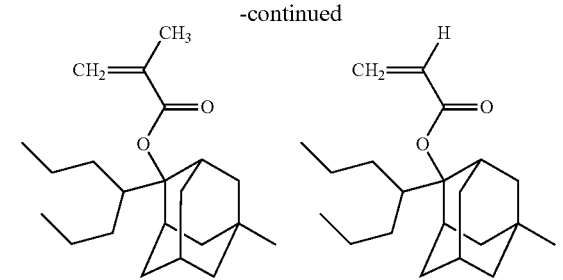
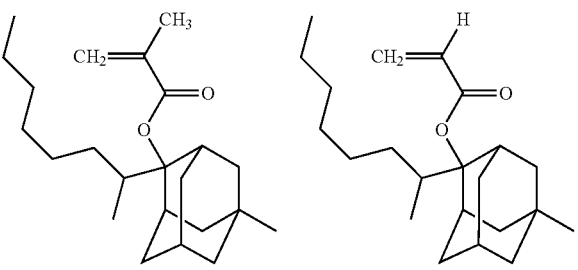
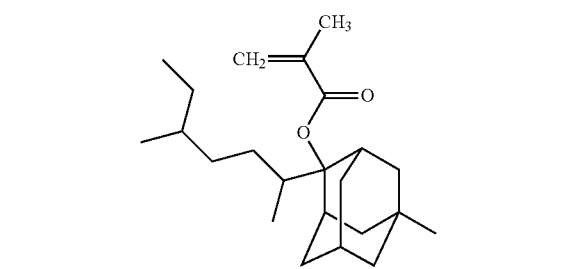
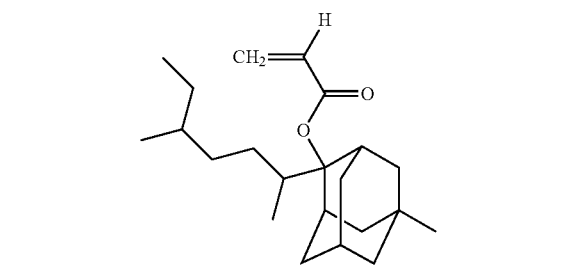
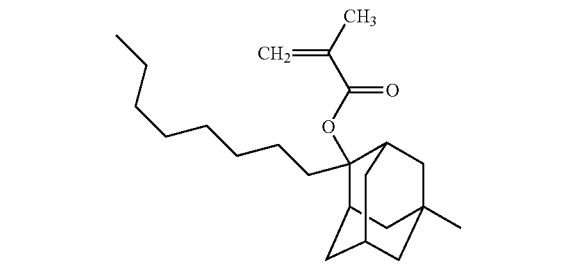
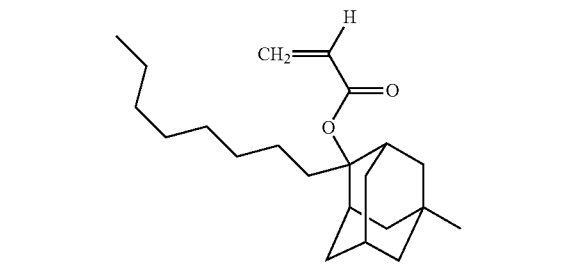
-continued
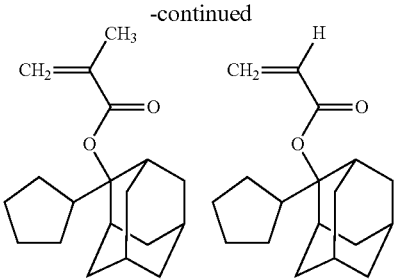
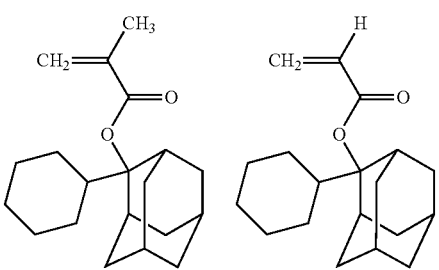
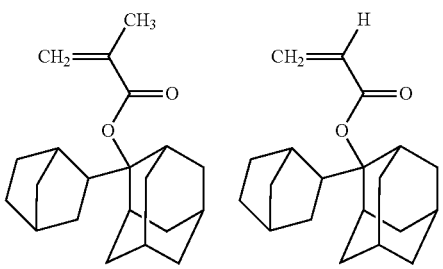
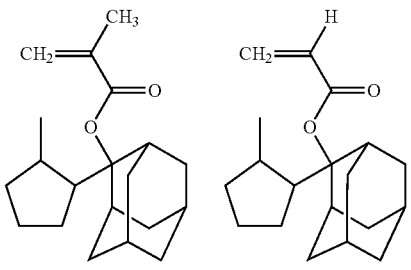
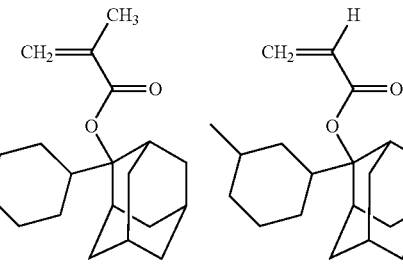
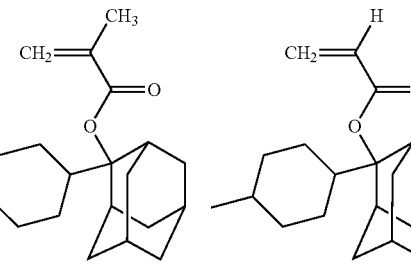

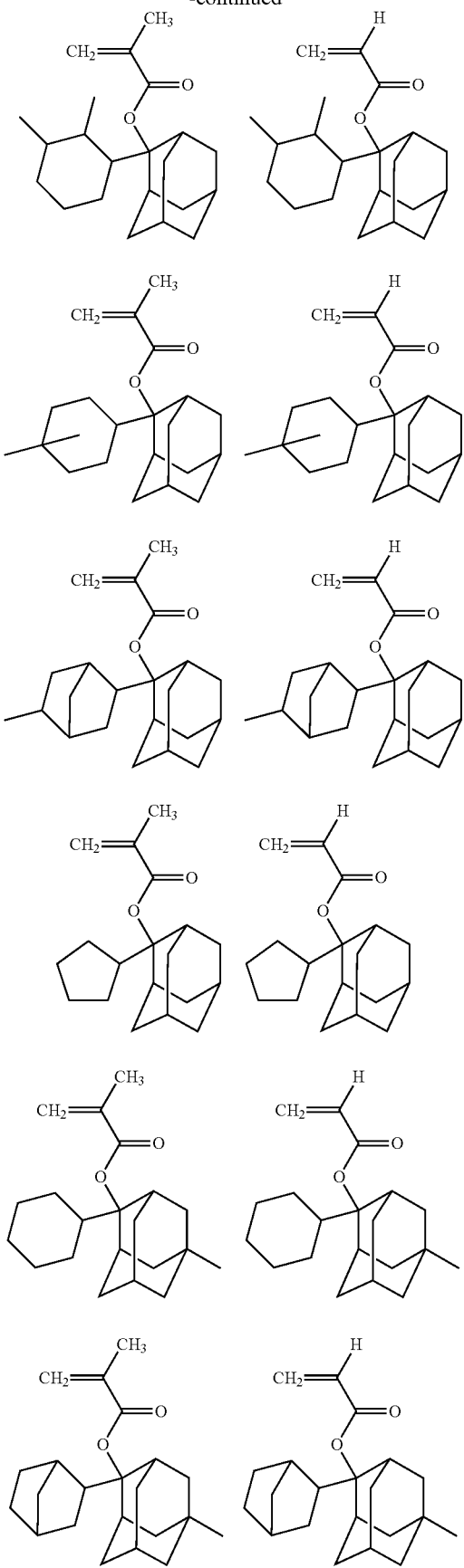
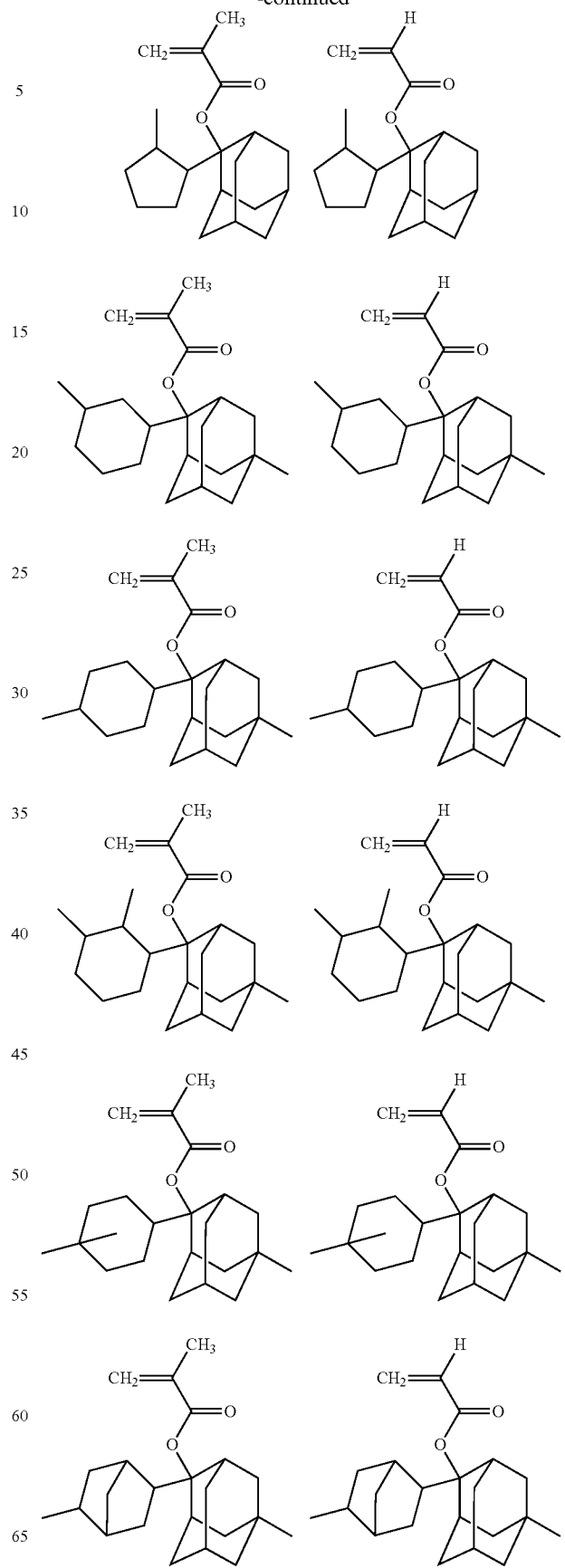

-continued

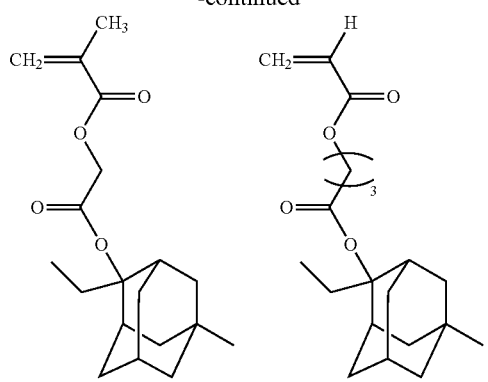
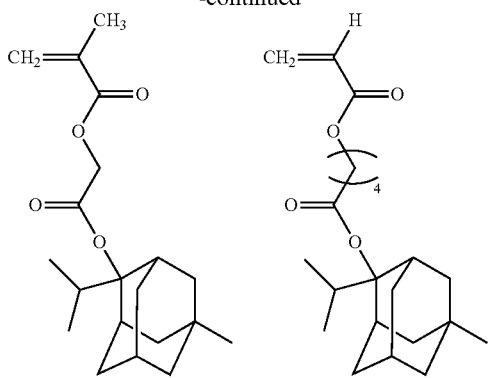
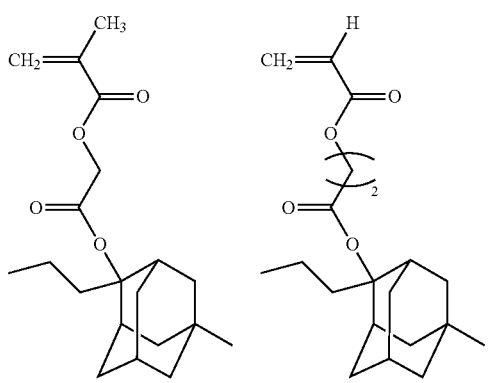
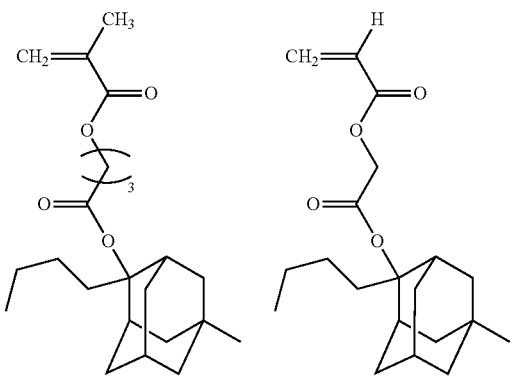
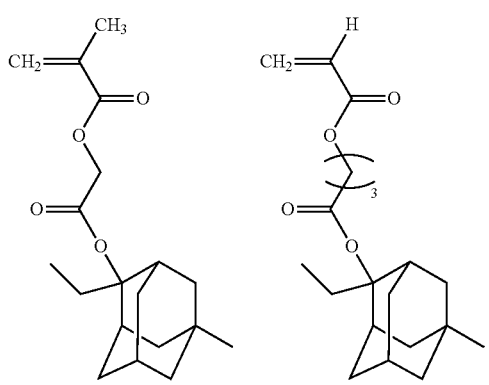
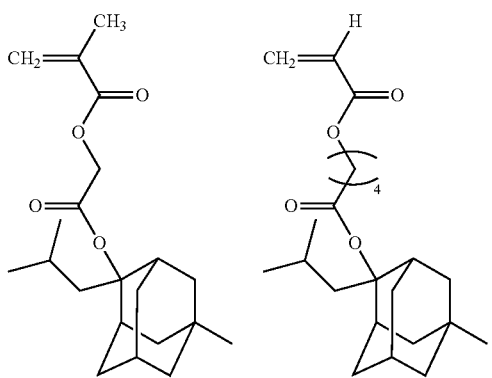
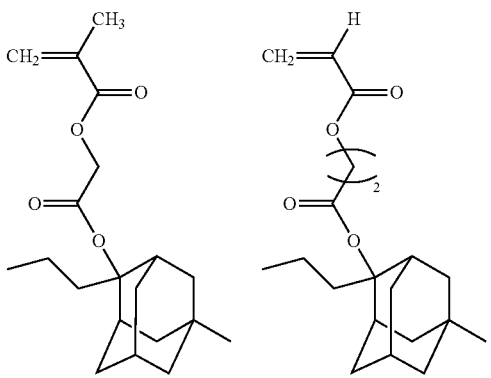
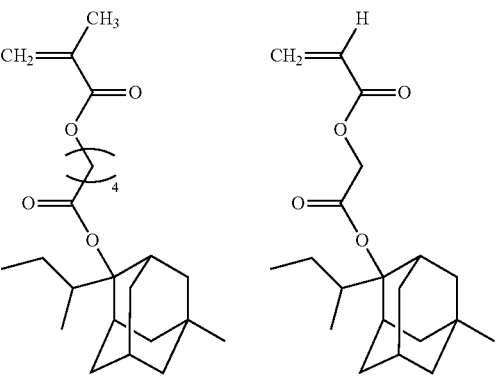

67
-continued
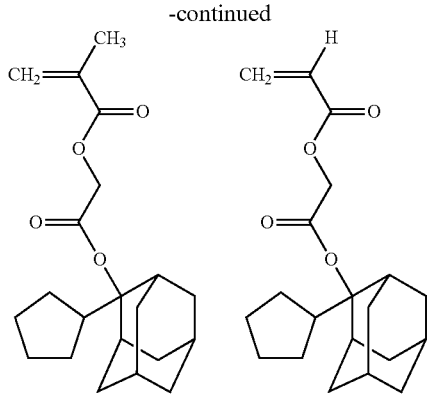
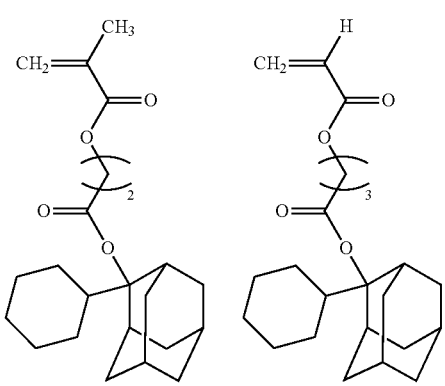
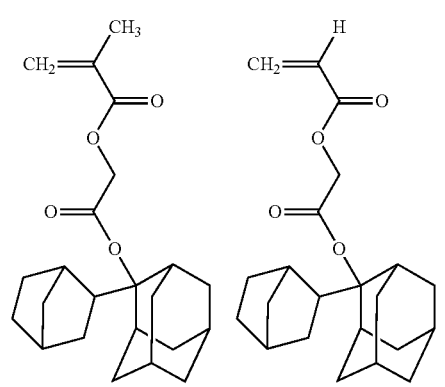
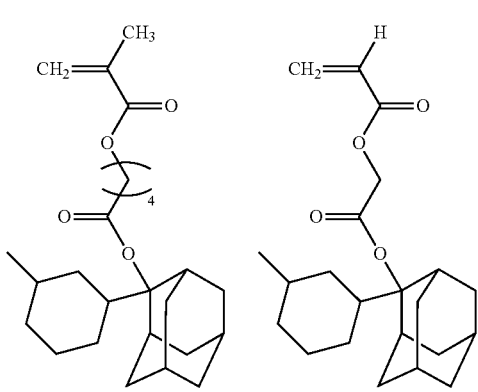
68
-continued
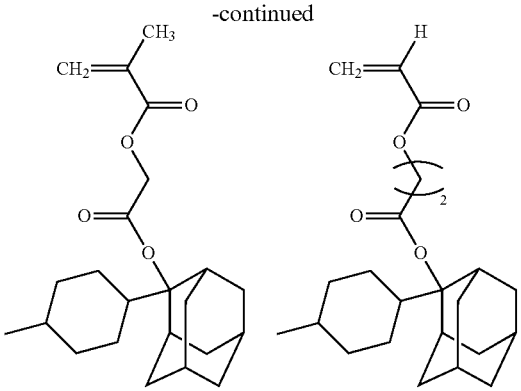
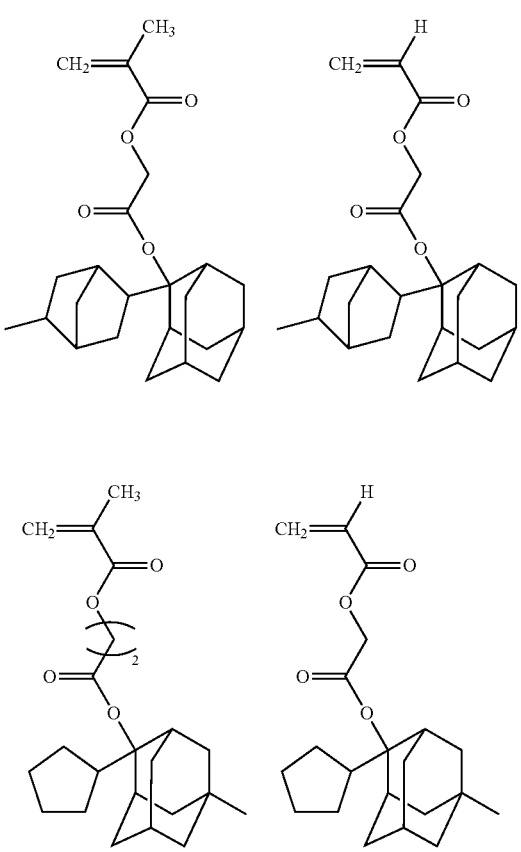
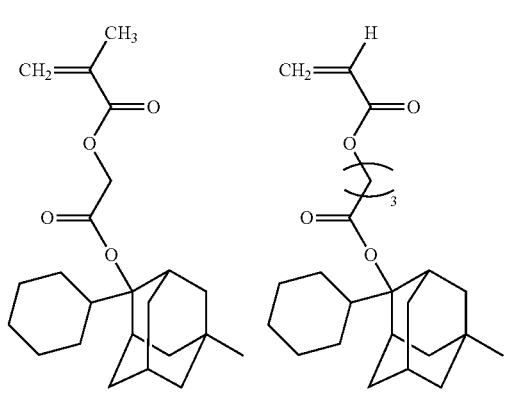

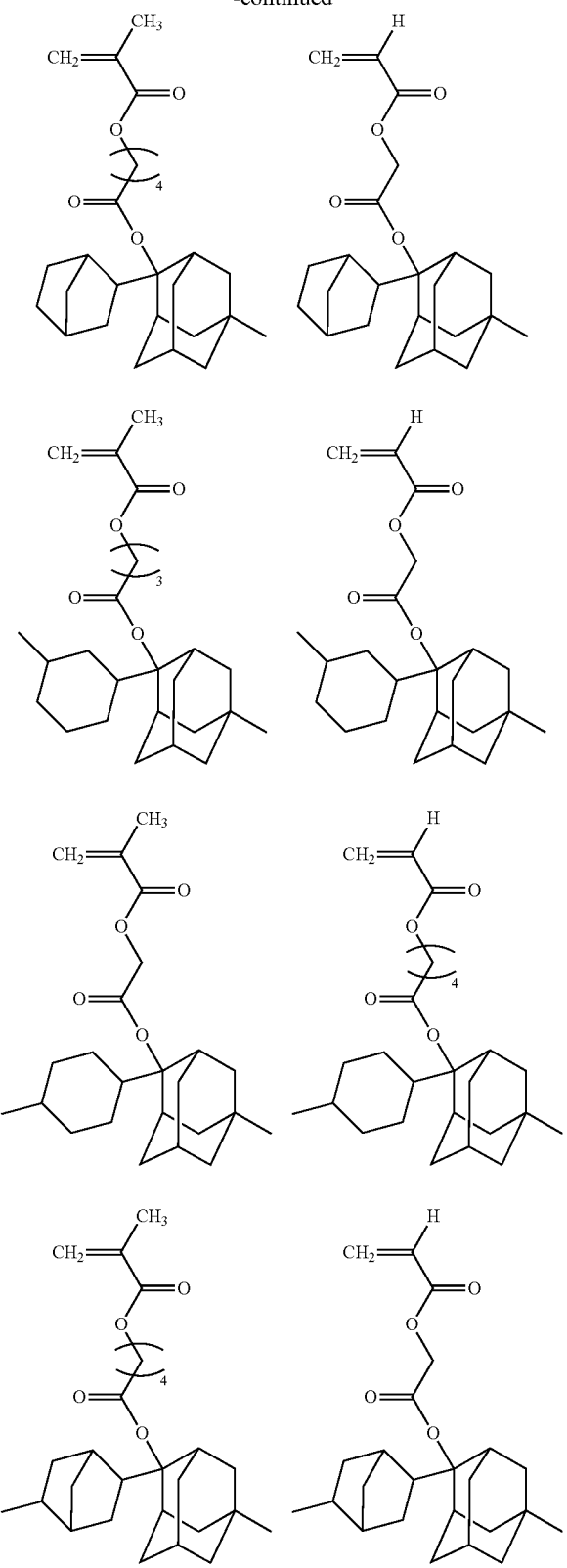

Examples of the monomer having a cyclohexyl group (a-2) include a group below. Among these, 1-ethylcyclohexane-1-yl (meth)acrylate is preferable, and 1-ethylcyclohexane-1-yl methacrylate is more preferable.

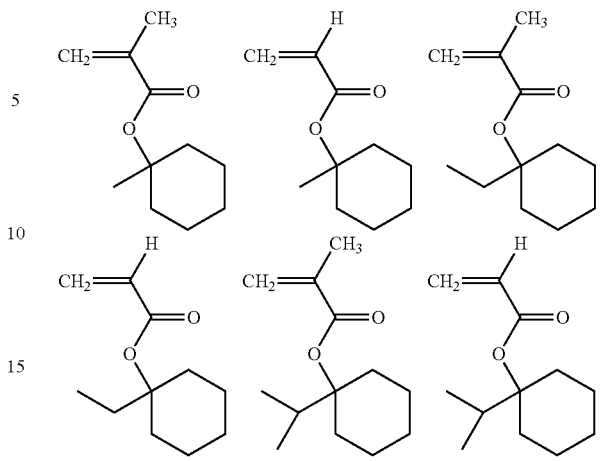

When the resin (A) contains the structural unit derived from the monomer represented by the formula (a-1) and/or the formula (a-2), the total content thereof is generally 10 to 95 mol %, preferably 15 to 90 mol %, and more preferably 20 to 85 mol %, with respect to the total structural units constituting the resin (A).

Monomers having an acid-labile group and a carbon-carbon double bond includes a monomer having norbornene ring presented by the formula (a-3). A resin having a structural unit derived from the monomer (a-3) can improve the resolution of the obtained resist composition because it has a bulky structure, and also can improve a dry-etching tolerance of the obtained resist composition because of incorporated a rigid norbornene ring into a main chain of the resin.

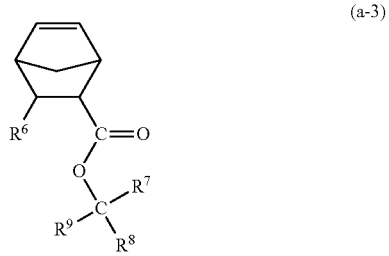

(a-3)

wherein $R^6$ represents a hydrogen atom, an optionally substituted $C_1$ to $C_3$ aliphatic hydrocarbon group (e.g., hydroxy group), carboxy group, cyano group or —COOR$^m$, $R^m$ represents a $C_1$ to $C_8$ aliphatic hydrocarbon group or a $C_1$ to $C_{20}$ saturated cyclic hydrocarbon group, one or more hydrogen atom contained in the aliphatic hydrocarbon group and the saturated cyclic hydrocarbon group may be replaced with hydroxy group, one or more —CH$_2$— contained in the aliphatic hydrocarbon group and the saturated cyclic hydrocarbon group may be replaced by —O— or —CO—;

$R^7$ to $R^9$ independently represent a $C_1$ to $C_{12}$ aliphatic hydrocarbon group or a $C_3$ to $C_{20}$ saturated cyclic hydrocarbon group, or $R^8$ and $R^9$ may be bonded together to form a ring, one or more hydrogen atom contained in the aliphatic hydrocarbon group and the saturated cyclic hydrocarbon group may be replaced with a hydroxy group or the like, one or more —CH$_2$— contained in the aliphatic hydrocarbon group and the saturated cyclic hydrocarbon group may be replaced by —O— or —CO—.

Examples of the aliphatic hydrocarbon group which may be substituted with a substituent of $R^6$ include methyl, ethyl, propyl, hydroxymethyl and 2-hydroxyethyl groups.

Examples of $R^m$ include methyl, ethyl, propyl, 2-oxo-oxolane-3-yl and 2-oxo-oxolane-4-yl groups.

Examples of $R^7$ to $R^9$ include methyl, ethyl, cyclohexyl, methylcyclohexyl, hydroxycyclohexyl, oxocyclohexyl and adamantyl groups.

Examples of the saturated cyclic hydrocarbon formed together with $R^8$, $R^9$ and carbon atom bonded thereto include cyclohexyl and adamantyl groups.

Examples of the monomer having a norbornene ring (a-3) include, for example, tert-butyl 5-norbornene-2-carboxylate, 1-cyclohexyl-1-methylethyl 5-norbornene-2-carboxylate, 1-methylcyclohexyl 5-norbornene-2-carboxylate,2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-(4-oxocyclohexyl)-1-ethyl 5-norbornene-2-carboxylate, and 1-(1-adamantyl)-1-methylethyl 5-norbornene-2-carboxylate.

When the resin (A) contains the structural unit derived from the monomer represented by the formula (a-3), the content thereof is generally 10 to 95 mol %, preferably 15 to 90 mol %, and more preferably 20 to 85 mol %, with respect to the total structural units constituting the resin (A).

Examples of a monomer having an acid-labile group and a carbon-carbon double bond include a monomer represented by the formula (a-4).

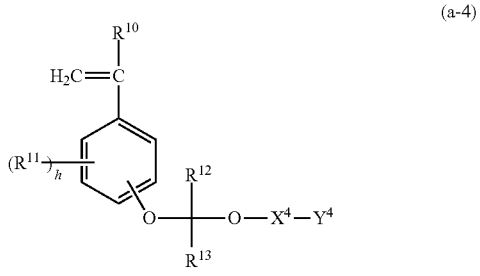

(a-4)

wherein $R^{10}$ represents a hydrogen atom, a halogen atom or a $C_1$ to $C_6$ alkyl group that optionally has a halogen atom;

$R^{11}$ in each occurrence independently represent a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyl group or methacryloyl group;

h represents an integer 0 to 4;

$R^{12}$ and $R^{13}$ independently represent a hydrogen atom or a $C_1$ to $C_{12}$ hydrocarbon group;

$X^4$ represents a single bond or an optionally substituted $C_1$ to $C_{17}$ divalent saturated hydrocarbon group, and one or more —$CH_2$— contained in the saturated hydrocarbon group may be replaced by —CO—, —O—, —S—, —$SO_2$ or —N($R^c$)—, $R^c$ represents a hydrogen atom or a $C_1$ to $C_6$ aliphatic hydrocarbon group;

$Y^4$ represents a $C_1$ to $C_{12}$ aliphatic hydrocarbon group, a $C_3$ to $C_{18}$ saturated cyclic hydrocarbon group or a $C_6$ to $C_{18}$ aromatic hydrocarbon group, the aliphatic hydrocarbon group, the saturated cyclic hydrocarbon group and the aromatic hydrocarbon group may optionally has a substituent.

Examples of the alkyl group that optionally has a halogen atom include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, perbromomethyl and periodomethyl groups.

Examples of the alkyl group, the alkoxy group and the like include the same examples described above.

Examples of the acyl group include acetyl, propionyl and butyryl groups.

Examples of the acyloxy group include acetyloxy, propionyloxy and butyryloxy groups.

In the formula (a-4), the alkyl group of $R^{10}$ and $R^{11}$ is preferably a $C_1$ to $C_4$ alkyl group, more preferably a $C_1$ to $C_2$ alkyl group, and still more preferably methyl group.

The alkoxy group of $R^{11}$ is preferably a $C_1$ to $C_4$ alkoxy group, more preferably a $C_1$ to $C_2$ alkoxy group, and still more preferably methoxy group.

Examples of the substituent that may be optionally substituted to $X^4$ and $Y^4$ includes a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group and the like. Among these, a hydroxy group is preferable.

Examples of the monomer represented by the formula (a-4) include a monomer below.

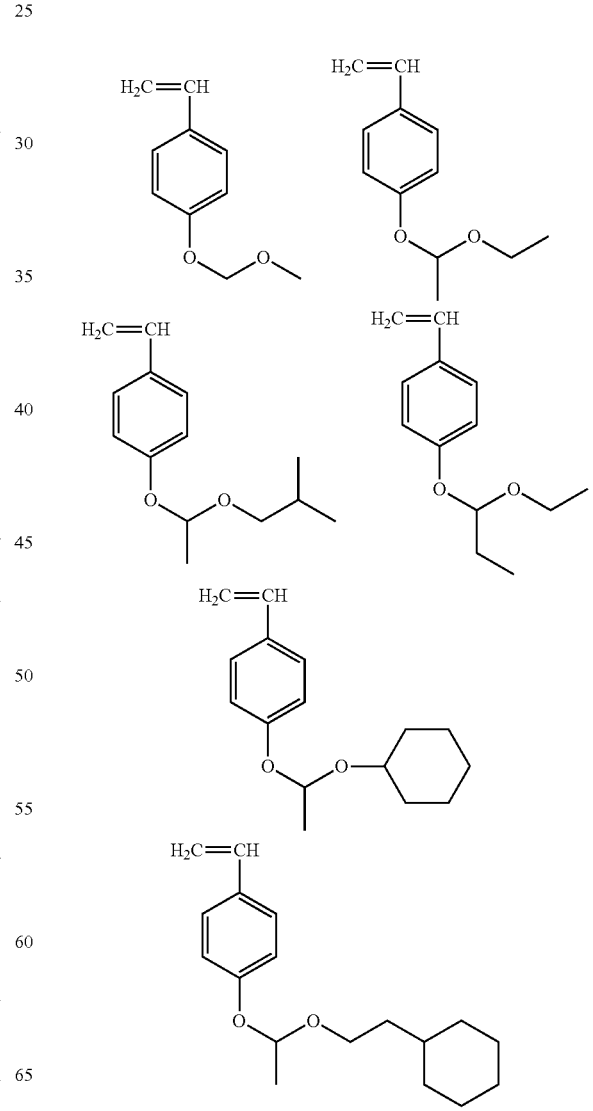

-continued
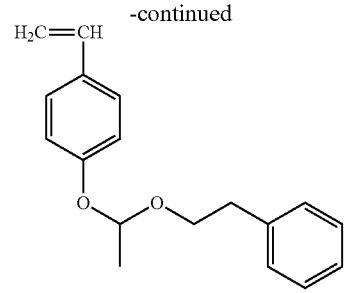
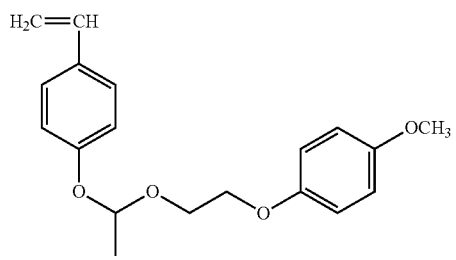
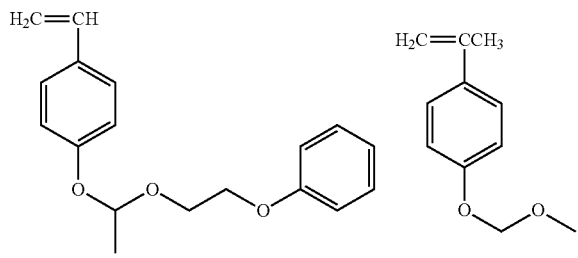
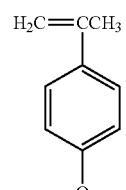
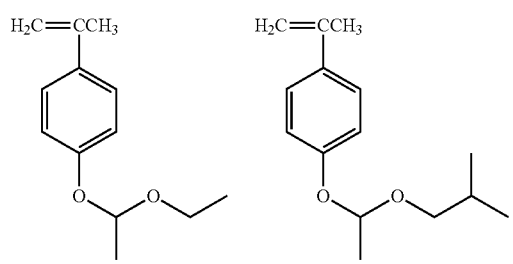
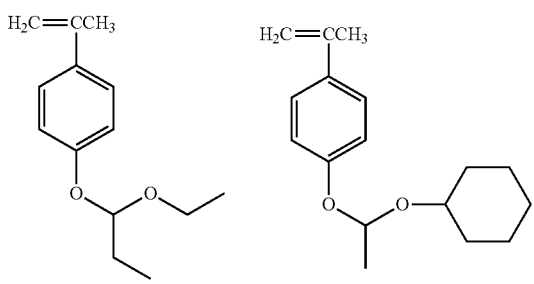
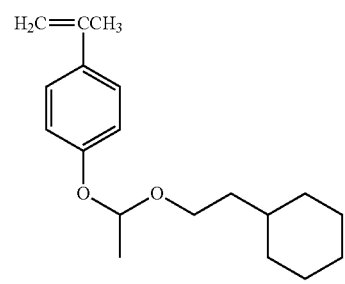
-continued
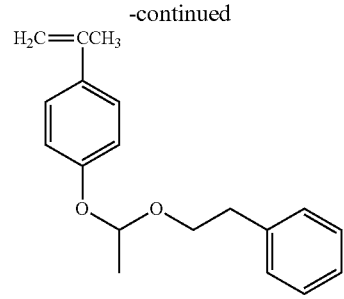
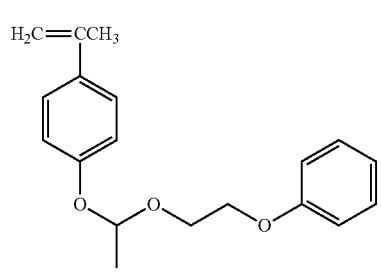
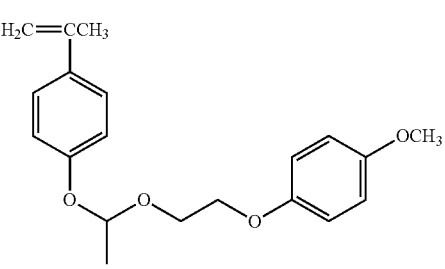
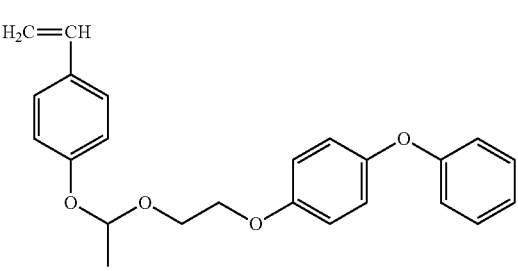
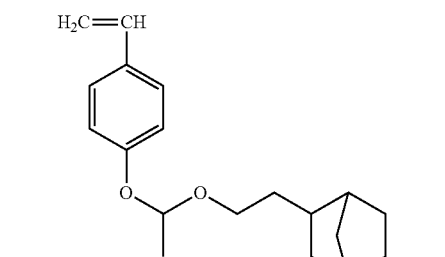
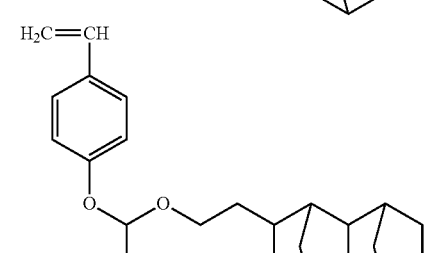
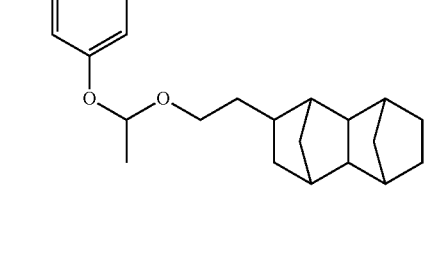

-continued
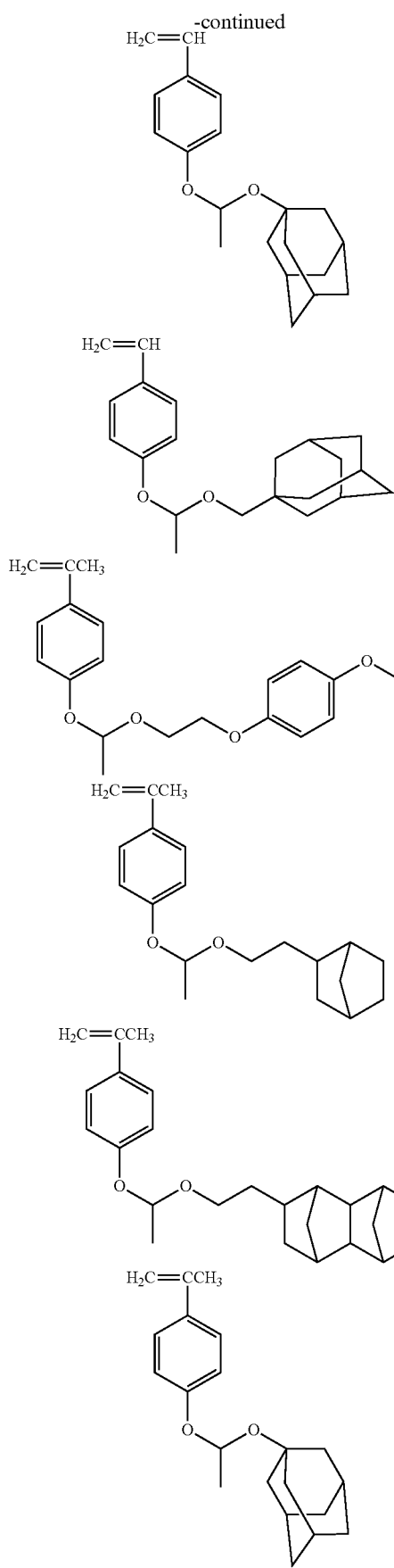
-continued
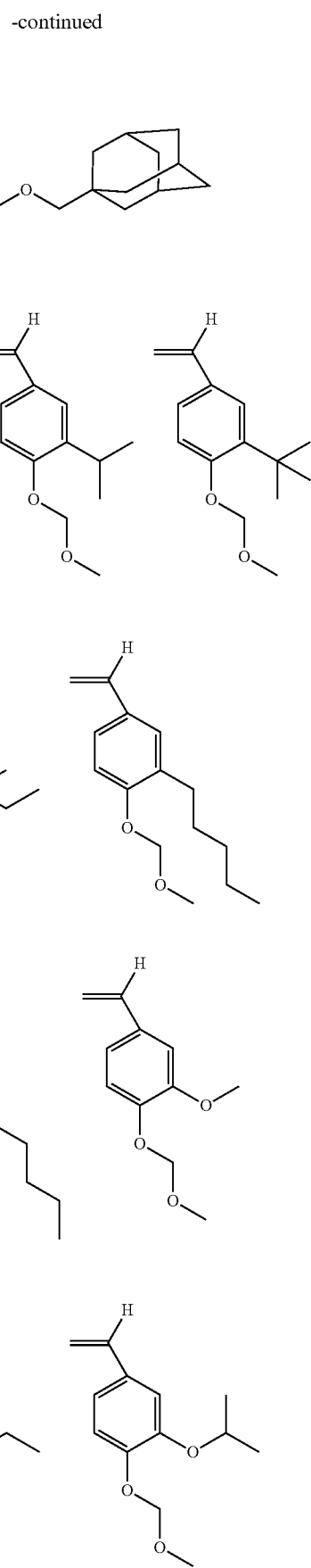

-continued
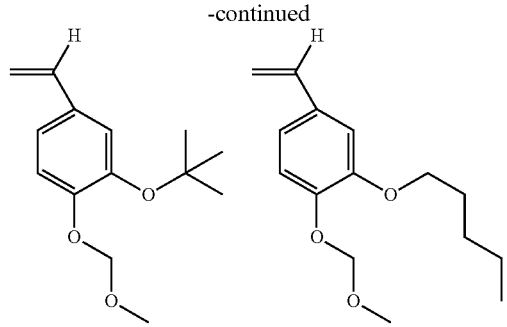
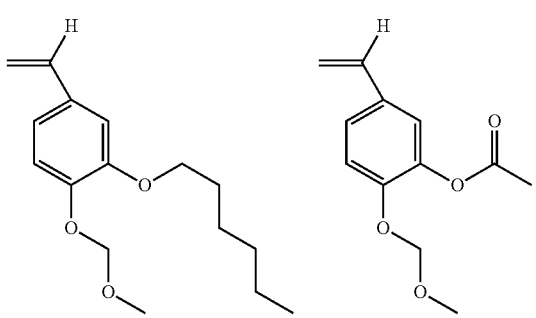
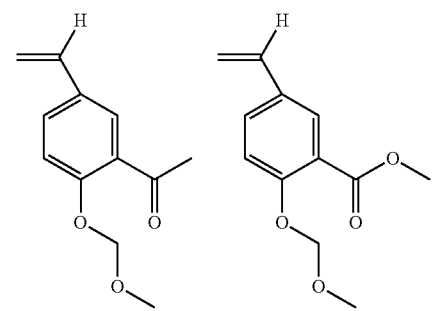
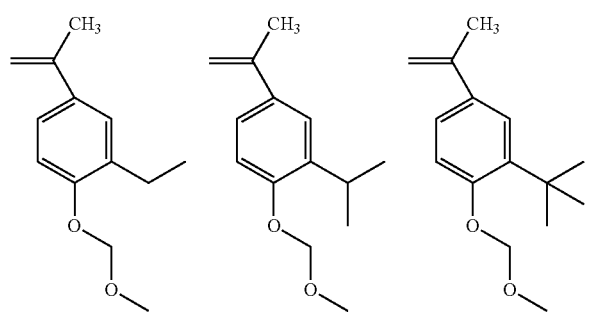
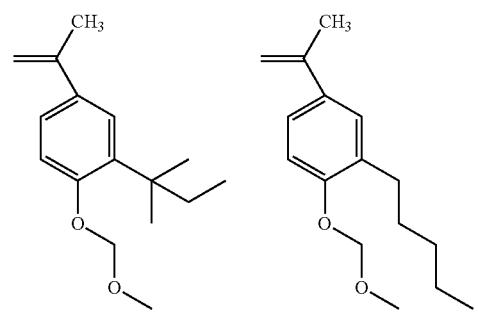
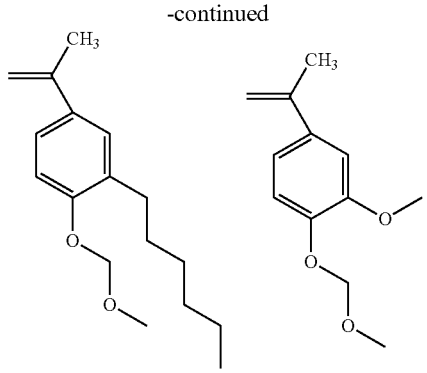
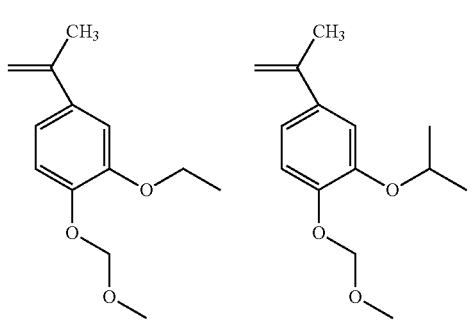
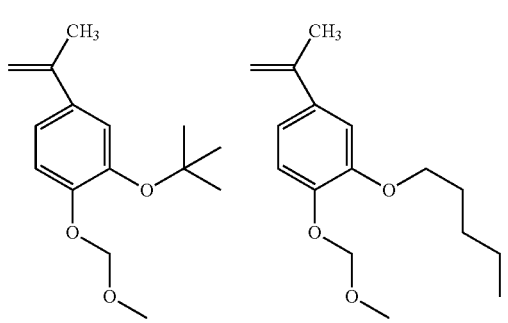
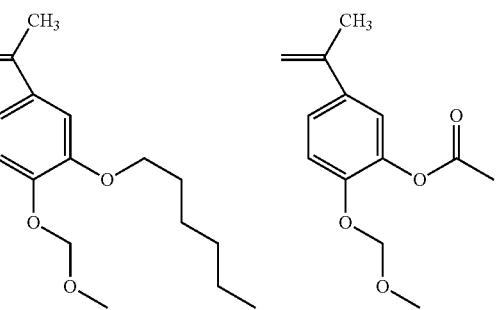
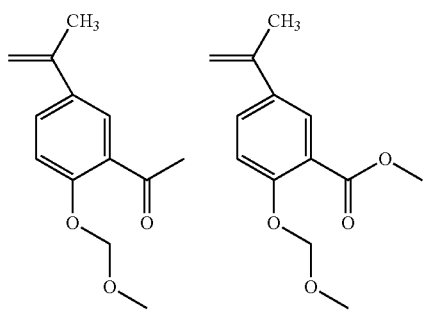

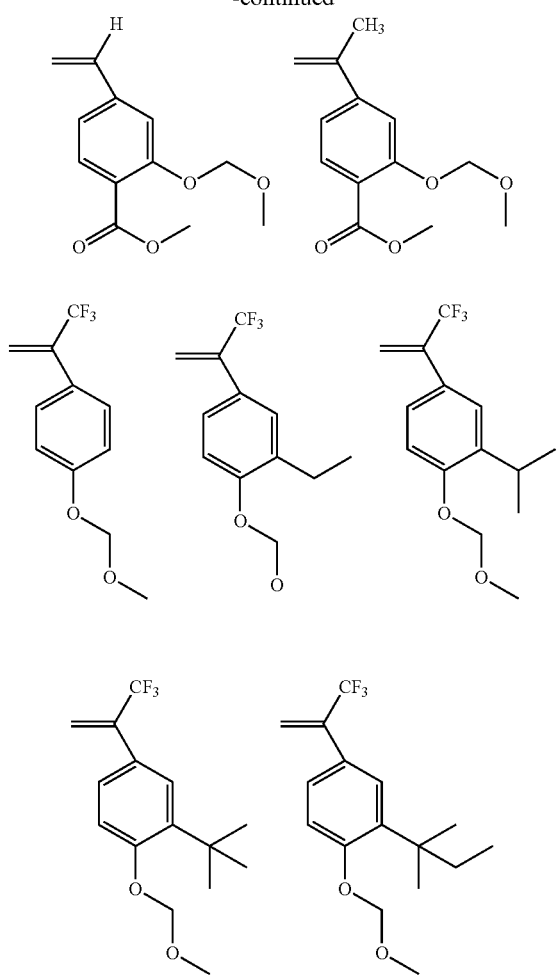

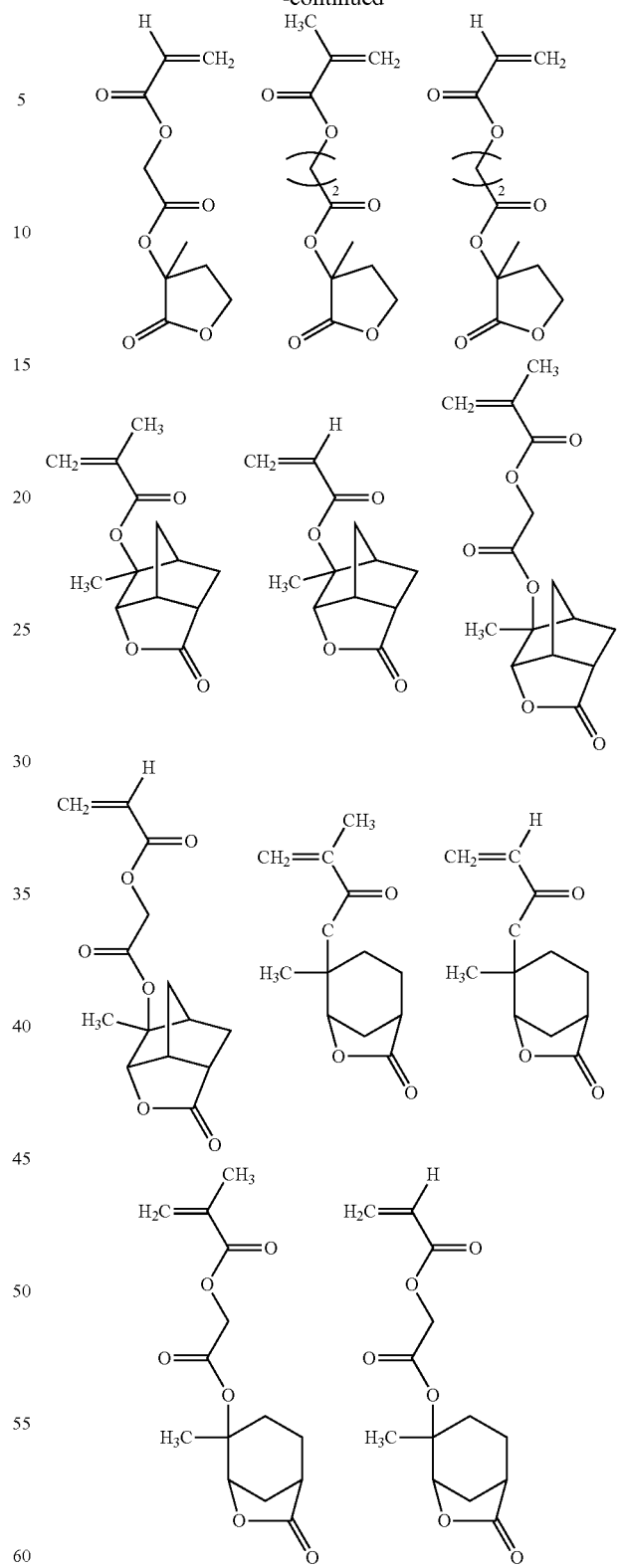

When the resin (A) contains the structural unit derived from the monomer represented by the formula (a-4), the content thereof is generally 10 to 95 mol %, preferably 15 to 90 mol %, more preferably 20 to 85 mol %, with respect to the total structural units constituting the resin (A).

Further, a monomer derived from another structural unit having an acid-labile group and carbon-carbon double bond may be used for the resin (A).

Specific examples of such another monomer include a monomer below.

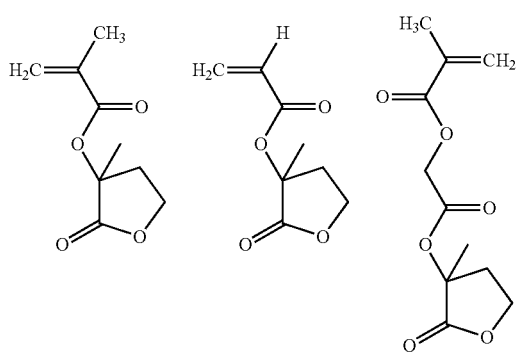

When the resin (A) contains the structural unit derived from the other acid-labile monomer, the content thereof is generally 10 to 95 mol %, preferably 15 to 90 mol %, and more preferably 20 to 85 mol %, with respect to the total structural units constituting the resin (A).

The resin (A) is preferably a copolymer of the monomer having the acid-labile group (a-1) and a monomer not having the acid-labile group (hereinafter may be referred to as an "acid-stable monomer"). The acid-stable monomer may be used singly or mixture of two or more.

When the resin (A) is the copolymer of the monomer having the acid-labile group (a-1) and the acid-stable monomer, the content of the monomer having the acid-labile group (a-1) is preferably 10 to 80 mol %, and more preferably 20 to 60 mol %, with respect to the total structural units constituting the resin (A). Also, the content of the structural unit derived from the monomer having an adamantyl group (in particular, the monomer having the acid-labile group (a-1)) is preferably 15 mol % or more with respect to the monomer having the acid-labile group (a-1). The more rate of the monomer having an adamantyl group increases, the more dry etching resistance of the resulting resist improves.

As the acid-stable monomer, a monomer having a hydroxy group (b) or a lactone ring (c) is preferable. When a resin containing the structural unit derived from the acid-stable monomer having hydroxy group or the acid-stable monomer having a lactone ring is used, the adhesiveness of resist to a substrate and resolution of resist tend to be improved.

<Acid-stable Monomer Having Hydroxy Group (b)>

When KrF excimer laser lithography (248 nm), or high-energy irradiation such as electron beam or EUV light is used for the resist composition, using the acid-stable monomer having a phenolic hydroxy group (b-1) such as hydroxystyrenes as the acid-stable monomer having the hydroxy group is preferable. When ArF excimer laser lithography (193 nm), i.e., short wavelength excimer laser lithography is used, using the acid-stable monomer having a hydroxy adamantyl group represented by the formula (b-2) as the acid-stable monomer having the hydroxy group is preferable. The acid-stable monomer having hydroxy group may be used singly or mixture of two or more.

Examples of the acid-stable monomer having phenolic hydroxy group include styrene monomer represented by the formula (b-1) such as p- or m-hydroxystyrene.

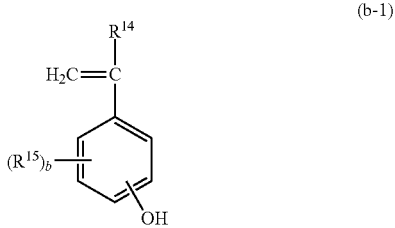

(b-1)

wherein $R^{14}$ represents a hydrogen atom, a halogen atom or a $C_1$ to $C_6$ alkyl group that optionally has a halogen atom;

$R^{15}$ represents a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyl group or methacryloyl group;

b represents an integer 0 to 4.

In the formula (b-1), the alkyl group of $R^{14}$ is preferably a $C_1$ to $C_4$ alkyl group, more preferably a $C_1$ to $C_2$ alkyl group, and still more preferably methyl group.

The alkoxy group is preferably a $C_1$ to $C_4$ alkoxy group, more preferably a $C_1$ to $C_2$ alkoxy group, and still more preferably methoxy group.

Such copolymer having the structural unit derived from the monomer having a phenolic hydroxy group (b-1) can be produced by radical-polymerizing a monomer to be copolymerized and an acetyloxy styrene corresponding to a monomer replaced the phenolic hydroxy group by the acetyloxy group, and then de-acetylating them using an acid.

Specific examples of the monomer having phenolic hydroxy group (b-1) include a monomer below. Among these, 4-hydroxystyrene or 4-hydroxy-α-methylstyrene is especially preferable.

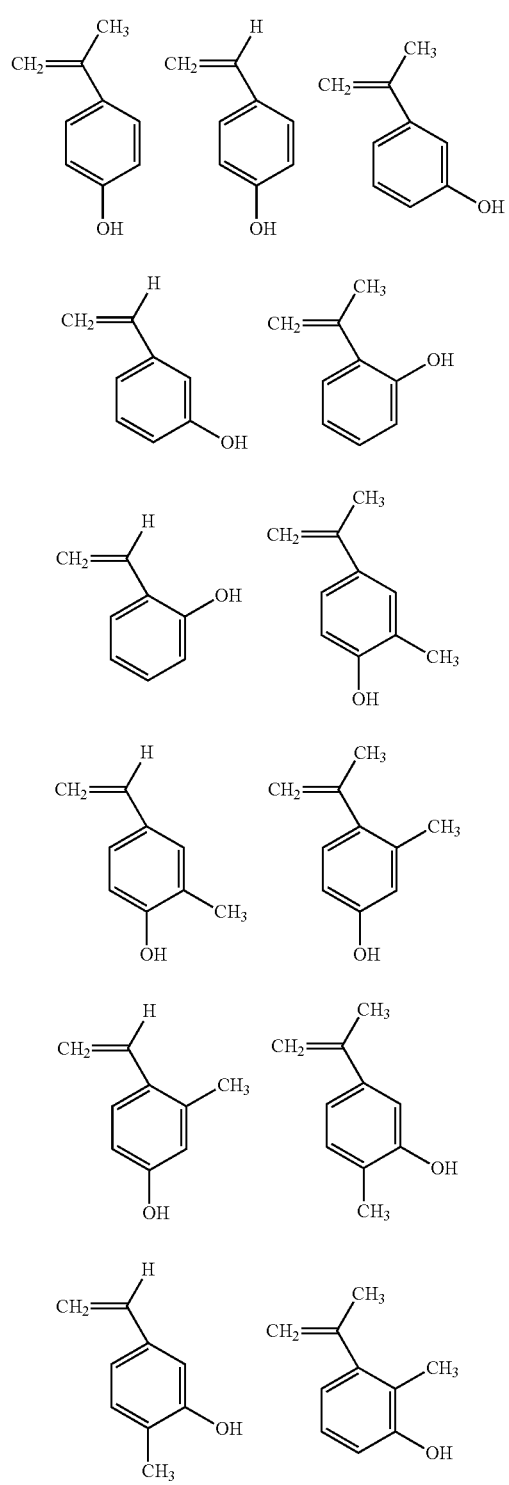

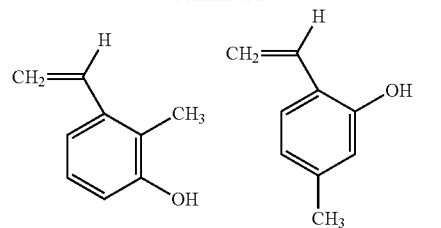
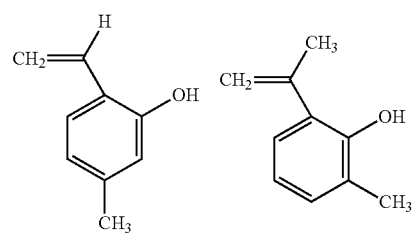
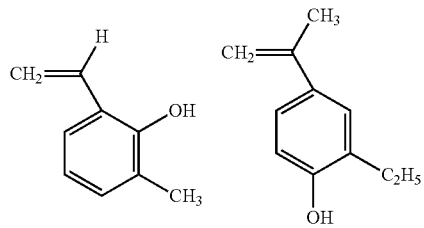
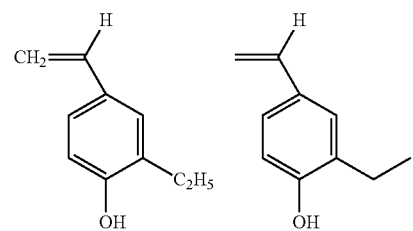
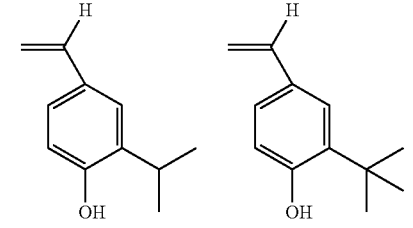
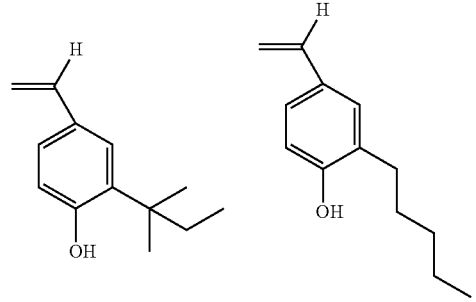
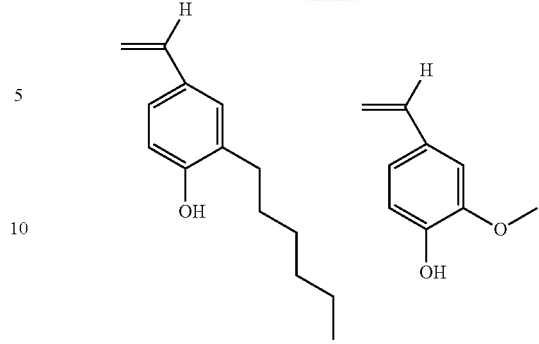
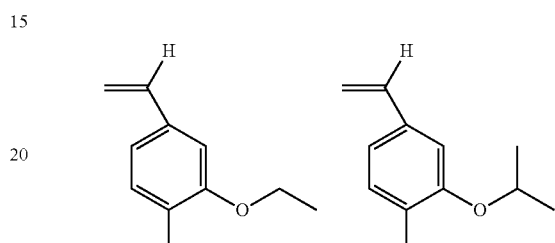
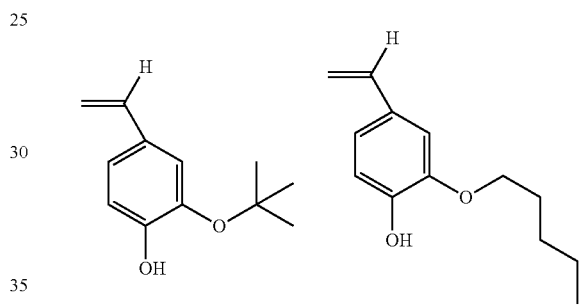
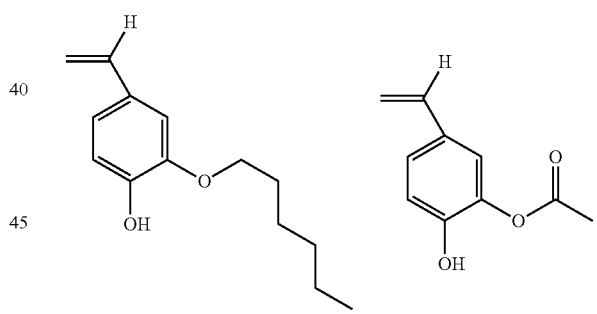
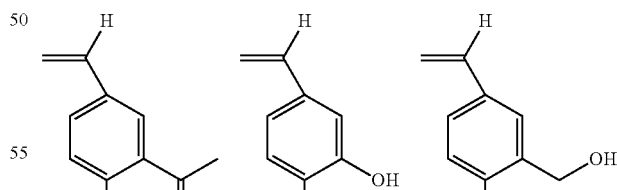
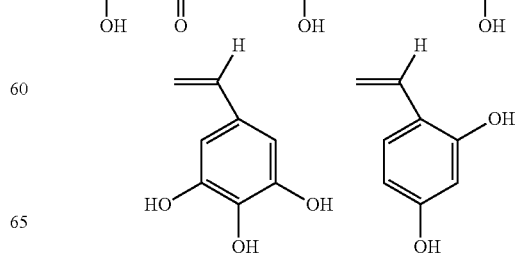

-continued
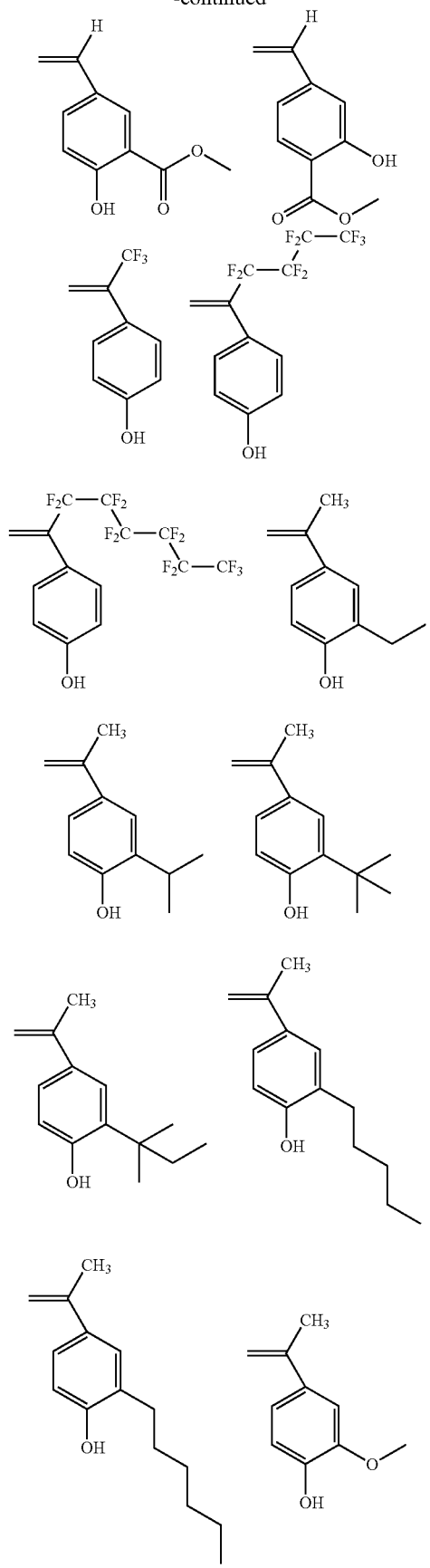
-continued
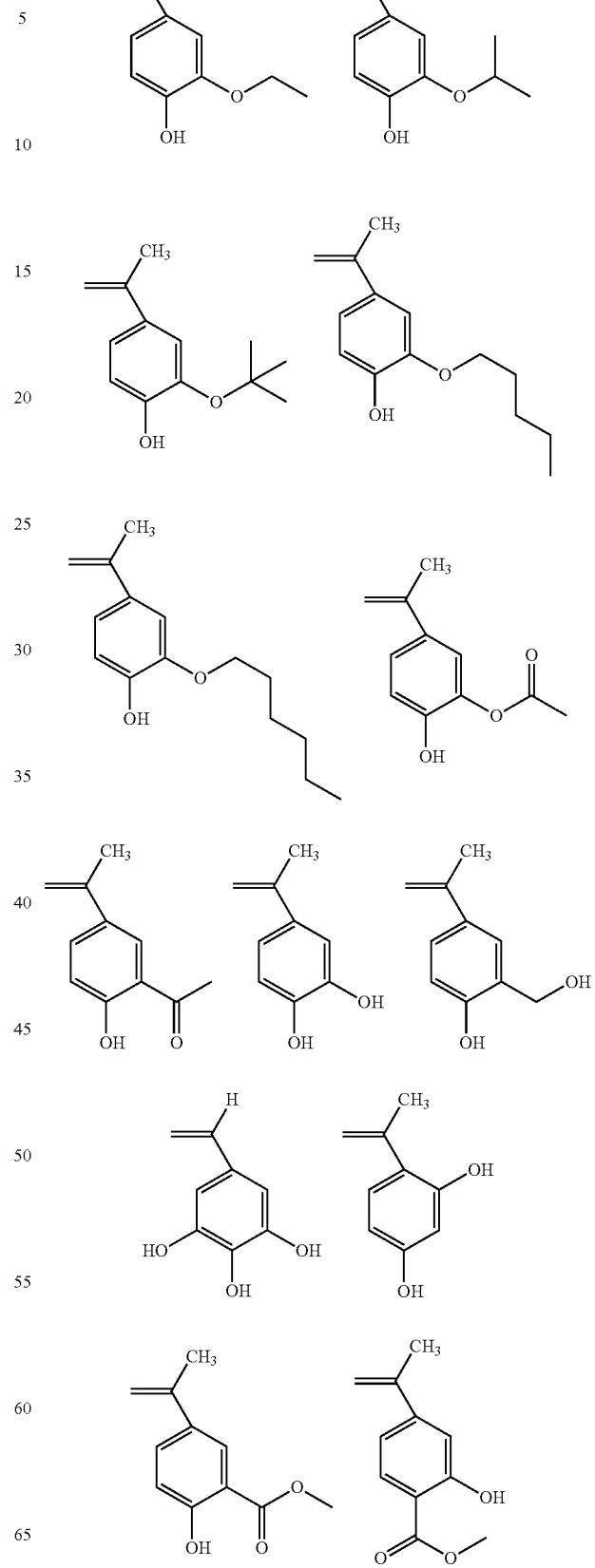

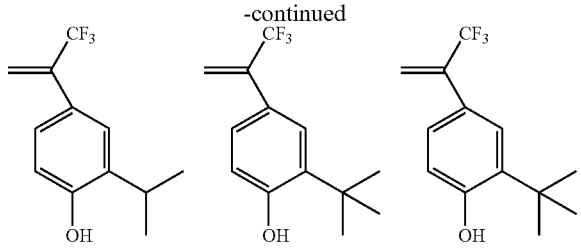

-continued

When the resin (A) contains the structural unit derived from the monomer represented by the formula (b-1), the content thereof is generally 5 to 90 mol %, preferably 10 to 85 mol %, and more preferably 15 to 80 mol %, with respect to the total structural units constituting the resin (A).

Example of the acid-stable monomer having a hydroxy adamantyl group include a monomer represented by the formula (b-2).

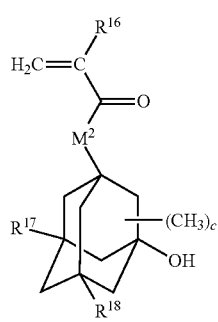

(b-2)

wherein $M^2$ represents —O— or —O—$(CH_2)_k$—CO—O—, k represents an integer of 1 to 7;

$R^{16}$ represents a hydrogen atom or a methyl group;

$R^{17}$ and $R^{18}$ independently represent a hydrogen atom, a methyl group or a hydroxy group;

c represents an integer of 0 to 10.

In the formula (b-2), $M^2$ is preferably —O—, —O—$(CH_2)_f$—CO—O—, here f represents an integer of 1 to 4, and more preferably —O—;

$R^{16}$ is preferably a methyl group.

$R^{17}$ is preferably a hydrogen atom.

$R^{18}$ is preferably a hydrogen atom or a hydroxy group.

c is preferably an integer of 0 to 3, and more preferably an integer of 0 or 1.

Examples of the acid-stable monomer having the hydroxy adamantyl group include a monomer below. Among these, 3-hydroxyadamantane-1-yl (meth)acrylate, 3,5-dihydroxyadamantane-1-yl (meth)acrylate, and 1-(3,5-dihydroxyadamantane-1-yl oxycarbonyl)methyl (meth)acrylate are preferable, and 3-hydroxyadamantane-1-yl (meth)acrylate and 3,5-dihydroxyadamantane-1-yl (meth)acrylate are more preferable, and 3-hydroxyadamantane-1-yl methacrylate and 3,5-dihydroxyadamantane-1-yl methacrylate are still more preferable.

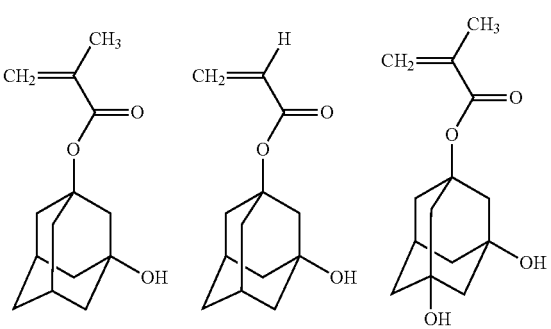
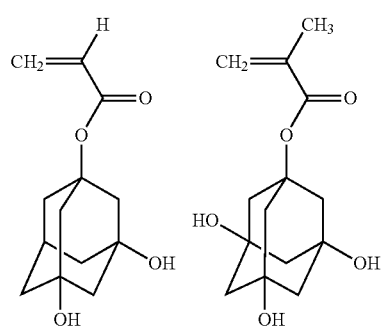
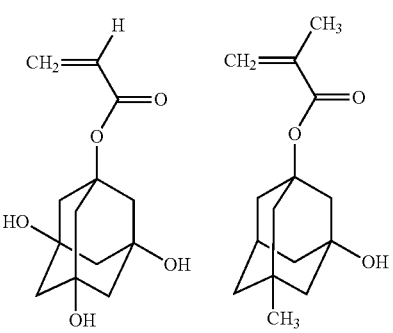
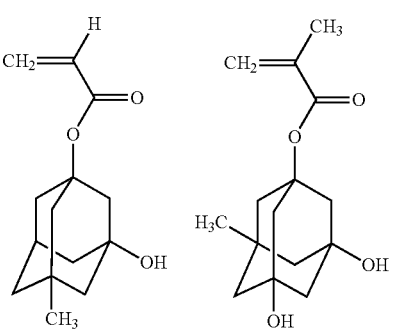
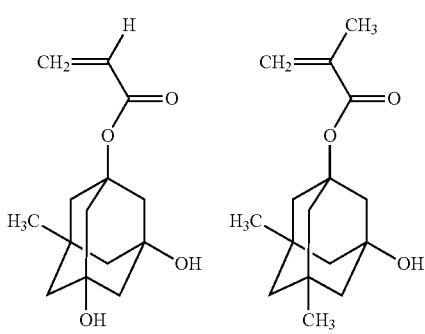

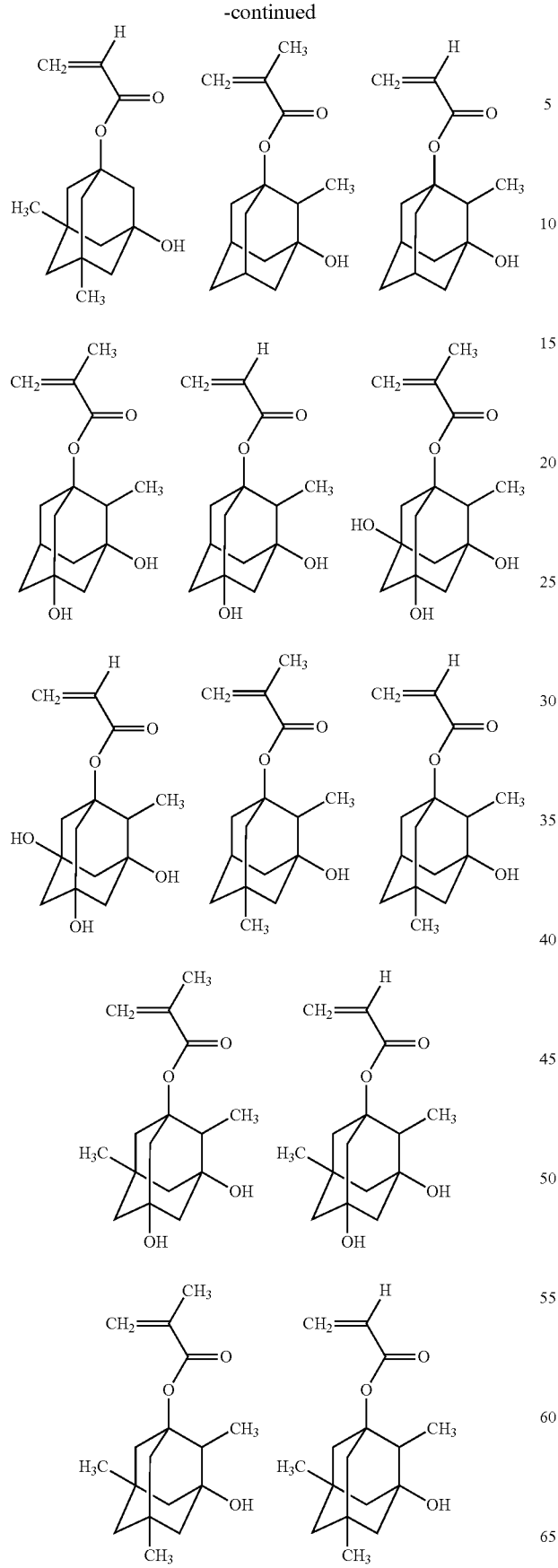
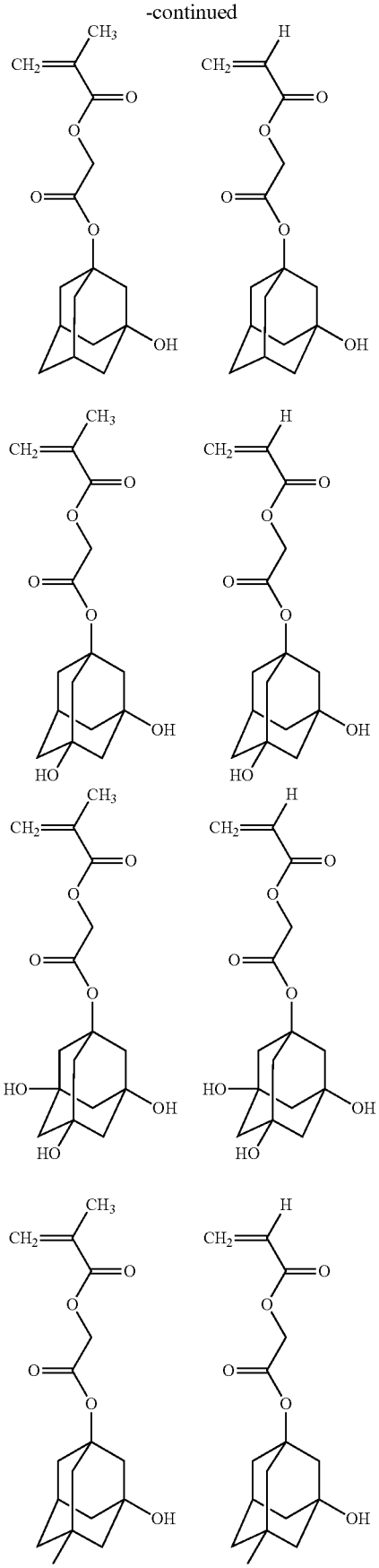

-continued

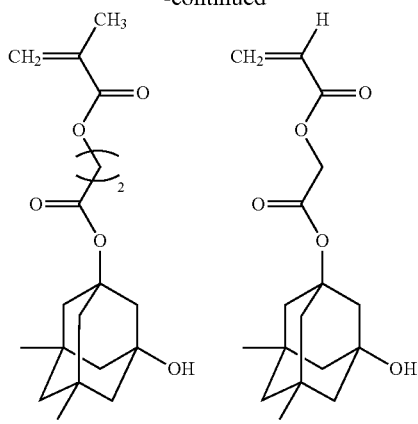

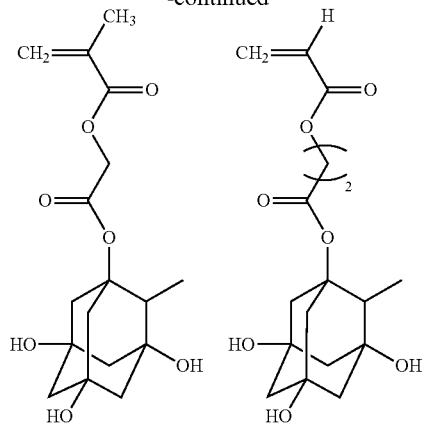

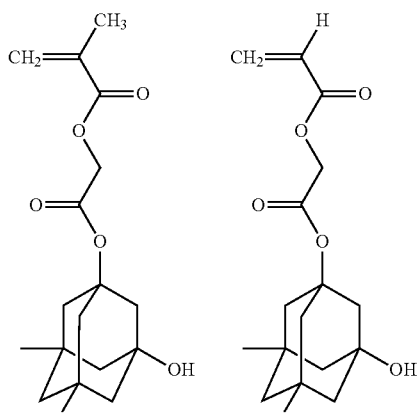

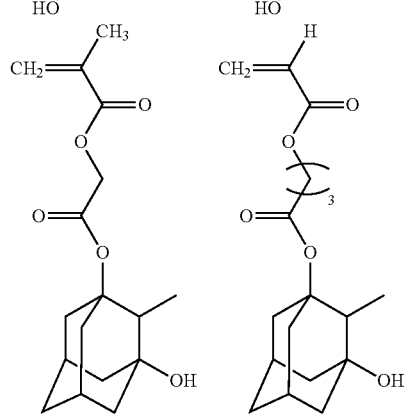

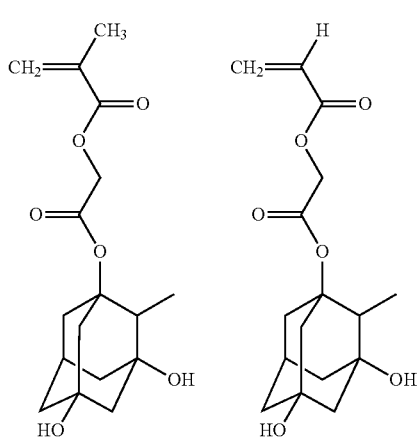

When the resin (A) contains the structural unit derived from the monomer represented by the formula (b-2), the content thereof is generally 3 to 40 mol %, preferably 5 to 35 mol %, more preferably 5 to 30 mol %, and still more preferably 5 to 20 mol %, with respect to the total structural units constituting the resin (A). When the content of the structural unit derived from the monomer represented by the formula (b-2) with this range, it is preferable to tend to widen a focus margin at the time of the resist pattern formation.

<Acid-stable Monomer Having Lactone Ring (c)>

The lactone ring included in the acid-stable monomer may be a monocyclic compound such as β-propiolactone ring, γ-butyrolactone, δ-valerolactone, or a condensed ring with monocyclic lactone ring and other ring. Among these, γ-butyrolactone and condensed ring with γ-butyrolactone and other ring are preferable.

Examples of the acid-stable monomer having the lactone ring include monomers represented by any of the formula (c-1), the formula (c-2) or the formula (c-3). These monomer may be used singly or mixture of two or more.

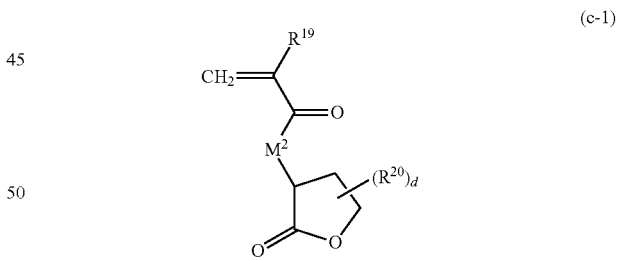

(c-1)

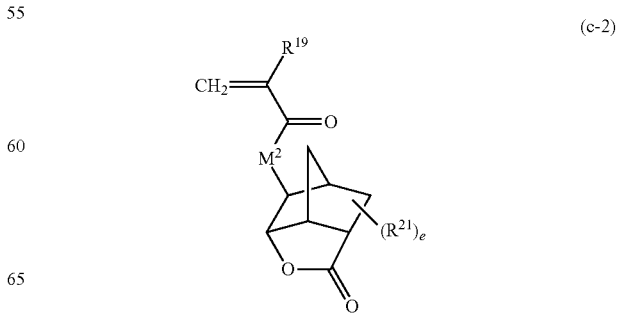

(c-2)

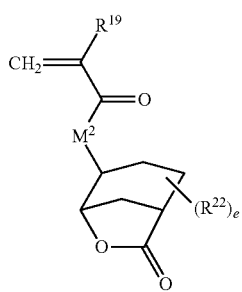

(c-3)

wherein $M^2$ independently represents —O— or —O—$(CH_2)_k$—CO—O—, k represents an integer of 1 to 7;

$R^{19}$ independently represents a hydrogen atom or a methyl group;

$R^{20}$ represents a $C_1$ to $C_4$ aliphatic hydrocarbon group;

$R^{21}$ and $R^{22}$ independently represent a carboxy group, a cyano group or a $C_1$ to $C_4$ aliphatic hydrocarbon group;

d represents an integer of 0 to 5;

e and g independently represent an integer of 0 to 3.

In the formulae (c-1) to (c-3), $M^2$ is independently preferably —O—, —O—$(CH_2)_f$—CO—O—, here f represents an integer of 1 to 4, and more preferably —O—. Provided that in —O— and the like of $M^2$, the left side of the group bonds to —CO— of the formulae (c-1) to (c-3), and the right side of the group bonds to lactone ring, respectively.

$R^{19}$ is preferably a methyl group.

$R^{20}$ is preferably a methyl group.

$R^{21}$ and $R^{22}$ are independently preferably a carboxy group, a cyano group or a methyl group.

d, e and g are independently preferably an integer of 0 to 2, and more preferably 0 or 1.

Examples of the acid-stable monomers having γ-butyrolactone ring (c-1) include a monomer below.

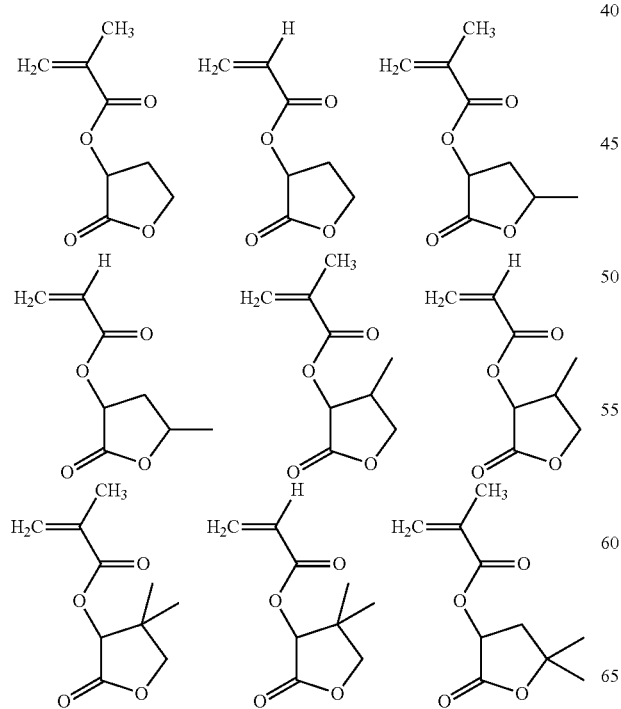

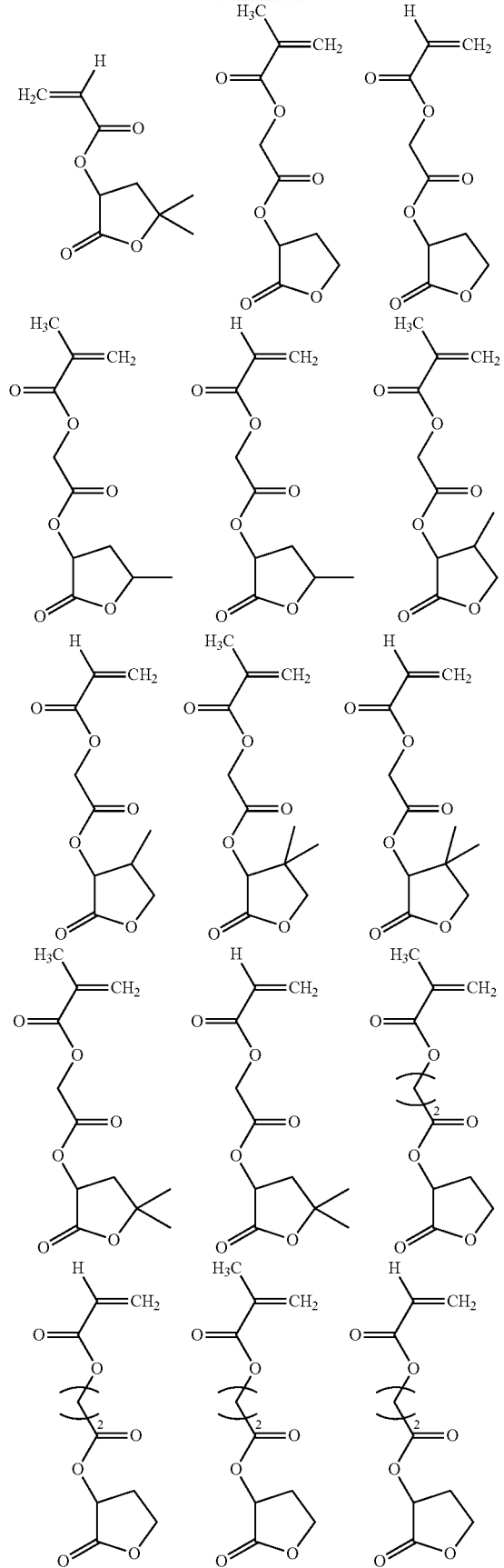

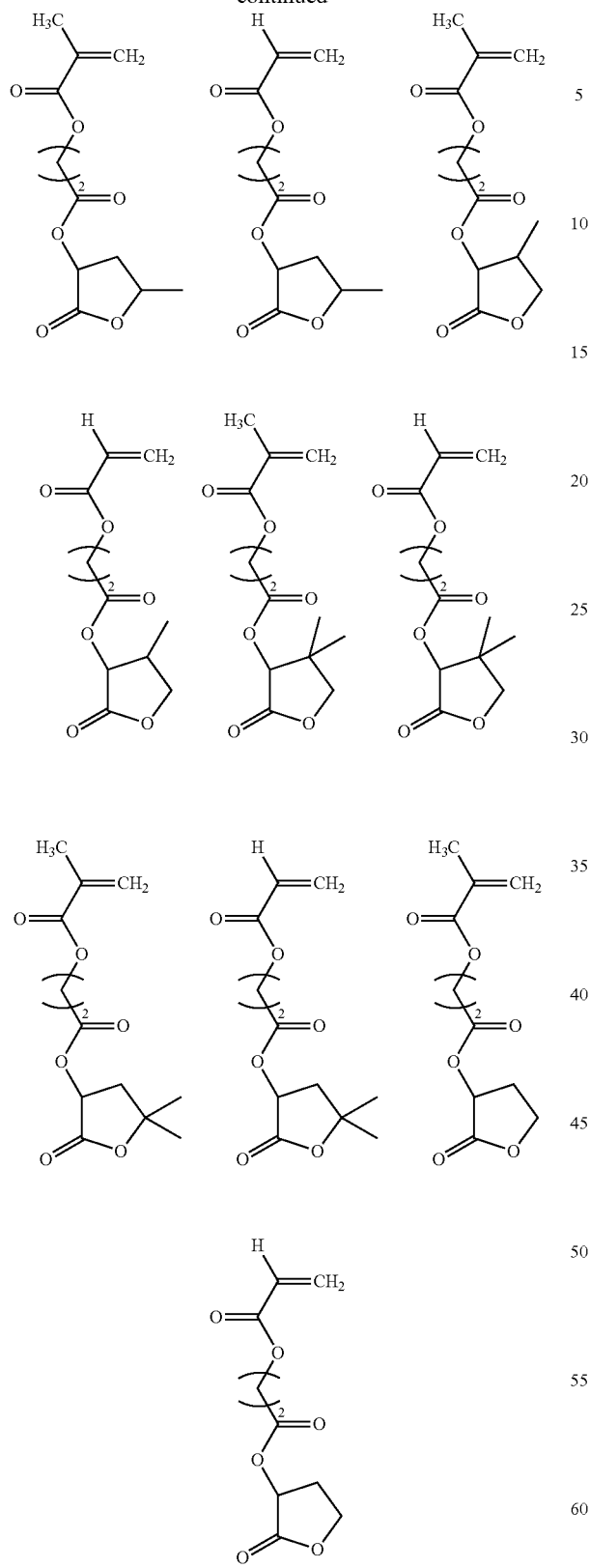
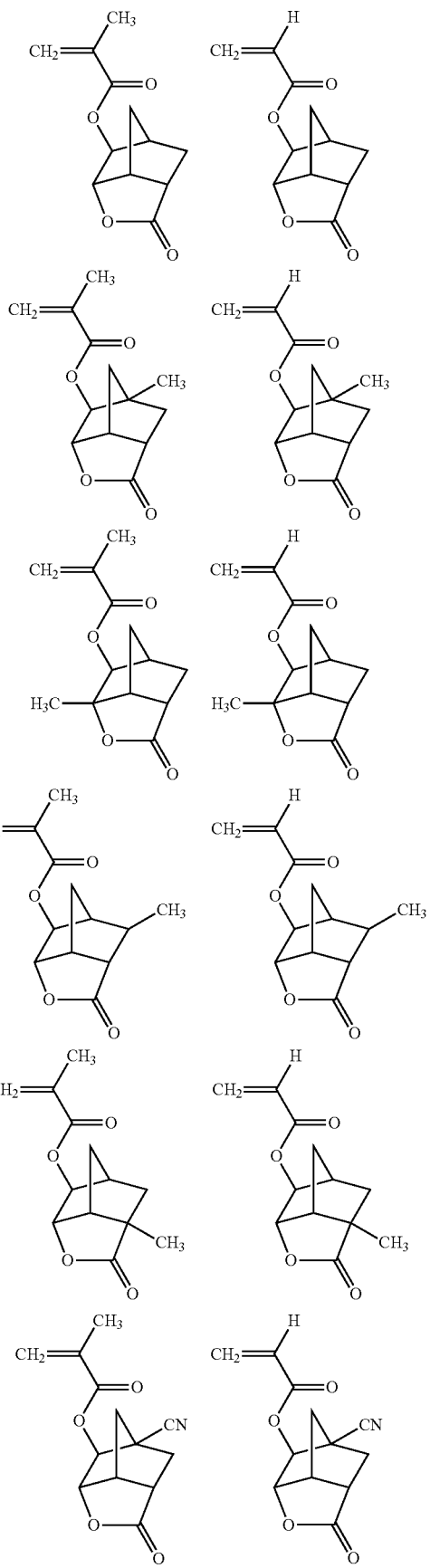
Examples of the acid-stable monomers having γ-butyrolactone ring and norbornene ring represented by the formula (c-2) include a monomer below.

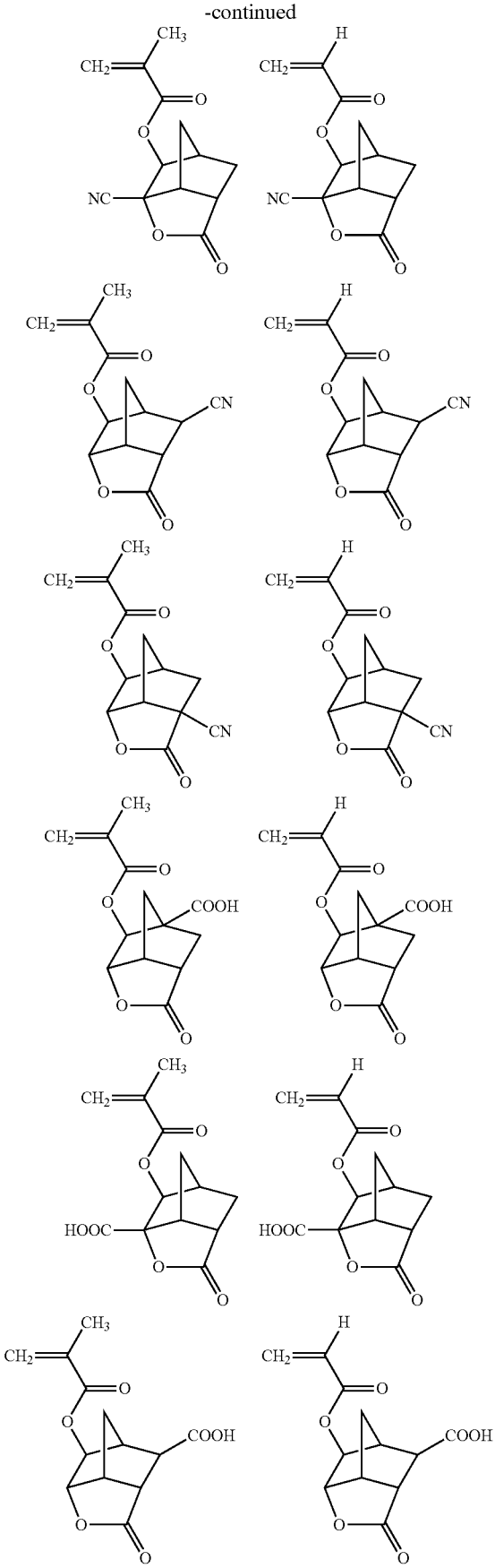
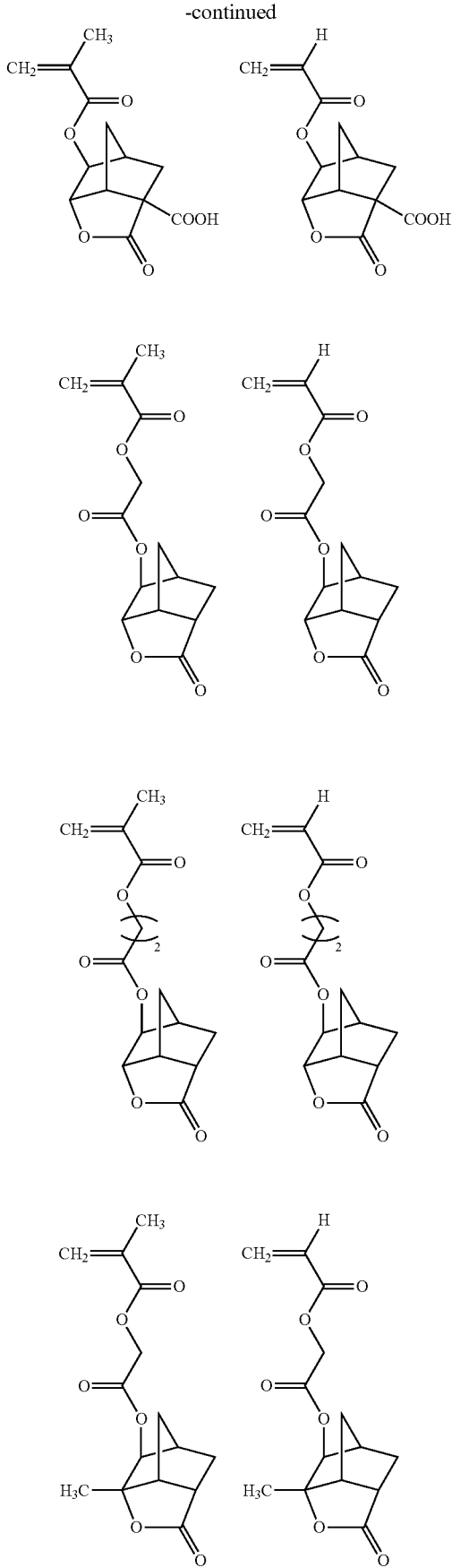

-continued

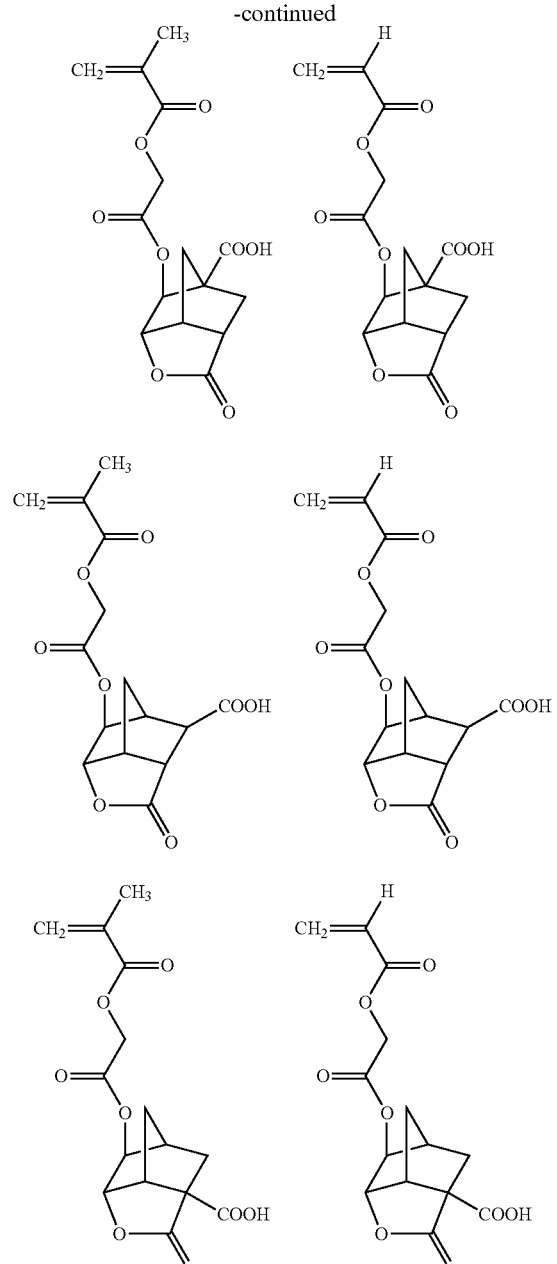
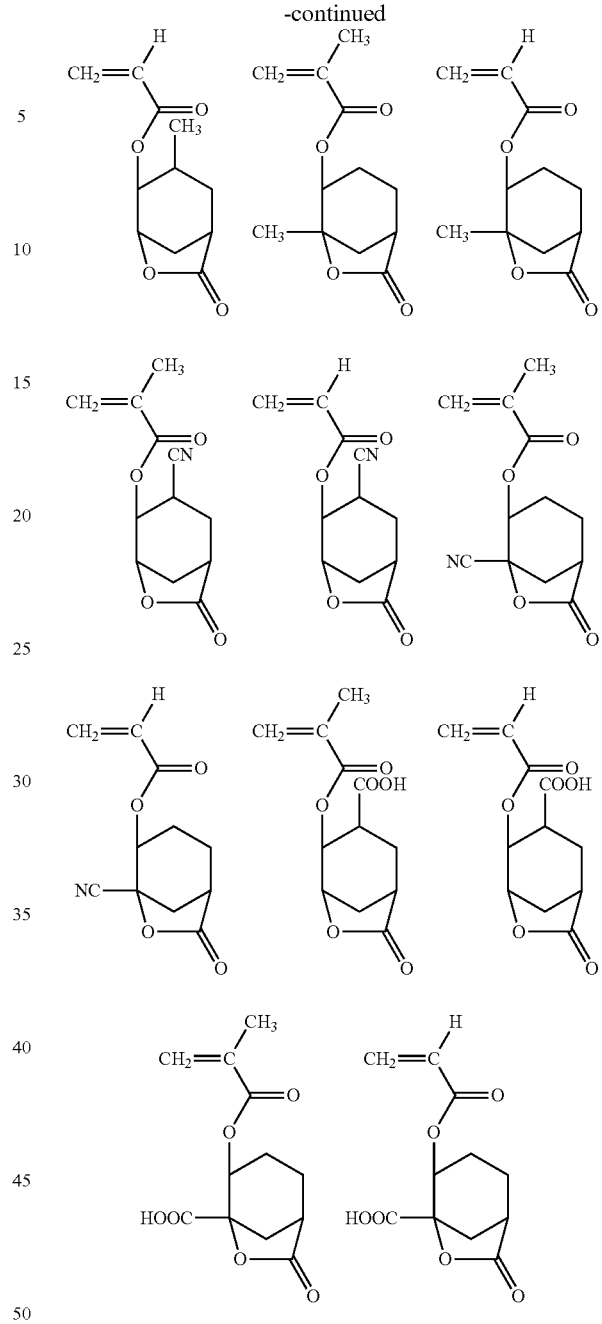
Examples of the acid-stable monomers having a condensed ring with γ-butyrolactone ring and cyclohexane ring represented by the formula (c-3) include a monomer below.
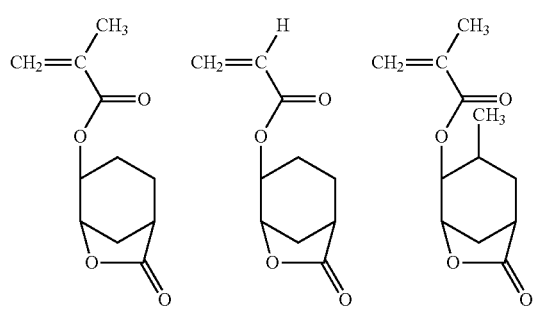
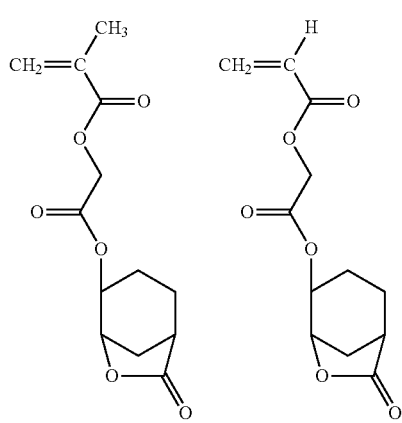

-continued

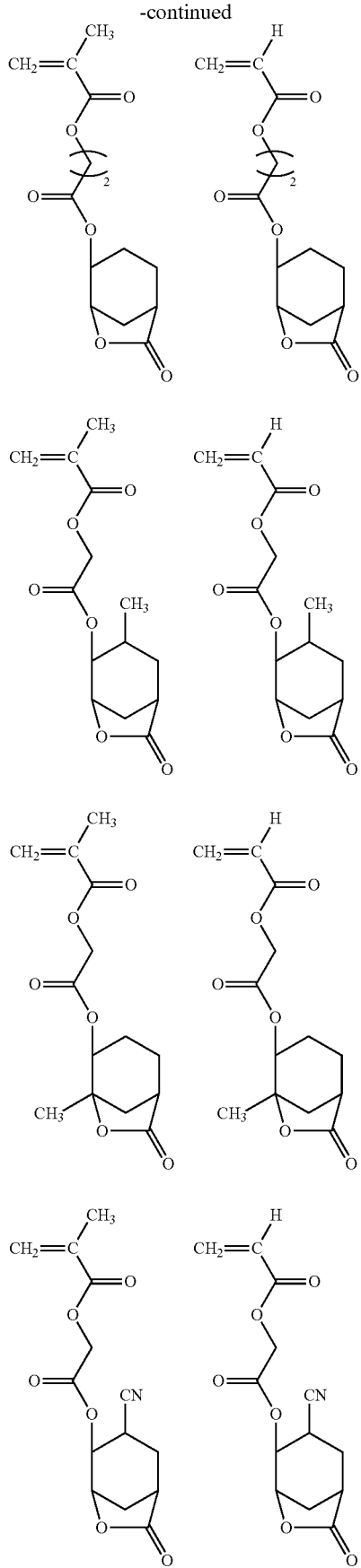

-continued

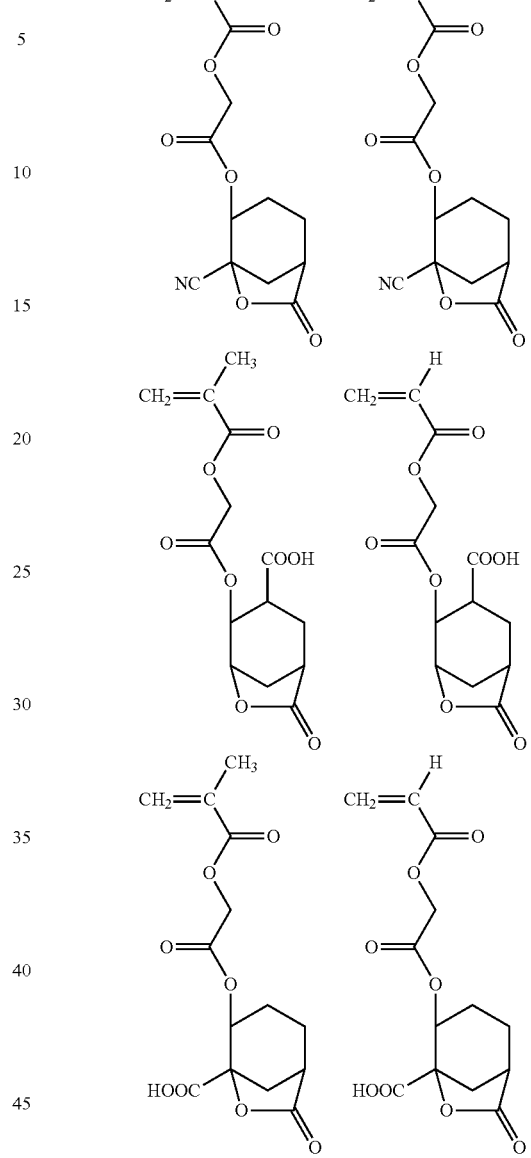

Among the acid-stable monomer having lactone ring(c), (5-oxo-4-oxatricyclo[4.2.1.0$^{3,7}$]nonane-2-yl) (meth)acrylate, tetrahydro-2-oxo-3-furyl (meth)acrylate, and 2-(5-oxo-4-oxatricyclo[4.2.1.0$^{3,7}$]nonane-2-yloxy)-2-oxoethyl (meth)acrylate are preferable, and the (meth)acrylate compounds are more preferable.

When the resin (A) contains the structural unit derived from the monomer represented by the formula (c-1), the structural unit derived from the monomer represented by the formula (c-2) or the structural unit derived from the monomer represented by the formula (c-3), the content thereof is generally 5 to 50 mol %, preferably 10 to 45 mol %, and more preferably 15 to 40 mol %, with respect to the total structural units constituting the resin (A), respectively.

When the resin (A) contains the structural unit derived from the acid-stable monomer having the lactone ring (c), the total content thereof is generally 5 to 60 mol %, preferably 15 to 55 mol %, with respect to the total structural units constituting the resin (A).

<Other Acid-Stable Monomer>

Examples of the acid-stable monomer other than the above include maleic anhydride represented by the formula (d-1), itaconic anhydride represented by the formula (d-2) or an acid-stable monomer having norbornene ring represented by the formula (d-3), for example.

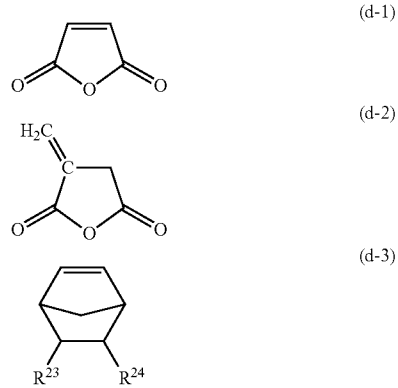

wherein $R^{23}$ and $R^{24}$ independently represent a hydrogen atom, an optionally substituted $C_1$ to $C_3$ aliphatic hydrocarbon group (e.g., with a hydroxy group), a cyano group, a carboxy group or —$COOR^{25}$, or $R^{23}$ and $R^{24}$ may be bonded together to form —CO—O—CO—, $R^{25}$ represents a $C_1$ to $C_{36}$ aliphatic hydrocarbon group or a $C_3$ to $C_{36}$ saturated cyclic hydrocarbon group, one or more —$CH_2$— contained in the aliphatic hydrocarbon group and the saturated cyclic hydrocarbon group may be replaced by —O— or —CO—, provided that excluding a group in which the —$COOR^{25}$ is an acid-labile group, that is, $R^{25}$ does not include a group in which the tertiary carbon atom bonds to —O—.

Examples of the optionally substituted aliphatic hydrocarbon of $R^{23}$ and $R^{24}$ include, for example, methyl, ethyl, propyl, hydroxymethyl and 2-hydroxyethyl groups.

The aliphatic hydrocarbon group of $R^{25}$ has preferably 1 to 8 carbon atoms, and more preferably 1 to 6 carbon atoms. The saturated cyclic hydrocarbon group has preferably 4 to 36 carbon atoms, and more preferably 4 to 12 carbon atoms.

Examples of $R^{25}$ include methyl, ethyl, propyl, 2-oxo-oxirane-3-yl and 2-oxo-oxirane-4-yl groups.

Specific examples of the acid-stable monomer having the norbornene ring (d-3) include 2-norbornene, 2-hydroxy-5-norbornene, 5-norbornene-2-carboxylic acid, methyl 5-norbornene-2-carboxylate, 2-hydroxy-1-ethyl 5-norbornene-2-carboxylate, 5-norbornene-2-methanol and 5-norbornene-2,3-dicarboxylic acid anhydride.

When the resin (A) contains the structural unit derived from the monomer represented by the formula (d-1), the monomer represented by the formula (d-2) or the monomer represented by the formula (d-3), the content thereof is generally 2 to 40 mol %, preferably 3 to 30 mol %, and more preferably 5 to 20 mol %, with respect to the total structural units constituting the resin (A).

The preferable resin (A) is a copolymer polymerized at least the acid-labile monomer having the acid-labile group (a) and the acid-stable monomer having a hydroxy group (b) and/or the acid-stable monomer having a lactone ring(c). In this preferable copolymer, the acid-labile monomer (a) is preferably at least one of the monomer having the adamantyl group (a-1) and the monomer having the cyclohexyl group (a-2), and more preferably the monomer having the adamantyl group (a-1). The acid-stable monomer having the hydroxy group is preferably the monomer having the hydroxyadamantyl group (b-2), and the acid-stable monomer having the lactone ring (c) is preferably at least one of the monomer having the γ-butyrolactone ring (c-1) and the monomer having the condensed ring of the γ-butyrolactone ring and the norbornene ring (c-2).

The resin (A) can be produced by a known polymerization method, for example, radical polymerization method.

The weight average molecular weight of the resin (A) is preferably 2500 or more (more preferably 3000 or more, and still more preferably 3500 or more), and 50,000 or less (more preferably 30,000 or less, and still more preferably 10,000 or less).

The resist composition of the present invention preferably contains 80 mass % or more and 99 mass % or less of the resin (A) based on the solid content of the resist composition. The term "solid content of the resist composition" means a total content of the all ingredients other than a solvent. The solid content of the resist composition and the content of the resin (A) with respect thereto can be measured with a known analytical method such as, for example, liquid chromatography and gas chromatography.

<Basic Compound (Hereinafter May be Referred to "Basic Compound (C)">

The resist composition of the present invention is preferably may contain a basic compound (C). The content of the basic compound (C) is preferably about 0.01 to 1 mass % based on the solid content of the resist composition.

As the basic compounds (C), nitrogen-containing basic organic compounds (for example, amine and ammonium salt) are preferable. The amine may be any of an aliphatic amine and an aromatic amine. The aliphatic amine may be any of a primary amine, secondary amine and tertiary amine. The aromatic amine includes an amine in which an amino group is bonded to an aromatic ring such as aniline, and a heteroaromatic amine such as pyridine.

Preferred basic compounds (C) is an aromatic amine presented by the formula (C2), particularly, an aniline represented by the formula (C2-1).

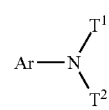

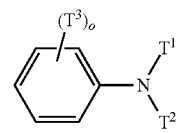

wherein Ar represents an aromatic hydrocarbon group;

$T^1$ and $T^2$ independently represent a hydrogen atom, an aliphatic hydrocarbon group (preferably an alkyl group), a saturated cyclic hydrocarbon group (preferably a cycloalkyl group) or a aromatic hydrocarbon group, one or more hydrogen atom contained in the aliphatic hydrocarbon group, the saturated cyclic hydrocarbon group and the aromatic hydrocarbon group may be replaced with a hydroxy group, an amino group or a $C_1$ to $C_6$ alkoxy group, one or more hydrogen atom contained in the amino group may be replaced with a $C_1$ to $C_4$ alkyl group;

$T^3$ represents an aliphatic hydrocarbon group (preferably an alkyl group), an alkoxy group, a saturated cyclic hydrocarbon group (preferably a cycloalkyl group) or a aromatic hydrocarbon group, one or more hydrogen atom contained in the aliphatic hydrocarbon group, the alkoxy group, the saturated cyclic hydrocarbon group and the aromatic hydrocarbon group may be replaced with the same substituents as defined above;

o represents an integer of 0 to 3.

In the formula (C2) and the formula (C2-1), the aliphatic hydrocarbon group is preferably a group having 1 to 6 carbon atoms.

The saturated cyclic hydrocarbon group is preferably a group having 5 to 10 carbon atoms.

The aromatic hydrocarbon group is preferably a group having 6 to 10 carbon atoms.

The alkoxy group is preferably a group having 1 to 6 carbon atoms.

Examples of the aromatic amine represented by the formula (C2) include 1-naphthylamine and 2-naphthylamine.

Examples of the aniline represented by the formula (C2-1) include aniline, diisopropylaniline, 2-, 3- or 4-methylaniline, 4-nitroaniline, N-methylaniline, N,N-dimethylaniline and diphenylamine. Among these, diisopropylaniline (particularly 2,6-diisopropylaniline) is preferable.

Examples of the basic compound (C) also include compounds represented by the formula (C3) to the formula (C11).

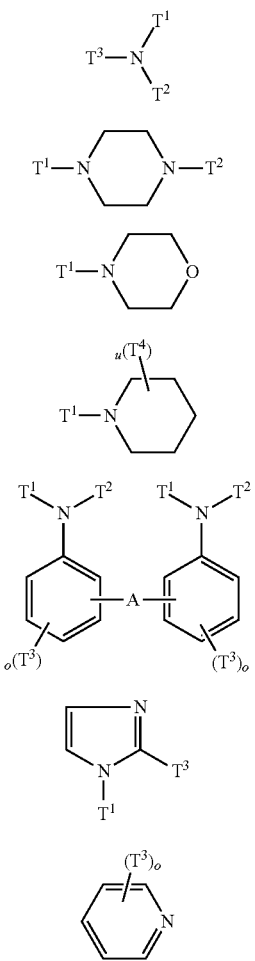

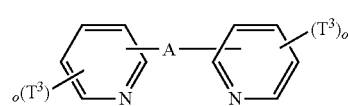

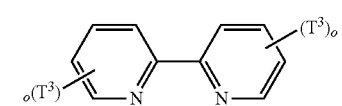

wherein $T^1$, $T^2$, $T^3$ and o represents any of the group as defined above;

$T^4$ represents an aliphatic hydrocarbon group, a saturated cyclic hydrocarbon group or an alkanoyl group, the aliphatic hydrocarbon group is preferably a group having 1 to 6 carbon atoms, the saturated cyclic hydrocarbon group is preferably a group having 3 to 6 carbon atoms, the alkanoyl group is preferably a group having 2 to 6 carbon atoms.

u represents an integer of 0 to 8;

A independently represents a divalent aliphatic hydrocarbon group (preferably an alkylene group), —CO—, —C(=NH)—, —C(=NR$^{36}$)—, —S—, —S—S— or a combination thereof, the divalent aliphatic hydrocarbon group is preferably a group having 1 to 6 carbon atoms, $R^{36}$ represents a $C_1$ to $C_4$ alkyl group.

Examples of the alkanoyl group include acetyl, ethylcarbonyl and heptylcarbonyl groups.

Examples of the compound represented by the formula (C3) include, for example, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl] amine, triisopropanolamine, ethylenediamine, tetramethylene diamine, hexamethylene diamine, 4,4'-diamino-1,2-diphenylethane, 4,4'-diamino-3,3'-dimethyldiphenylmethane and 4,4'-diamino-3,3'-diethyldiphenylmethane.

Examples of the compound represented by the formula (C4) include, for example, piperazine.

Examples of the compound represented by the formula (C5) include, for example, morpholine.

Examples of the compound represented by the formula (C6) include, for example, piperidine, a hindered amine compound having piperidine skeleton described in JP-H11-52575-A.

Examples of the compound represented by the formula (C7) include, for example, 2,2'-methylenebisaniline.

Examples of the compound represented by the formula (C8) include, for example, imidazole and 4-methylimidazole.

Examples of the compound represented by the formula (C9) include, for example, pyridine and 4-methylpyridine.

Examples of the compound represented by the formula (C10) include, for example, 1,2-di(2-pyridyl)ethane, 1,2-di(4-pyridyl)ethane, 1,2-di(2-pyridyl)ethene, 1,2-di(4-pyridyl)ethene, 1,3-di(2-pyridyl)propane, 1,2-di(4-pyridyloxy)

ethane, di(2-pyridyl)ketone, 4,4'-dipyridyl sulfide, 4,4'-dipyridyl disulfide, 2,2'-dipyridylamine and 2,2'-dipicolylamine.

Examples of the compound represented by the formula (C11) include, for example, bipyridine.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

<Solvent (Hereinafter May be Referred to "Solvent (E)")>

The resist composition of the present invention may include a solvent (E). If the resist composition contain the solvent, it is suitable to produce the thin resist film. The content of the solvent may be 90 mass % or more (preferably 92 mass % or more, and more preferably 94 mass % or more), and 99.9 mass % or less (and preferably 99 mass % or less) in the composition. The content of the solvent (E) can be measured with a known analytical method such as, for example, liquid chromatography and gas chromatography.

Examples of the solvent (E) include glycol ether esters such as ethylcellosolve acetate, methylcellosolve acetate and propylene glycol monomethyl ether acetate; ethers such as diethylene glycol dimethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used singly or in combination with two or more.

<Other Ingredient (Hereinafter May be Referred to "Other Ingredient (F)")>

The resist composition can also include various additives as needed. Examples of the other ingredient (F) include sensitizers, dissolution inhibitors, surfactants, stabilizers and dyes, but are not limited to.

<Method for Producing Resist Pattern>

The method for producing resist pattern of the present invention includes steps of:

(1) applying the abovementioned resist composition of the present invention onto a substrate;

(2) drying solvent of the applied composition to form a composition layer;

(3) exposing to the composition layer using an exposure apparatus;

(4) heating the exposed composition layer and, (5) developing the heated composition layer using a developing apparatus.

The application of the resist composition onto the substrate can generally be carried out through the use of a device such as a spin coater.

The drying, for example, can either be carried out by evaporation of the solvent using a heating device such as a hotplate (so-called "prebake"), or can be carried out using a decompression device, and a composition layer with the solvent removed is formed. The temperature in this case is generally the range of 50 to 200° C. Moreover, the pressure is generally the range of 1 to $1.0 \times 10^5$ Pa.

The composition layer obtained is generally exposed using an exposure apparatus or a liquid immersion exposure apparatus. The exposure is generally carried out through a mask that corresponds to the required pattern. Various types of exposure light source can be used, such as irradiation with ultraviolet lasers such as KrF excimer laser (wavelength: 248 nm), ArF excimer laser (wavelength: 193 nm), $F_2$ excimer laser (wavelength: 157 nm), or irradiation with far-ultraviolet wavelength-converted laser light from a solid-state laser source (YAG or semiconductor laser or the like) or vacuum ultraviolet harmonic laser light or the like. Also, the exposure device may be one which irradiates electron beam or extreme-ultraviolet (EUV) generated from plasma.

After exposure, the composition layer is subjected to a heat treatment (so-called "post-exposure bake") to promote the deprotection reaction. The heating temperature is generally in the range of 50 to 200° C., preferably in the range of 70 to 150° C.

The composition layer is developed after the heat treatment, generally by utilizing an alkaline developing solution using a developing apparatus. Here, for the alkaline developing solution, various types of aqueous alkaline solutions used in this field can be satisfactory. Examples include aqueous solutions of tetramethylammonium hydroxide and (2-hydroxyethyl)trimethylammonium hydroxide (common name: choline).

After developing, it is preferable to rinse with ultrapure water and to remove any residual water on the substrate and the pattern.

<Application>

The resist composition of the present invention are useful in chemically amplified photoresist composition, and can be used in the microfabrication of semiconductors and in manufacture of liquid crystals, thermal print heads for circuit boards and the like, and furthermore in other photofabrication processes, and they can be suitably used in a wide range of applications. In particular, they can be used as a suitable chemically amplified photoresist composition for excimer laser lithography such as with ArF, KrF or the like, as well as ArF liquid immersion exposure lithography, electron-beam (EB) exposure lithography and EUV exposure lithography. Moreover, in addition to liquid immersion exposure, they can also be used in dry exposure and the like. Furthermore, they can also be used in double imaging, and have industrial utility.

EXAMPLES

The present invention will be described more specifically by way of examples, which are not construed to limit the scope of the present invention.

All percentages and parts expressing the content or amounts used in the Examples and Comparative Examples are based on weight, unless otherwise specified.

The structures of the compounds were verified by mass analysis (LC:Agilent 1100 type, MASS:Agilent LC/MSD type).

The weight average molecular weight is a value determined by gel permeation chromatography (Toso Co. ltd. HLC-8120GPC type, column: three of TSK gel Multipore HXL-M, solvent: tetrahydrofuran) using polystyrene as the standard product.

Column: TSKgel Multipore $H_{xL}$-Mx3 connecting +guard-column (Toso Co. ltd.)

Eluant: tetrahydrofuran

Flow rate: 1.0mL/min

Detecting device: RI detector

Column temperature: 40 ° C.

Injection amount: 100 μL

Standard material for calculating molecular weight: standard polystyrene (Tosoh Co. ltd.)

Example 1

Synthesis of a Salt Represented by the Formula (B1)

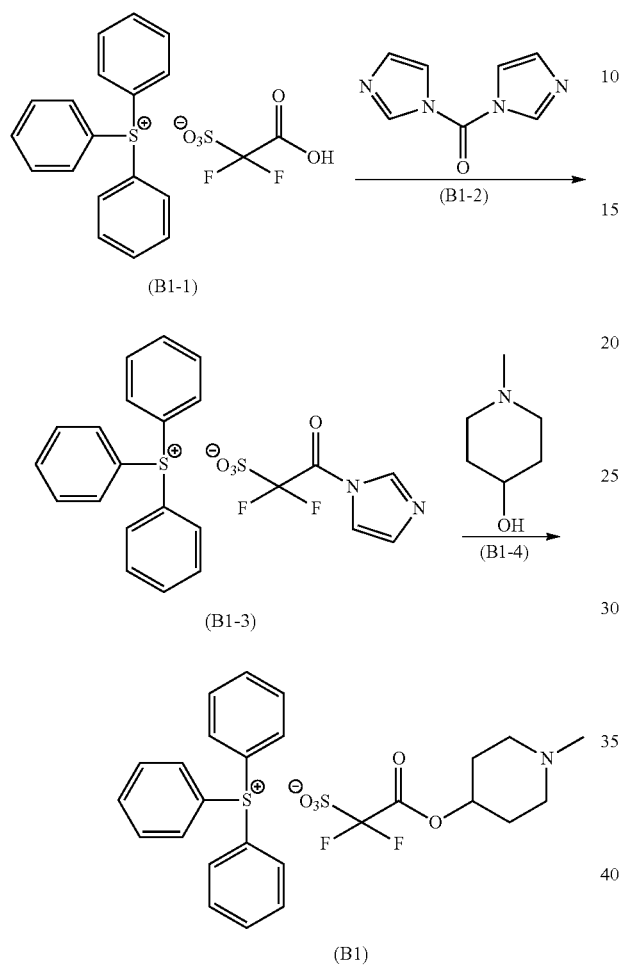

The salt represented by the formula (B1-1) was synthesized according to the method described in JP 2008-127367-A.

10.0 parts of the salt represented by the formula (B1-1) and 60.00 parts of acetonitrile were charged, and stirred for 30 minutes at 40° C., 4.44 parts of the compound represented by the formula (B1-2) was added thereto. The resultant was stirred for 1 hour at 50° C. to obtain the solution containing the compound represented by the formula (B1-3). To the obtained solution, 2.63 parts of the compound represented by the formula (B1-4) was added, and stirred for 1 hour at 23° C. To the obtained reacted mass, 80 parts of chloroform and 30 parts of ion-exchanged water were added, stirred, and separated to obtain an organic layer. The obtained organic layer was washed with water for five times. To the obtained organic layer, 1 part of activated carbon was added, and the mixture was stirred for 30 minutes at 23° C. and filtrated. The filtrate was concentrated to obtain a concentrate, to this concentrate 25 parts of acetonitrile was added to dissolve, and the obtained mixture was concentrated. To the obtained residue, 30 parts of tert-butyl methyl ether was added, stirred for 30 minutes, filtrate to obtain 4.48 parts of the salt represented by the formula (B1).

Identification of the salt represented by the formula (B1):
MS (ESI (+) Spectrum): M$^+$263.1
MS (ESI (−) Spectrum): M$^-$272.0

Example 2

Synthesis of a Salt Represented by the Formula (B2)

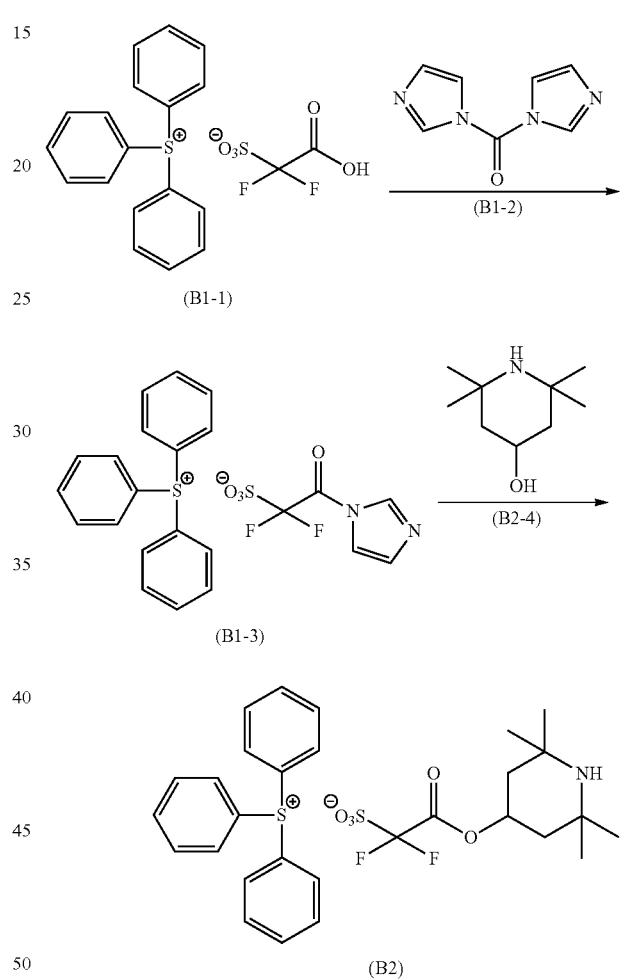

The salt represented by the formula (B1-1) was synthesized according to the method described in JP 2008-127367-A.

10.0 parts of the salt represented by the formula (B1-1) and 60.00 parts of acetonitrile were charged, and stirred for 30 minutes at 40° C., 4.44 parts of the compound represented by the formula (B1-2) was added thereto. The resultant was stirred for 1 hour at 50° C. to obtain the solution containing the compound represented by the formula (B1-3). To the obtained solution, 2.95 parts of the compound represented by the formula (B2-4) was added, and stirred for 1 hour at 23° C. To the obtained reacted mass, 80 parts of chloroform and 30 parts of ion-exchanged water were added, stirred, and separated to obtain an organic layer. The obtained organic layer was washed with water for five times. To the obtained organic layer, 1 part of activated carbon was added, and the mixture was stirred for 30 minutes at 23° C., and filtrated. The filtrate was concentrated to obtain a concentrate, to this concentrate, 30 parts of acetonitrile was added to dissolve, and the obtained mixture was concentrated. To the obtained residue, 40 parts of tert-butyl methyl ether was added, stirred for 30 minutes, filtrate to obtain 4.09 parts of the salt represented by the formula (B2).

Identification of the salt represented by the formula (B2):
MS (ESI(+) Spectrum): M$^+$263.1
MS (ESI(-) Spectrum): M$^-$314.1

Example 3

Synthesis of a Salt Represented by the Formula (B3)

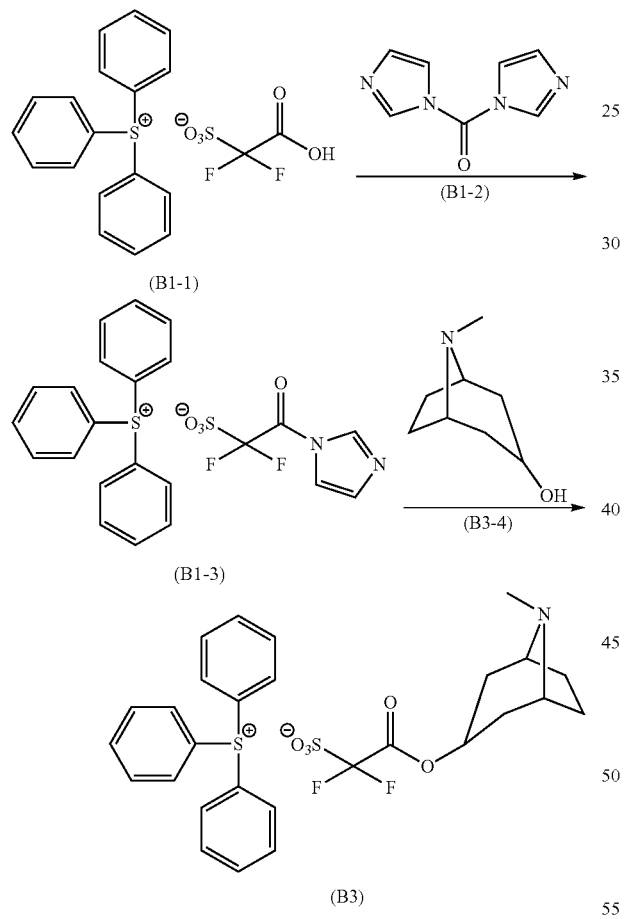

(B3)

The salt represented by the formula (B1-1) was synthesized according to the method described in JP 2008-127367-A.

10.0 parts of the salt represented by the formula (B1-1) and 60.00 parts of acetonitrile were charged, and stirred for 30 minutes at 40° C., 4.44 parts of the compound represented by the formula (B1-2) was added thereto. The resultant was stirred for 1 hour at 50° C. to obtain the solution containing the compound represented by the formula (B1-3). To the obtained solution, 3.22 parts of the compound represented by the formula (B3-4) was added, and stirred for 1 hour at 23° C. To the obtained reacted mass, 80 parts of chloroform and 30 parts of ion-exchanged water were added, stirred, and separated to obtain an organic layer. The obtained organic layer was washed with water for five times. To the obtained organic layer, 1 part of activated carbon was added, and the mixture was stirred for 30 minutes at 23° C., and filtrated. The filtrate was concentrated to obtain a concentrate, to this concentrate, 30 parts of acetonitrile was mixed to dissolve, and the obtained mixture was concentrated. To the obtained residue, 50 parts of tert-butyl methyl ether was added, stirred for 30 minutes, filtrate to obtain 7.79 parts of the salt represented by the formula (B3).

Identification of the salt represented by the formula (B3):
MS (ESI(+) Spectrum): M$^+$263.1
MS (ESI(-) Spectrum): M$^-$298.1

Example 4

Synthesis of a Salt Represented by the Formula (B4)

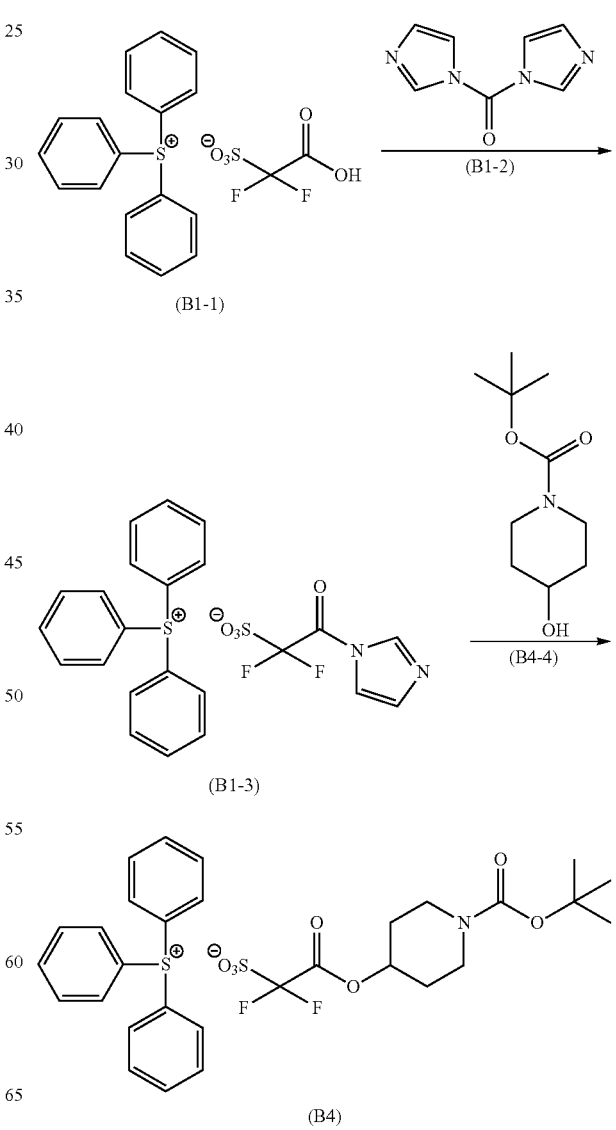

(B4)

The salt represented by the formula (B1-1) was synthesized according to the method described in JP 2008-127367-A.

10.0 parts of the salt represented by the formula (B1-1) and 60.00 parts of acetonitrile were charged, and stirred for 30 minutes at 40° C., 4.44 parts of the compound represented by the formula (B1-2) was added thereto. The resultant was stirred for 1 hour at 50° C. to obtain the solution containing the compound represented by the formula (B1-3). To the obtained solution, 4.59 parts of the compound represented by the formula (B4-4) was added, and stirred for 1 hour at 23° C. To the obtained reacted mass, 80 parts of chloroform and 30 parts of ion-exchanged water were added, stirred, and separated to obtain an organic layer. The obtained organic layer was washed with water for five times. To the obtained organic layer, 1 part of activated carbon was added, and the mixture was stirred for 30 minutes at 23° C., and filtrated. The filtrate was concentrated to obtain a concentrate, to this concentrate, 30 parts of acetonitrile was mixed to dissolve, and the obtained mixture was concentrated. To the obtained residue, 50 parts of tert-butyl methyl ether was added, stirred for 30 minutes, filtrate to obtain 6.86 parts of the salt represented by the formula (B4).

Identification of the salt represented by the formula (B4):
MS (ESI(+) Spectrum): M$^+$263.1
MS (ESI(−) Spectrum): M$^−$358.1

Example 5

Synthesis of a Salt Represented by the Formula (B5)

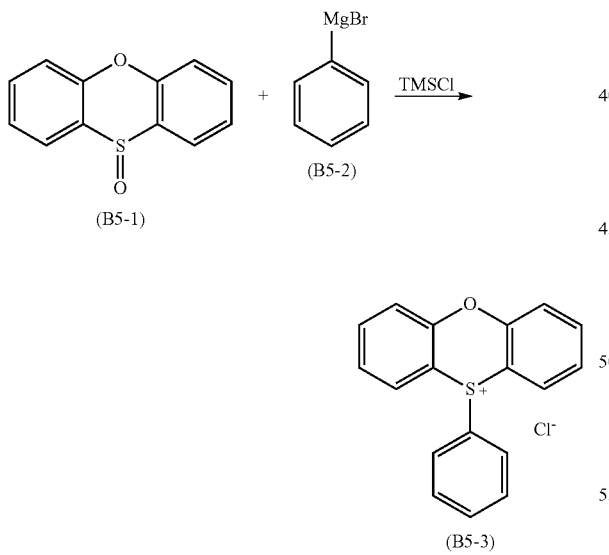

50.00 parts of the compound represented by the formula (B5-1) and 250 parts of tetrahydrofuran were charged in the reactor, and stirred for 30 minutes at 30 ° C., 50.23 parts of trimethylsilyl chloride was added in the form of drops. The resulting mixed solution was cooled to 0 ° C. To the obtained solution, 157.20 parts of the compound represented by the formula (B5-2) (32% purity, manufactured by Tokyo chemical industry Co., LTD.) was added in the form of drops for 30 minutes. This obtained mixture was elevated the temperature to 23 ° C., and stirred at the same temperature. To the obtained reacted mixture, 125 parts of 1N hydrochloric acid was added, stirred, stood and separated to obtain an aqueous layer. To the obtained aqueous layer, 125 parts of tert-butyl methyl ether was added, stirred, stood and separated to obtain an aqueous layer. To the obtained aqueous layer, 125 parts of chloroform was added, stirred, stood and separated to obtain an organic layer. The obtained organic layer was filtrated, and the obtained filtrate was concentrated. To the concentrated residue was 28.33 parts of acetonitrile and 354.15 parts of tert-butyl methyl ether was added, stirred for 30 minutes at 23 ° C. to obtain precipitate, and the precipitate was filtrate to obtain 53.00 parts of the compound represented by the formula (B5-3).

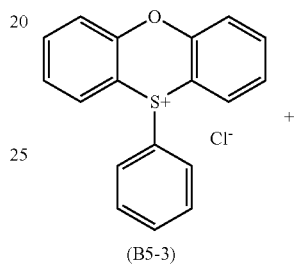

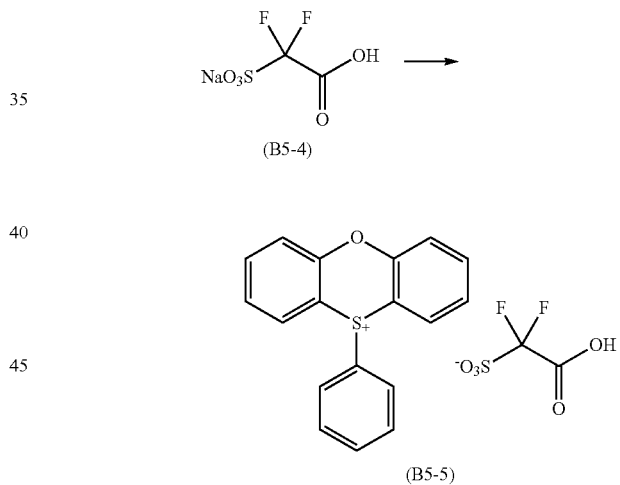

13.12 parts of the compound represented by the formula (B5-4) and 73.86 parts of chloroform were charged in the reactor, and stirred for 30 minutes at 30 ° C., 20.71 parts of the salt represented by the formula (B5-3) and 62.27 parts of ion-exchanged water were added. To the resulting mixed solution, 6.90 parts of 35% hydrochloric acid was added in the form of drops, stirred for 12 hours at 23 ° C. To the obtained reacted mixture, 12.00 parts of 28% ammonia water was added in the form of drops, and this was separated to obtain an organic layer. To the obtained organic layer was added 50 parts of ion-exchanged water, stirred, stood, and separated to obtain an organic layer. This washing with water operation was repeated a total of five times. To the obtained organic layer, 2.00 part of activated carbon was added, and the mixture was stirred for 30 minutes at 23 ° C., and filtrated. The filtrate was concentrated to obtain a concentrate, to this concentrate, 30 parts of acetonitrile and 150 parts of tert-butyl methyl ether were added, stirred, and filtrate to obtain 14.28 parts of the salt represented by the formula (B5-5).

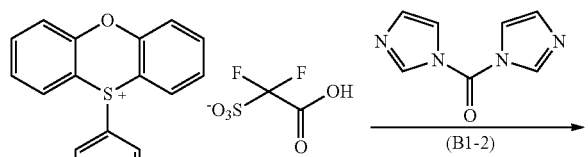

(B5-5)

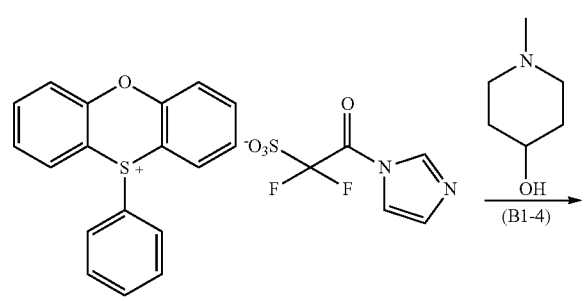

(B5-6)

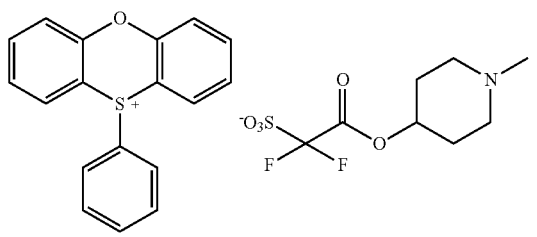

(B5)

10.32 parts of the salt represented by the formula (B5-5) and 61.91 parts of acetonitrile were charged, and stirred for 30 minutes at 40° C., 4.44 parts of the compound represented by the formula (B1-2) was added thereto. The resultant was stirred for 1 hour at 50° C. to obtain the solution containing the compound represented by the formula (B5-6). To the obtained solution, 2.63 parts of the compound represented by the formula (B 1-4) was added, and stirred for 1 hour at 23° C. To the obtained reacted mass, 100 parts of chloroform and 50 parts of ion-exchanged water were added, stirred, and separated to obtain an organic layer. The obtained organic layer was washed with water for five times. To the obtained organic layer, 1 part of activated carbon was added, and the mixture was stirred for 30 minutes at 23° C., and filtrated. The filtrate was concentrated to obtain a concentrate, to this concentrate, 30 parts of acetonitrile was mixed to dissolve, and the obtained mixture was concentrated. To the obtained residue, 30 parts of tert-butyl methyl ether was added, stirred for 30 minutes, filtrate to obtain 10.81 parts of the salt represented by the formula (B5).

Identification of the salt represented by the formula (B5):

MS (ESI(+) Spectrum): M$^+$277.1

MS (ESI(−) Spectrum): M$^-$272.0

Example 6

Synthesis of a Salt Represented by the Formula (B6)

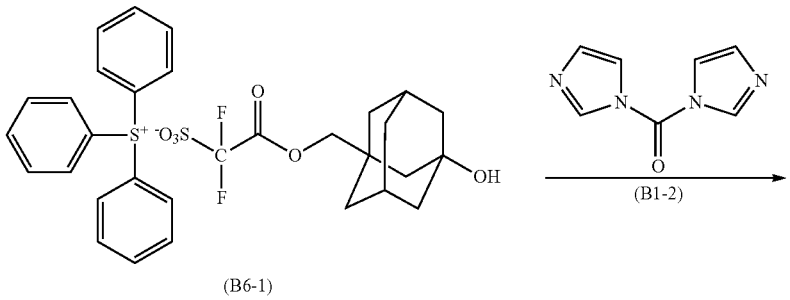

(B6-1)

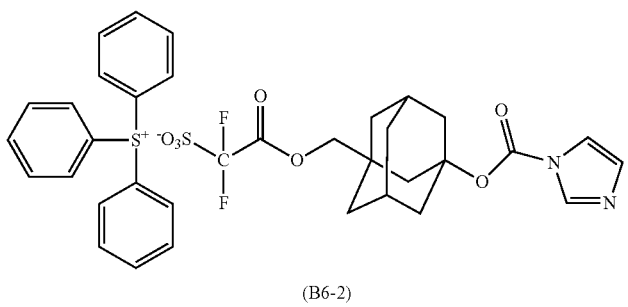

(B6-2)

6.03 parts of the salt represented by the formula (B6-1) and 30.00 parts of acetonitrile were charged, and stirred for 30 minutes at 23° C., 1.70 parts of the compound represented by the formula (B1-2) was added thereto. The resultant was stirred for 1 hour at 60° C. To the obtained reacted solution was filtrated, and the obtained filtrate was concentrated. To the obtained concentrate, 30 parts of chloroform and 15 parts of ion-exchanged water were added, stirred for 30 minutes at 23° C., stood, and separated to obtain an organic layer. To the obtained organic layer, 15 parts of ion-exchanged water was added, and stirred for 30 minutes at 23° C. This washing with water operation was repeated further three times. The obtained organic layer, 1 part of activated carbon was added, and the mixture was stirred for 30 minutes at 23° C., and filtrated. The filtrate was concentrated to obtain a concentrate, to this concentrate, 100 parts of tert-butyl methyl ether was added, stirred, and filtrate to obtain 6.12 parts of the salt represented by the formula (B6-2).

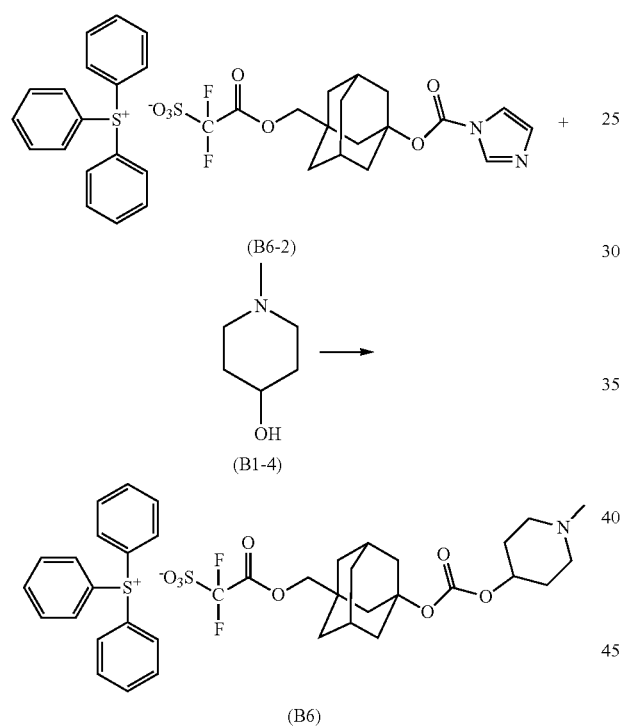

8.00 parts of the salt represented by the formula (B6-2), 48.00 parts of the dimethylformamide and 1.60 parts of the compound represented by the formula (B1-4) were charged, and stirred for 30 minutes at 23° C. 0.24 parts of potassium carbonate was added thereto, and the obtained mixture was stirred for 2 hours at 23° C. To the obtained reactant, 100 parts of chloroform and 30 parts of ion-exchanged water were added, stirred, and separated to obtain an organic layer. The obtained organic layer was washed with water for six times. To the obtained organic layer, 1 part of activated carbon was added, and the mixture was stirred for 30 minutes at 23° C., and filtrated. The filtrate was concentrated to obtain a concentrate, to this concentrate, 20 parts of acetonitrile was mixed to dissolve, and concentrated. To the obtained residue, 50 parts of tert-butyl methyl ether was added, stirred, and remove a supernatant. The obtained residue was dissolved in chloroform, and the obtained residue was concentrated to obtain 4.88 parts of the salt represented by the formula (B6).

Identification of the salt represented by the formula (B6):
MS (ESI(+) Spectrum): $M^+$263.1
MS (ESI(−) Spectrum): $M^-$480.2

Example 7

Synthesis of a Salt Represented by the Formula (B7)

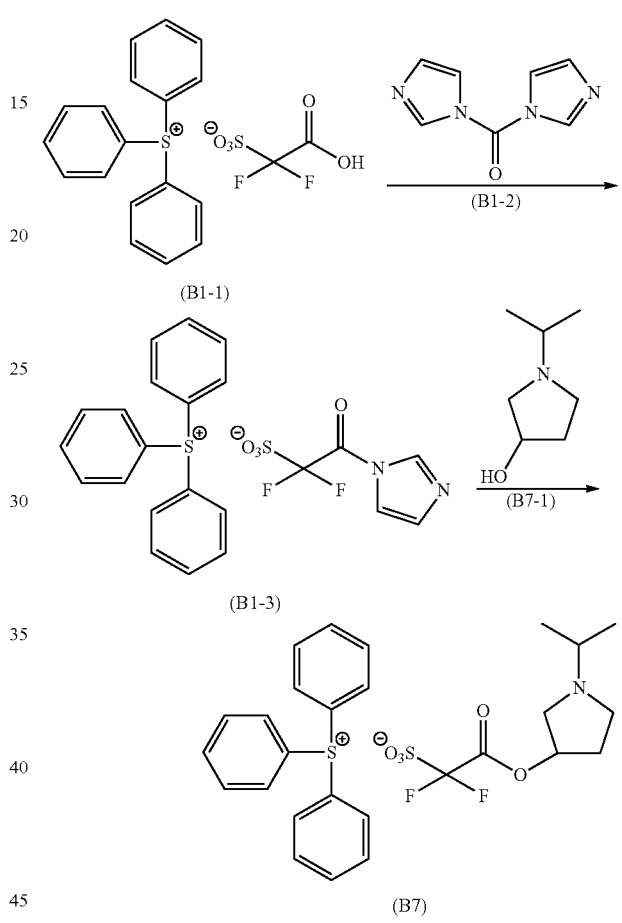

10.0 parts of the salt represented by the formula (B1-1) and 60.00 parts of acetonitrile were charged, and stirred for 30 minutes at 40° C., 4.44 parts of the compound represented by the formula (B1-2) was added thereto. The resultant was stirred for 1 hour at 50° C. to obtain the solution containing the compound represented by the formula (B1-3). To the obtained solution, 2.95 parts of the compound represented by the formula (B7-1) was added, and stirred for 1 hour at 23° C. To the obtained reacted mass, 80 parts of chloroform and 30 parts of ion-exchanged water were added, stirred, and separated to obtain an organic layer. The obtained organic layer was washed with water for five times. To the obtained organic layer, 1 part of activated carbon was added, and the mixture was stirred for 30 minutes at 23° C., and filtrated. The filtrate was concentrated to obtain a concentrate, to this concentrate, 25 parts of acetonitrile was mixed to dissolve, and the obtained mixture was concentrated. To the obtained residue, 30 parts of tert-butyl methyl ether was added, stirred for 30 minutes, filtrate to obtain 7.48 parts of the salt represented by the formula (B7).

Identification of the salt represented by the formula (B7):

MS (ESI(+) Spectrum): M⁺263.1

MS (ESI(−) Spectrum): M⁻286.1

The monomers used in the synthesis of the resin are shown below.

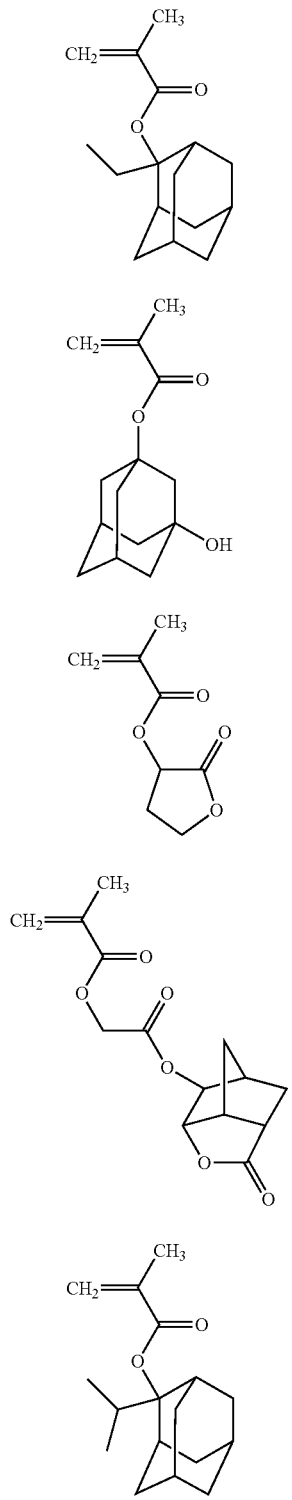

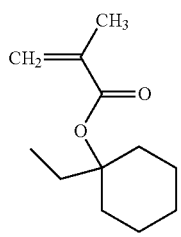

Synthetic Example 1

Synthesis of Resin A1

Monomer E, monomer F, monomer B, monomer C and monomer D were charged with molar ratio 30:14:6:20:30, and dioxane was added thereto in an amount equal to 1.5 weight times of the total amount of monomers to obtain a solution. Azobisisobutyronitrile and azobis(2,4-dimethylvaleronitrile) was added as an initiator thereto in an amount of 1 mol % and 3 mol % respectively with respect to the entire amount of monomers, and the resultant mixture was heated for about 5 hours at 73° C. After that, the reaction solution was poured into a mixture of methanol and ion-exchanged water (4:1) in large amounts to precipitate. These operations were repeated 3 times for purification, thereby resulting in 65% yield of copolymer having a weight average molecular weight of about 8100. This copolymer, which had the structural units derived from the monomers of the following formula, was designated Resin A1.

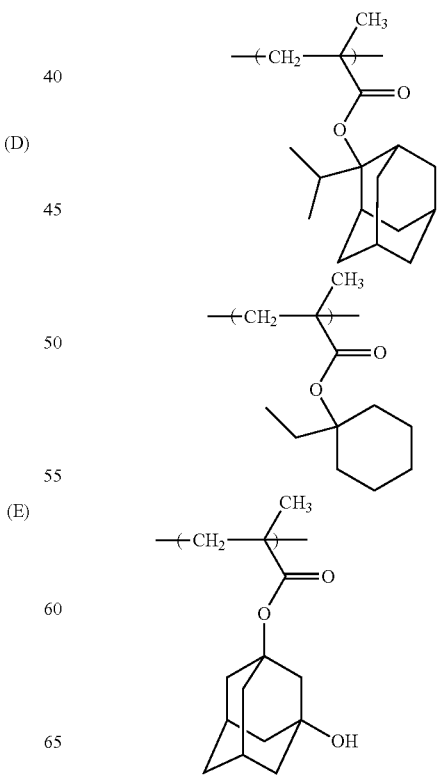

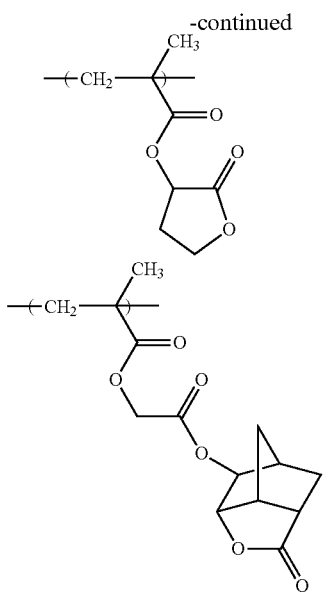

Synthetic Example 2

Synthesis of Resin A2

Monomer A, monomer B and monomer C were mixed with molar ratio 50:25:25, and dioxane was added thereto in an amount equal to 1.5 weight times of the total amount of monomers. Azobisisobutyronitrile and azobis(2,4-dimethyl valeronitrile) was added as an initiator thereto in an amount of 1 mol % and 3 mol % respectively with respect to the entire amount of monomers, and the resultant mixture was heated for about 8 hours at 80° C. After that, the reaction solution was poured into a mixture of methanol and ion-exchanged water (3:1) in large amounts to precipitate. These operations were repeated 3 times for purification, thereby resulting in 60% yield of copolymer having a weight average molecular weight of about 9200. This copolymer, which had the structural units derived from the monomers of the following formulae, was designated Resin A2.

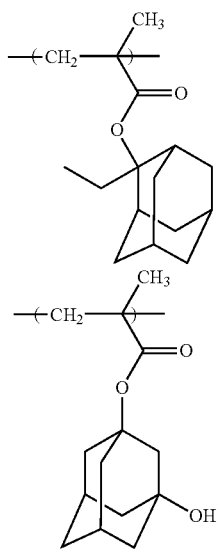

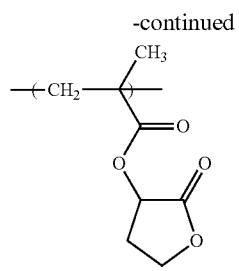

(Preparing Resist Composition)

Resist compositions were prepared by mixing and dissolving each of the components shown in Table 1, and then filtering through a fluororesin filter having 0.2 μm pore diameter.

TABLE 1

| | Resin (parts) | Acid generator (parts) | Quencher (parts) | PB/PEB (° C./° C.) |
|---|---|---|---|---|
| Ex. 8 | A1 = 10 | B1 = 1.00 | C1 = 0.07 | 100/100 |
| Ex. 9 | A1 = 10 | B2 = 1.00 | C1 = 0.07 | 100/100 |
| Ex. 10 | A1 = 10 | B3 = 1.00 | C1 = 0.07 | 100/100 |
| Ex. 11 | A1 = 10 | B4 = 1.00 | C1 = 0.07 | 100/100 |
| Ex. 12 | A1 = 10 | B1/X1 = 0.30/0.70 | C1 = 0.07 | 100/100 |
| Ex. 13 | A1 = 10 | B1/X2 = 0.30/0.70 | C1 = 0.07 | 100/100 |
| Ex. 14 | A1 = 10 | B2/X2 = 0.30/0.70 | C1 = 0.07 | 100/100 |
| Ex. 15 | A1 = 10 | B3/X2 = 0.30/0.70 | C1 = 0.07 | 100/100 |
| Ex. 16 | A1 = 10 | B4/X2 = 0.30/0.70 | C1 = 0.07 | 100/100 |
| Ex. 17 | A2 = 10 | B2 = 1.00 | C1 = 0.07 | 110/110 |
| Ex. 18 | A1 = 10 | B2 = 1.00 | — | 100/100 |
| Ex. 19 | A1 = 10 | B2/X1 = 0.05/0.95 | C1 = 0.07 | 100/100 |
| Ex. 20 | A1 = 10 | B2/X2 = 0.50/0.50 | C1 = 0.07 | 100/100 |
| Ex. 21 | A1 = 10 | B5 = 1.00 | C1 = 0.07 | 100/100 |
| Ex. 22 | A1 = 10 | B5/X2 = 0.30/0.70 | C1 = 0.07 | 100/100 |
| Ex. 23 | A1 = 10 | B6 = 1.00 | C1 = 0.07 | 100/100 |
| Ex. 24 | A1 = 10 | B6/X2 = 0.30/0.70 | C1 = 0.07 | 100/100 |
| Ex. 25 | A1 = 10 | B7 = 1.00 | C1 = 0.07 | 100/100 |
| Ex. 26 | A1 = 10 | B7/X2 = 0.30/0.70 | C1 = 0.07 | 100/100 |
| Comp. Ex. 1 | A2 = 10 | X1 = 1.00 | C1 = 0.07 | 110/110 |

<Resin>

Resin A1 and A2

<Acid Generator>

Acid generator B1: salt represented by the formula (B1)

Acid generator B2: salt represented by the formula (B2)

Acid generator B3: salt represented by the formula (B3)

Acid generator B4: salt represented by the formula (B4)

Acid generator B5: salt represented by the formula (B5)

Acid generator B6: salt represented by the formula (B6)

Acid generator B7: salt represented by the formula (B7)

Acid generator X1:

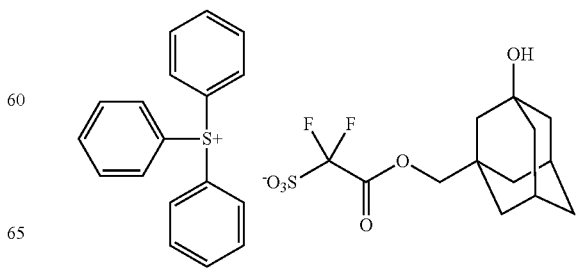

Acid generator X2:

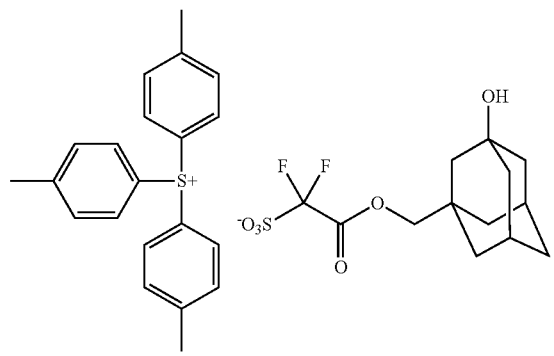

<Qencher>
C1: 2,6-diisopropylaniline,
<Solvent>

| | |
|---|---|
| Propylene glycol monomethyl ether acetate | 265.0 parts |
| 2-Heptanone | 20.0 parts |
| Propylene glycol monomethyl ether | 20.0 parts |
| γ-butyrolactone | 3.5 parts |

(Producing Resist Pattern)

A composition for an organic antireflective film ("ARC-29", by Nissan Chemical Co. Ltd.) was applied onto 12-inch silicon wafers and baked for 60 seconds at 205° C. to form a 78 nm thick organic antireflective film.

The above resist compositions were then applied thereon by spin coating so that the thickness of the resulting film became 110 nm after drying (pre-baking).

The obtained wafers were then pre-baked for 60 seconds on a direct hot plate at the temperatures given in the "PB" column in Table 1.

Line and space patterns were then exposed through stepwise changes in exposure quantity using an ArF excimer laser stepper for immersion lithography ("XT:1900Gi" by ASML Ltd.: NA=1.35, 2-poles on axis lighting (σout=0.97, σin=0.77, Y polarization)), on the wafers on which the resist film had thus been formed. The ultrapure water was used for medium of immersion.

After the exposure, post-exposure baking was carried out by 60 seconds at the temperatures given in the "PEB" column in Table 1.

Then, puddle development was carried out with 2.38 wt % tetramethylammonium hydroxide aqueous solution for 60 seconds to obtain a resist pattern.

Effective sensitivity was represented as the exposure amount at which a 50 nm-width line and space pattern resolved to 1:1 with the each resist pattern produced from the resist composition.

(Exposure Margin Evaluation (EL))

Exposure margin was evaluated from a graph in which the horizontal axis corresponds to the exposure amount within the range of an effective sensitivity ±10%, and the vertical axis corresponds to the a line width of 50 nm-width of line pattern at its amount. In this evaluation, a double circle was given when absolute value of the slope of the regression line obtained from the above plot was 1.1 nm/(mJ/cm²) or less;

a circle was given when absolute value of the slope thereof was 1.3 nm/(mJ/cm²) or less;

a triangle was given when absolute value of a slope thereof was 1.5 nm/(mJ/cm²) or less and more than 1.3 nm/(mJ/cm²);

a cross was given when absolute value of a slope thereof was more than 1.5 nm/(mJ/cm²).

(Focus margin (DOF) Evaluation)

The focus range within a line width of the resist pattern of 50 nm ±5% (47.5 to 52.5 nm) was set for an index (DOF) when the resist pattern was formed through stepwise changes of the focus in the effective sensitivity.

a double circle was given when the DOF was >0.17 µm, a circle was given when the DOF was >0.14 µm and 0.17 µm≤;

a triangle was given when the DOF was >0.09 µm and ≤0.14 µm and a cross was given when the DOF was <0.09 µm.

Table 2 gives the results.

TABLE 2

| | EL | DOF |
|---|---|---|
| Ex. 8 | ○ | ○ |
| Ex. 9 | ○○ | ○○ |
| Ex. 10 | ○ | ○○ |
| Ex. 11 | ○○ | ○○ |
| Ex. 12 | ○ | ○ |
| Ex. 13 | ○○ | ○○ |
| Ex. 14 | ○○ | ○○ |
| Ex. 15 | ○○ | ○○ |
| Ex. 16 | ○○ | ○○ |
| Ex. 17 | ○ | ▲ |
| Ex. 18 | ▲ | ○ |
| Ex. 19 | ○ | ○ |
| Ex. 20 | ○○ | ○○ |
| Ex. 21 | ○○ | ○○ |
| Ex. 22 | ○○ | ○○ |
| Ex. 23 | ○○ | ○○ |
| Ex. 24 | ○○ | ○○ |
| Ex. 25 | ○ | ○ |
| Ex. 26 | ○○ | ○○ |
| Comp. Ex. 1 | x | x |

According to the present resist composition, it is possible to achieve excellent EL and DOF at producing the resist pattern.

What is claimed is:
1. A salt represented by formula (I)

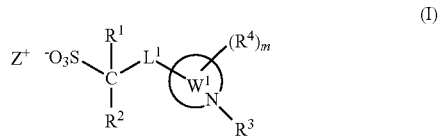

wherein $R^1$ and $R^2$ independently represent a fluorine atom or a $C_1$ to $C_6$ perfluoroalkyl group;
$L^1$ represents a group represented by formula (L 1-1a)

wherein $L^a$ represents a single bond or a $C_1$ to $C_{15}$ saturated hydrocarbon group and

* represent a bond to —C(R$^1$)(R$^2$)—;
ring W$^1$ represents a C$_2$ to C$_{36}$ non-aromatic heterocycle;
a carbon atom in the ring W$^1$ is bonded to L$^1$;
R$^3$ represents a hydrogen atom or a C$_1$ to C$_{12}$ hydrocarbon group, a —CH$_2$— contained in the hydrocarbon group may be replaced by —O— or —CO—;
R$^4$ in each occurrence independently represent a C$_1$ to C$_6$ hydrocarbon group, a —CH$_2$— contained in the hydrocarbon group may be replaced by —O— or —CO—;
m represents an integer of 0 to 6; and
Z$^+$ represents an organic cation.

2. The salt according to claim 1, wherein Z$^+$ is a triaryl sulfonium cation.

3. The salt according to claim 1, wherein R$^3$ represents a C$_1$ to C$_{12}$ hydrocarbon group, a —CH$_2$— contained in the hydrocarbon group may be replaced by —O— or —CO—.

4. An acid generator comprising the salt according to claim 1.

5. The acid generator according to claim 4, further comprising a salt which has the cation contained in the salt represented by the formula (I) and a known anion.

6. A resist composition comprising;
the acid generator according to claim 4, and
a resin,
wherein the resin has an acid-labile group, and is insoluble or poorly soluble in an aqueous alkali solution but becomes soluble in the aqueous alkali solution by the action of an acid.

7. The resist composition according to claim 6, which further comprises a basic compound.

8. A method for producing a resist pattern comprising steps of;
(1) applying the resist composition according to claim 6 or 7 onto a substrate;
(2) drying the applied composition to form a composition layer;
(3) exposing the composition layer using an exposure apparatus;
(4) heating the exposed composition layer, and
(5) developing the heated composition layer using a developing apparatus.

* * * * *